US007585671B2

(12) United States Patent
McMahon et al.

(10) Patent No.: US 7,585,671 B2
(45) Date of Patent: Sep. 8, 2009

(54) HEDGEHOG INTERACTING PROTEINS AND USES RELATED THERETO

(75) Inventors: Andrew P. McMahon, Lexington, MA (US); Pao-Tien Chuang, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 180 days.

(21) Appl. No.: 11/438,749

(22) Filed: May 22, 2006

(65) Prior Publication Data

US 2007/0054290 A1 Mar. 8, 2007

Related U.S. Application Data

(63) Continuation of application No. 10/288,556, filed on Nov. 4, 2002, now Pat. No. 7,115,394, which is a continuation of application No. 08/933,711, filed on Sep. 19, 1997, now Pat. No. 6,514,724.

(60) Provisional application No. 60/026,155, filed on Sep. 20, 1996.

(51) Int. Cl.
*C07K 16/28* (2006.01)
*C12N 5/12* (2006.01)

(52) U.S. Cl. ................. 435/332; 530/388.1; 530/388.2; 530/389.1

(58) Field of Classification Search ....................... None
See application file for complete search history.

(56) References Cited

U.S. PATENT DOCUMENTS

| | | | |
|---|---|---|---|
| 5,200,313 | A | 4/1993 | Carrico |
| 5,837,538 | A | 11/1998 | Scott et al. |
| 5,844,079 | A | 12/1998 | Ingham et al. |

FOREIGN PATENT DOCUMENTS

| | | |
|---|---|---|
| WO | WO 95/18856 | 7/1995 |
| WO | WO 96/16668 | 6/1996 |
| WO | WO 96/17924 | 6/1996 |

OTHER PUBLICATIONS

Chang et al., Products, gene linkage and limb patterning activity of a muirne hedgehog gene, Dev. 120: 3339-3353, 1994.*

(Continued)

*Primary Examiner*—Lorraine Spector
*Assistant Examiner*—Claire Kaufman
(74) *Attorney, Agent, or Firm*—Ropes & Gray LLP

(57) ABSTRACT

The present invention concerns the discovery of a new family of hedgehog binding proteins, referred to herein as "hedgehog interacting proteins" or "HIPs", which are demonstrated to bind to hedgehog polypeptides with high affinity. As described herein, the vertebrate HIP proteins exhibit spatially and temporally restricted expression domains indicative of important roles in hedgehog-mediated induction.

7 Claims, 13 Drawing Sheets

OTHER PUBLICATIONS

Smith et al. Identification of two novel human immunodeficiency virus type 1 splice acceptor sites in infected T cell lines, J. Gen. Virol. 73:1825-1828, 1992.*

Ledley, F.D. Pharm. Res. 13, 1595-1614 (1996).

Orkin et al. in "Report and Recommendations of the Panel to Assess the NIH Investment in Research on Gene Therapy." (Dec. 7, 1995).

Parson. Peptide Hormones, University Park Press pp. 1-7 (Jun. 1976).

Rosenberg et al. Science 287, 175 (2000).

Verma et al. Nature 389, 239-242 (1997).

Hynes et al., Induction of midbrain dopaminergic neurons by sonic hedgehog, Neuron 15:35-44, Jul. 1995.

Vortkamp et al., Regulation of rate of cartilage differentiation by Indian hedgehog and PTH-related protein, Science 273:613-622, Aug. 2, 1996.

Guerrero et al., A protein with several possible membrane-spanning domains encoded by the *Drosophila* segment polarity gene patched, Nature 341:508-513, Oct. 12, 1989.

Christa et al., The human HIP gene, overexpressed in primary liver cancer encodes for a C-type carbohydrate binding protein with lactose binding acvity, FEBS Letters 337:114-118, 1994.

* cited by examiner

HIP-1 Protein

```
human HIP-1        MLKMLSFKLL LLAVALGFFE GDAKFGERNE GSGARRRRCL NGNPPKRLKR    50
mouse HIP-1        MLKMLSFKLL LLAVALGFFE GDAKFGERSE GSGARRRRCL NGNPPKRLKR    50
chick HIP-1        MLKMLPFKLL LVAVALCFFE GDAKFGE--- -SGARRRRCL NGTPPRRLKK    46
zebrafish HIP-1    ---------- ---------- ---------- ---------- ----------
Consensus          MLKML.FKLL L.AVAL.FFE GDAKFGE.... .SGARRRRCL NG.PP.RLK.    50

human HIP-1        RDRRMMSQLE LLSGGEMLCG GFYPRLSCCL RSDSPGLGRL ENKIFSVTNN   100
mouse HIP-1        RDRRVMSQLE LLSGGEILCG GFYPRVSCCL QSDSPGLGRL ENKIFSATNN   100
chick HIP-1        RDRRLLSP-E APGGAEAMCR GLYPRLSCCS RADAQGLLHA GAKILSVTNN    95
zebrafish HIP-1    ---------- ---------- ---------- ---------- ----------
Consensus          RDRR..S..E ...G.E..C. G.YPR.SCC. ..D..GL... ..KI.S.TNN   100

human HIP-1        TECGKLLEEI KCALCSPHSQ SLFHSPER-E VLERDIVLPL LCKDYCKEFF   149
mouse HIP-1        SECSRLLEEI QCAPCSPHSQ SLFYTPER-D VLDGDLALPL LCKDYCKEFF   149
chick HIP-1        TECAKLLEEI KCAHCSPHAQ NLFHSPEKGE TSERELTLPY LCKDYCKEFY   145
zebrafish HIP-1    ---------- ---------- ---------- ---------- ----------
Consensus          .EC..LLEEI .CA.CSPH.Q .LF..PE.-. ......LP. LCKDYCKEF.   150

human HIP-1        YTCRGHIPGF LQTTADEFCF YYARKDGGLC FPDFPRKQVR GPASNYLDQM   199
mouse HIP-1        YTCRGHIPGL LQTTADEFCF YYARKDAGLC FPDFPRKQVR GPASNYLGQM   199
chick HIP-1        YTCRGHLPGF LQTTADEFCF YYARKDGGVC FPDFPRKQVR GPASNSLDHM   195
zebrafish HIP-1    ---------- ---------- ---------- ---------- ----------
Consensus          YTCRGH.PG. LQTTADEFCF YYARKD.G.C FPDFPRKQVR GPASN.L..M   200

human HIP-1        EEYDKVEEIS RKHKHNCFCI QEVVSGLRQP VGALHSGDGS QRLFILEKEG   249
mouse HIP-1        EDYEKVGGIS RKHKHNCLCV QEVMSGLRQP VSAVHSGDGS HRLFILEKEG   249
chick HIP-1        EEYDKEEEIS RKHKHNCFCI QEVMSGLRQP VGAVHCGDGS HRLFILEKEG   245
zebrafish HIP-1    ---------- ---------- QEIHSGLQQP VGVVHCGDGS QRLFILEREG    30
Consensus          E.Y.K...IS RKHKHNC.C. QEV.SGLRQP VGAVH.GDGS .RLFILEKEG   250

human HIP-1        YVKILTPEGE IFKEPYLDIH KLVQSGIKGG DERGLLSLAF HPNYKKNGKL   299
mouse HIP-1        YVKILTPEGE LFKEPYLDIH KLVQSGIKGG DERGLLSLAF HPNYKKNGKL   299
chick HIP-1        YVKIFSPEGD MIKEPFLDIH KLVQSGIKGG DERGLLSLAF HPNYKKNGKL   295
zebrafish HIP-1    FVWILTHDME LLKEPFLDIH KLVQSGLKGG DERGLLSLAF HPNYKKNGKL    80
Consensus          YVKILTPEGE ..KEP.LDIH KLVQSGIKGG DERGLLSLAF HPNYKKNGKL   300

human HIP-1        YVSYTTNQER WAIGPHDHIL RVVEYTVSRK NPHQVDLRTA RIFLEVAELH   349
mouse HIP-1        YVSYTTNQER WAIGPHDHIL RVVEYTVSRK NPHQVDVRTA RVFLEVAELH   349
chick HIP-1        YVSYTTNQER WAIGPHDHIL RVVEYTVSRK NPQQVDIRTA RVFLEVAELH   345
zebrafish HIP-1    YVSYTTNQER WTIGPHDHIL RVVEYTVSRK NPNQVDTRTP RVLMEVAELH   130
Consensus          YVSYTTNQER WAIGPHDHIL RVVEYTVSRK NP.QVD.RTA RVFLEVAELH   350

human HIP-1        RKHLGGQLLF GPDGFLYIIL GDGMITLDDM EEMDGLSDFT GSVLRLDVDT   399
mouse HIP-1        RKHLGGQLLF GPDGFLYIIL GDGMITLDDM EEMDGLSDFT GSVLRLDVDT   399
chick HIP-1        RKHLGGQLLF GPDGFLYVFL GDGMITLDDM EEMDGLSDFT GSVLRLDVNT   395
zebrafish HIP-1    RKHLGGQLLF GPDGLLHIFL GDGMITLDNM EEMDGLSDFT GSVLRVDVDT   180
Consensus          RKHLGGQLLF GPDGFLYI.L GDGMITLDDM EEMDGLSDFT GSVLRLDVDT   400
```

*Figure 1A*

HIP-1 Protein

| | | | | | | |
|---|---|---|---|---|---|---|
| human HIP-1 | DMCNVPYSIP | RSNPHFNSTN | QPPEVFAHGL | HDPGRCAVDR | HPTDININLT | 449 |
| mouse HIP-1 | DMCNVPYSIP | RSNPHFNSTN | QPPEVFAHGL | HDPGRCAVDR | HPTDININLT | 449 |
| chick HIP-1 | DLCSVPYSIP | RSNPHFNSTN | QPPEIFAHGL | HNPGRCAVDH | HPADVNINLT | 445 |
| zebrafish HIP-1 | ECCSTPYSIP | RNNPYFNSTN | QPPEIFAHGL | HDPGRCAVDK | LRMDTNGSLL | 230 |
| Consensus | D.C.VPYSIP | RSNPHFNSTN | QPPE.FAHGL | HDPGRCAVD. | HP.D.NINLT | 450 |
| human HIP-1 | ILCSDSNGKN | RSSARILQII | KGKDYESEPS | LLEFKPFSNG | PLVGGFVYRG | 499 |
| mouse HIP-1 | ILCSDSNGKN | RSSARILQII | KGRDYESEPS | LLEFKPFSNG | PLVGGFVYRG | 499 |
| chick HIP-1 | ILCSDSNGKN | RSSARILQII | KGKDYESEPS | LLEFKPFSSG | ALVGGFVYRG | 495 |
| zebrafish HIP-1 | ILCTDTVGKN | TTTGRILQVI | KGKDYENEPS | MFDLGSSGGT | TPVGGFIYRG | 280 |
| Consensus | ILCSDSNGKN | RSSARILQII | KGKDYESEPS | LLEFKPFS.G | .LVGGFVYRG | 500 |
| human HIP-1 | CQSERLYGSY | VFGDRNGNFL | TLQQSPVTKQ | WQEKPLCLGT | SGSCRGYFSG | 549 |
| mouse HIP-1 | CQSERLYGSY | VFGDRNGNFL | TLQQSPVTKQ | WQEKPLCLGA | SSSCRGYFSG | 549 |
| chick HIP-1 | CQSERLYGSY | VFGDRNGNFL | TLQQNPATKQ | WQEKPLCLGN | SGSCRGFFSG | 545 |
| zebrafish HIP-1 | CQSRRLYGSY | VFGDKNGNFR | ILQRPLEDRL | WQEKPLCLGT | SSSCGSSLVG | 330 |
| Consensus | CQSERLYGSY | VFGDRNGNFL | TLQQ.P.TKQ | WQEKPLCLG. | S.SCRG.FSG | 550 |
| human HIP-1 | HILGFGEDEL | GEVYILSSSK | SMTQTHNGKL | YKIVDPKRPL | MPEECRATVQ | 599 |
| mouse HIP-1 | HILGFGEDEL | GEVYILSSSK | SMTQTHNGKL | YKIVDPKRPL | MPEECRVTVQ | 599 |
| chick HIP-1 | PVLGFGEDEL | GEIYILSSSK | SMTQTHNGKL | YKIIDPKRPL | VPEECKRTAR | 595 |
| zebrafish HIP-1 | HILGFGEDEL | GEVYILVSSK | STAKQSHGKI | YKLVDPKRPQ | VPKECRRPVE | 380 |
| Consensus | HILGFGEDEL | GEVYILSSSK | SMTQTHNGKL | YKIVDPKRPL | .PEECR.TV. | 600 |
| human HIP-1 | PAQTLTSECS | RLCRNGYCTP | TGKCCCSPGW | EGDFCRTAKC | EPACRHGGVC | 649 |
| mouse HIP-1 | PAQPLTSDCS | RLCRNGYYTP | TGKCCCSPGW | EGDFCRIAKC | EPACRHGGVC | 649 |
| chick HIP-1 | SAQILTSECS | RHCRNGHCTP | TGKCCCNQGW | EGEFCRTAKC | DPACRHGGVC | 645 |
| zebrafish HIP-1 | DPEMLSTACS | RECKNGHCTP | TGKCCCNAGW | EGPFCLRAKC | ELACRNGGVC | 430 |
| Consensus | .AQ.LTS.CS | R.CRNG.CTP | TGKCCC..GW | EG.FCR.AKC | EPACRHGGVC | 650 |
| human HIP-1 | VRPNKCLCKK | GYLGPQCEQV | DRNIR-RMTR | AGVLDQIFDM | TSYLLDLTNY | 698 |
| mouse HIP-1 | VRPNKCLCKK | GYLGPQCEQV | DRNVR-RVTR | AGILDQIIDM | TSYLLDLTSY | 698 |
| chick HIP-1 | VRPNKCLCKK | GYLGPQCEQV | DRNFR-KVTR | PGILDQILDM | TSYLLDLTSY | 694 |
| zebrafish HIP-1 | VEPNKCLCKE | GFSGNQCSKG | ERGTKGDGEK | DSILEHIIDM | TTYLLDLTSY | 480 |
| Consensus | VRPNKCLCKK | GYLGPQCEQV | DRN.R-..TR | .GILDQI.DM | TSYLLDLTSY | 700 |
| human HIP-1 | IV | | | | | 700 |
| mouse HIP-1 | IV | | | | | 700 |
| chick HIP-1 | IV | | | | | 696 |
| zebrafish HIP-1 | IV | | | | | 482 |
| Consensus | IV | | | | | 702 |

*Figure 1A (con't)*

Hip-1 cDNA

```
human Hip-1        ATGCTGAAGA TGCTCTCCTT TAAGCTGCTG CTGCTGGCCG TGGCTCTGGG    50
mouse Hip-1        ATGCTGAAGA TGCTCTCGTT TAAGCTGCTA CTGCTGGCCG TGGCTCTGGG    50
chick Hip-1        ATGCTCAAGA TGCTGCCGTT CAAGCTGCTG CTGGTGGCCG TGGCTCTGTG    50
zebrafish Hip-1    ---------- ---------- ---------- ---------- ----------
Consensus          ATGCTSAAGA TGCTSYCSTT YAAGCTGCTR CTGSTGGCCG TGGCTCTGKG    50

human Hip-1        CTTCTTTGAA GGAGATGCTA AGTTTGGGGA AAGAAACGAA GGGAGCGGAG   100
mouse Hip-1        CTTCTTTGAA GGAGATGCGA AGTTTGGGGA AAGGAGCGAG GGGAGCGGAG   100
chick Hip-1        CTTCTTCGAG GGGGATGCCA AGTTCGGGGA ---------- --GAGCGGCG    88
zebrafish Hip-1    ---------- ---------- ---------- ---------- ----------
Consensus          CTTCTTYGAR GGRGATGCBA AGTTYGGGGA AAGRARCGAR GGGAGCGGMG   100

human Hip-1        CAAGGAGGAG AAGGTGCCTG AATGGGAACC CCCCGAAGCG CCTGAAAAGG   150
mouse Hip-1        CGAGAAGGAG ACGGTGCCTG AATGGGAACC CCCCAAAGCG CCTAAAGAGA   150
chick Hip-1        CGCGGAGGAG AAGGTGCCTC AACGGGACCC CGCCGCGGCG GCTGAAGAAG   138
zebrafish Hip-1    ---------- ---------- ---------- ---------- ----------
Consensus          CRMGRAGGAG AMGGTGCCTS AAYGGGAMCC CSCCRMRGCG SCTRAARARR   150

human Hip-1        AGAGACAGGA GGATGATGTC CCAGCTGGAG CTGCTGAGTG GGGGAGAGAT   200
mouse Hip-1        AGGGACAGGC GGGTGATGTC CCAGCTGGAG CTGCTCAGTG GAGGAGAGAT   200
chick Hip-1        CGCGACCGGC GGCTGCTGTC C---CCGGAG GCGCCGGGCG GCGCGGAGGC   185
zebrafish Hip-1    ---------- ---------- ---------- ---------- ----------
Consensus          MGVGACMGGM GGVTGMTGTC CCAGCYGGAG SYGCYSRGYG GVGSRGAGRY   200

human Hip-1        GCTGTGCGGT GGCTTCTACC CTCGGCTGTC CTGCTGCCTG CGGAGTGACA   250
mouse Hip-1        CCTGTGTGGT GGCTTCTACC CACGAGTATC TTGCTGCCTG CAGAGTGACA   250
chick Hip-1        GATGTGCCGC GGCCTCTACC CGCGCCTCTC CTGCTGCTCC CGCGCCGACG   235
zebrafish Hip-1    ---------- ---------- ---------- ---------- ----------
Consensus          SMTGTGYSGY GGCYTCTACC CDCGVSTVTC YTGCTGCYYS CRSRSYGACR   250

human Hip-1        GCCCGGGGCT AGGGCGCCTG GAGAATAAGA TATTTTCTGT TACCAACAAC   300
mouse Hip-1        GCCCTGGATT GGGGCGTCTG GAGAACAAGA TCTTTTCTGC CACCAACAAC   300
chick Hip-1        CGCAGGGGTT GCTGCACGCC GGGGCCAAGA TACTTTCTGT CACGAACAAC   285
zebrafish Hip-1    ---------- ---------- ---------- ---------- ----------
Consensus          SSCMKGGRYT RSKGCRYSYS GRGRMYAAGA TMYTTTCTGY YACSAACAAC   300

human Hip-1        ACAGAATGTG GGAAGTTACT GGAGGAAATC AAATGTGCAC TTTGCTCTCC   350
mouse Hip-1        TCAGAATGCA GCAGGCTGCT GGAGGAGATC CAATGTGCTC CCTGCTCCCC   350
chick Hip-1        ACAGAATGTG CGAAGCTACT GGAGGAAATC AAATGCGCAC ACTGCTCACC   335
zebrafish Hip-1    ---------- ---------- ---------- ---------- ----------
Consensus          WCAGAATGYR SSARGYTRCT GGAGGARATC MAATGYGCWC HYTGCTCHCC   350

human Hip-1        ACATTCTCAA AGCCTGTTCC ACTCACCTGA GA---GAGAA GTCTTGGAAA   397
mouse Hip-1        GCATTCCCAG AGCCTCTTCT ACACACCTGA AA---GAGAT GTCCTGGATG   397
chick Hip-1        TCATGCCCAG AATCTTTTCC ACTCACCTGA GAAAGGGGAA ACTTCTGAAA   385
zebrafish Hip-1    ---------- ---------- ---------- ---------- ----------
Consensus          DCATKCYCAR ARYCTBTTCY ACWCACCTGA RAAAGGRGAW RYYYYKGAWR   400
```

*Figure 1B*

Hip-1 cDNA

```
human Hip-1        GAGACATAGT ACTTCCTCTG CTCTGCAAAG ACTATTGCAA AGAATTCTTT   447
mouse Hip-1        GGGACCTAGC ACTTCCGCTC CTCTGCAAAG ACTACTGCAA AGAATTCTTT   447
chick Hip-1        GAGAACTAAC TCTTCCCTAC TTGTGCAAAG ACTATTGTAA AGAATTCTAT   435
zebrafish Hip-1    ---------- ---------- ---------- ---------- ----------
Consensus          GRGAMMTARY WCTTCCBYWS YTSTGCAAAG ACTAYTGYAA AGAATTCTWT   450

human Hip-1        TACACTTGCC GAGGCCATAT TCCAGGTTTC CTTCAAACAA CTGCGGATGA   497
mouse Hip-1        TATACTTGCC GAGGCCATAT TCCAGGTCTT CTTCAAACAA CTGCTGATGA   497
chick Hip-1        TATACTTGCA GAGGTCACTT ACCAGGTTTT CTCCAAACTA CAGCTGATGA   485
zebrafish Hip-1    ---------- ---------- ---------- ---------- ----------
Consensus          TAYACTTGCM GAGGYCAYWT WCCAGGTYTY CTYCAAACWA CWGCKGATGA   500

human Hip-1        GTTTTGCTTT TACTATGCAA GAAAAGATGG TGGGTTGTGC TTTCCAGATT   547
mouse Hip-1        ATTTTGCTTT TACTATGCAA GAAAAGATGC TGGGTTATGC TTTCCAGACT   547
chick Hip-1        GTTTTGCTTT TACTATGCAA GAAAAGATGG TGGTGTATGC TTTCCAGATT   535
zebrafish Hip-1    ---------- ---------- ---------- ---------- ----------
Consensus          RTTTTGCTTT TACTATGCAA GAAAAGATGS TGGKKTRTGC TTTCCAGAYT   550

human Hip-1        TTCCAAGAAA ACAAGTCAGA GGACCAGCAT CTAACTACTT GGACCAGATG   597
mouse Hip-1        TCCCGAGAAA GCAAGTCAGA GGACCAGCAT CTAACTACTT GGGCCAGATG   597
chick Hip-1        TTCCAAGAAA ACAAGTGCGA GGGCCAGCTT CTAACTCCCT GGACCACATG   585
zebrafish Hip-1    ---------- ---------- ---------- ---------- ----------
Consensus          TYCCRAGAAA RCAAGTSMGA GGRCCAGCWT CTAACTMCYT GGRCCASATG   600

human Hip-1        GAAGAATATG ACAAAGTGGA AGAGATCAGC AGAAAGCACA AACACAACTG   647
mouse Hip-1        GAAGACTACG AGAAAGTGGG GGGGATCAGC AGAAAACACA AACACAACTG   647
chick Hip-1        GAGGAATATG ACAAAGAGGA AGAGATCAGC AGAAAGCACA AGCACAACTG   635
zebrafish Hip-1    ---------- ---------- ---------- ---------- ----------
Consensus          GARGAMTAYG ASAAAGWGGR RGRGATCAGC AGAAARCACA ARCACAACTG   650

human Hip-1        CTTCTGTATT CAGGAGGTTG TGAGTGGGCT GCGGCAGCCC GTTGGTGCCC   697
mouse Hip-1        CCTCTGTGTC CAGGAGGTCA TGAGTGGGCT GCGGCAGCCT GTGAGCGCTG   697
chick Hip-1        CTTCTGTATT CAGGAAGTCA TGAGCGGACT AAGGCAGCCT GTTGGAGCGG   685
zebrafish Hip-1    ---------- CAGGAGATCC ATAGTGGTCT TCAACAACCT GTTGGCGTGG    40
Consensus          CYTCTGTRTY CAGGARRTYV WKAGYGGDCT DMRRCARCCY GTKRGHGYBS   700

human Hip-1        TGCATAGTGG GGATGGCTCG CAACGTCTCT TCATTCTGGA AAAAGAAGGT   747
mouse Hip-1        TGCACAGCGG GGATGGCTCC CATCGGCTCT TCATTCTAGA GAAGGAAGGC   747
chick Hip-1        TACATTGTGG GGATGGATCT CATCGCCTCT TTATTCTTGA GAAAGAAGGA   735
zebrafish Hip-1    TGCATTGTGG AGATGGATCG CAGCGGCTTT TTATATTGGA GAGGGAAGGC    90
Consensus          TRCAYWGYGG RGATGGMTCB CADCGBCTYT TYATWYTDGA RARRGAAGGH   750

human Hip-1        TATGTGAAGA TACTTACCCC TGAAGGAGAA ATTTTCAAGG AGCCTTATTT   797
mouse Hip-1        TACGTGAAAA TTCTAACCCC AGAAGGAGAA CTGTTCAAGG AGCCTTACTT   797
chick Hip-1        TATGTGAAGA TTTTCAGTCC TGAAGGAGAC ATGATCAAGG AACCTTTTTT   785
zebrafish Hip-1    TTTGTGTGGA TCCTCACACA TGACATGGAA CTCCTAAAAG AGCCTTTTCT   140
Consensus          TWYGTGWRRA THYTHASHCM WGAMRKRGAM MTBHTMAARG ARCCTTWYYT   800
```

*Figure 1B (con't)*

Hip-1 cDNA

| | | | | | | |
|---|---|---|---|---|---|---|
| human Hip-1 | GGACATTCAC | AAACTTGTTC | AAAGTGGAAT | AAAGGGAGGA | GATGAAAGAG | 847 |
| mouse Hip-1 | GGACATTCAC | AAACTTGTTC | AAAGTGGAAT | AAAGGGAGGA | GACGAAAGGG | 847 |
| chick Hip-1 | GGATATACAC | AAGCTTGTTC | AAAGTGGAAT | AAAGGGAGGA | GATGAAAGAG | 835 |
| zebrafish Hip-1 | GGACATTCAT | AAGCTGGTAC | AAAGTGGTTT | AAAGGGGGGA | GATGAAAGGG | 190 |
| Consensus | GGAYATWCAY | AARCTKGTWC | AAAGTGGWWT | AAAGGGRGGA | GAYGAAAGRG | 850 |

| | | | | | | |
|---|---|---|---|---|---|---|
| human Hip-1 | GACTGCTAAG | CCTCGCATTC | CATCCCAATT | ACAAGAAAAA | TGGAAAGTTG | 897 |
| mouse Hip-1 | GCCTGCTAAG | CCTGGCATTC | CATCCCAATT | ACAAGAAAAA | TGGAAAGCTG | 897 |
| chick Hip-1 | GACTGTTAAG | CCTTGCATTC | CATCCCAATT | ACAAGAAAAA | TGGAAAGCTG | 885 |
| zebrafish Hip-1 | GCTTGCTAAG | CCTTGCATTC | CACCCCAATT | ATAAGAAAAA | TGGCAAGCTC | 240 |
| Consensus | GMYTGYTAAG | CCTBGCATTC | CAYCCCAATT | AYAAGAAAAA | TGGMAAGYTS | 900 |

| | | | | | | |
|---|---|---|---|---|---|---|
| human Hip-1 | TATGTGTCCT | ATACCACCAA | CCAAGAACGG | TGGGCTATCG | GGCCTCATGA | 947 |
| mouse Hip-1 | TATGTGTCTT | ATACCACCAA | CCAGGAACGG | TGGGCTATTG | GGCCTCACGA | 947 |
| chick Hip-1 | TATGTGTCTT | ATACCACCAA | CCAAGAACGG | TGGGCTATTG | GACCTCATGA | 935 |
| zebrafish Hip-1 | TACGTCTCCT | ATACGACCAA | CCAGGAGCGA | TGGACTATTG | GACCACACGA | 290 |
| Consensus | TAYGTSTCYT | ATACSACCAA | CCARGARCGR | TGGRCTATYG | GRCCWCAYGA | 950 |

| | | | | | | |
|---|---|---|---|---|---|---|
| human Hip-1 | CCACATTCTT | AGGGTTGTGG | AATACACAGT | ATCCAGAAAA | AATCCACACC | 997 |
| mouse Hip-1 | CCACATTCTT | CGGGTTGTGG | AATACACAGT | ATCCAGGAAA | AACCCCCATC | 997 |
| chick Hip-1 | TCACATCCTT | AGGGTGGTAG | AATACACAGT | ATCCAGGAAA | AATCCACAAC | 985 |
| zebrafish Hip-1 | CCACATTCTT | CGTGTAGTGG | AGTACACAGT | GTCCAGAAAA | AATCCAAACC | 340 |
| Consensus | YCACATYCTT | MGKGTDGTRG | ARTACACAGT | RTCCAGRAAA | AAYCCMMAHC | 1000 |

| | | | | | | |
|---|---|---|---|---|---|---|
| human Hip-1 | AAGTTGATTT | GAGAACAGCC | AGAATCTTTC | TTGAAGTTGC | AGAACTCCAC | 1047 |
| mouse Hip-1 | AAGTTGATGT | GAGAACAGCC | AGGGTGTTTC | TGGAAGTCGC | AGAGCTCCAC | 1047 |
| chick Hip-1 | AAGTTGATAT | AAGAACAGCC | AGAGTGTTTT | TAGAAGTAGC | AGAACTACAT | 1035 |
| zebrafish Hip-1 | AGGTGGACAC | AAGGACTCCT | CGGGTTTTAA | TGGAAGTTGC | AGAACTTCAC | 390 |
| Consensus | ARGTKGAYDY | RAGRACWSCY | MGRRTBTTWH | TDGAAGTHGC | AGARCTHCAY | 1050 |

| | | | | | | |
|---|---|---|---|---|---|---|
| human Hip-1 | AGAAAGCATC | TGGGAGGACA | ACTGCTCTTT | GGCCCTGACG | GCTTTTTGTA | 1097 |
| mouse Hip-1 | CGAAAGCATC | TTGGGGGACA | GCTGCTCTTT | GGTCCTGATG | GCTTTTTGTA | 1097 |
| chick Hip-1 | CGAAAACATC | TAGGAGGGCA | GCTTCTGTTT | GGCCCAGATG | GTTTCTTATA | 1085 |
| zebrafish Hip-1 | CGAAAGCATC | TGGGAGGCCA | GCTCCTCTTT | GGGCCTGATG | GGCTTCTGCA | 440 |
| Consensus | MGAAARCATC | TDGGRGGVCA | RCTBCTSTTT | GGBCCWGAYG | GBYTYYTRYA | 1100 |

| | | | | | | |
|---|---|---|---|---|---|---|
| human Hip-1 | CATCATTCTT | GGTGATGGGA | TGATTACACT | GGATGATATG | GAAGAAATGG | 1147 |
| mouse Hip-1 | CATCATCCTT | GGGGATGGTA | TGATCACATT | GGATGACATG | GAAGAGATGG | 1147 |
| chick Hip-1 | CGTTTTCCTT | GGAGATGGCA | TGATTACCCT | CGACGATATG | GAAGAAATGG | 1135 |
| zebrafish Hip-1 | CATCTTTTTA | GGAGATGGCA | TGATCACTTT | GGACAATATG | GAGGAGATGG | 490 |
| Consensus | CRTYWTYYTW | GGDGATGGBA | TGATYACHYT | SGAYRAYATG | GARGARATGG | 1150 |

| | | | | | | |
|---|---|---|---|---|---|---|
| human Hip-1 | ATGGGTTAAG | TGATTTCACA | GGCTCAGTGC | TACGGCTGGA | TGTGGACACA | 1197 |
| mouse Hip-1 | ATGGGTTAAG | TGACTTCACA | GGCTCTGTGC | TGAGGCTGGA | CGTGGACACC | 1197 |
| chick Hip-1 | ATGGTTTAAG | CGATTTTACA | GGTTCTGTAT | TACGCCTCGA | TGTAAATACT | 1185 |
| zebrafish Hip-1 | ATGGTCTGAG | TGATTTCACA | GGTTCTGTTC | TTCGGGTGGA | TGTGGACACA | 540 |
| Consensus | ATGGKYTRAG | YGAYTTYACA | GGYTCWGTDY | TDMGSSTSGA | YGTRRAYACH | 1200 |

*Figure 1B (con't)*

Hip-1 cDNA

```
human Hip-1          GACATG-TGC AACGTGCCTT ATTCCATACC AAGGAGCAAC CCACACTTCA   1246
mouse Hip-1          GACATG-TGC AATGTGCCTT ATTCCATACC TCGGAGTAAC CCTCACTTCA   1246
chick Hip-1          GACCTG-TGC AGTGTCCCTT ATTCCATACC ACGGAGCAAC CCACATTTTA   1234
zebrafish Hip-1      GA-ATGTTGT AGTACTCCCT ACTCCATACC CAGAAACAAT CCCTATTTCA    589

Consensus            GACMTGTTGY ARYRYBCCYT AYTCCATACC HMGRARYAAY CCHYAYTTYA   1250

human Hip-1          ACAGCACCAA CCAGCCCCCC GAAGTGTTTG CTCATGGGCT CCACGATCCA   1296
mouse Hip-1          ACAGCACCAA CCAGCCCCCA GAAGTATTTG CCCACGGCCT CCATGATCCA   1296
chick Hip-1          ATAGCACAAA CCAACCTCCT GAAATTTTTG CACACGGACT CCACAATCCA   1284
zebrafish Hip-1      ACAGCACAAA TCAACCCCCC GAAATCTTTG CCCATGGTCT GCATGACCCA    639

Consensus            AYAGCACMAA YCARCCYCCH GAARTNTTTG CHCAYGGNCT SCAYRAYCCA   1300

human Hip-1          GGCAGATGTG CTGTGGATAG ACATCCCACT GATATAAACA TCAATTTAAC   1346
mouse Hip-1          GGCAGATGTG CCGTGGATCG ACATCCTACT GATATAAACA TCAATTTAAC   1346
chick Hip-1          GGCCGATGTG CTGTGGATCA CCACCCAGCA GATGTAAACA TCAATTTAAC   1334
zebrafish Hip-1      GGGAGGTGTG CAGTAGATAA GCTCCGCATG GACACCAATG GGAGTCTGCT    689

Consensus            GGSMGRTGTG CHGTRGATMR VCWYCSHRYD GAYRYMAAYR KSARTYTRMY   1350

human Hip-1          GATACTGTGT TCAGACTCCA ATGG-AAAAA ---------- ----------   1375
mouse Hip-1          AATACTTTGC TCAGATTCCA ACGG-GAAAA ---------- ----------   1375
chick Hip-1          AATACTTTGC TCAGATTCAA ATGG-AAAGA ---------- ----------   1363
zebrafish Hip-1      GATCCTGTGC ACAGATACAG TTGGCAAAAA TACGACAACA GGCAGGATCC    739

Consensus            RATMCTKTGY WCAGAYWCMR WYGGCRAARA TACGACAACA GGCAGGATCC   1400

human Hip-1          -ACAGATCAT CAGCCAGAAT TCTACAGATA ATAAAGGGGA AAGATTATGA   1424
mouse Hip-1          -ACAGGTCAT CAGCCAGAAT CCTACAGATA ATAAAGGGAA GAGATTATGA   1424
chick Hip-1          -ACAGATCTT CAGCAAGAAT CTTACAGATA ATAAAGGGTA AAGACTATGA   1412
zebrafish Hip-1      TACAGGTCAT CA-------- ---------- ---AA-GGGA AAGATTACGA    767

Consensus            TACAGRTCWT CAGCMAGAAT YYTACAGATA ATAAAGGGDA RAGAYTAYGA   1450

human Hip-1          AAGTGAGCCA TCACTTTTAG AATTCAAGCC ATTCAGTAAT GGTCCTTTGG   1474
mouse Hip-1          AAGTGAGCCA TCTCTTCTTG AATTCAAGCC ATTCAGTAAC GGCCCTTTGG   1474
chick Hip-1          AAGTGAGCCT TCACTTTTAG AATTCAAACC ATTCAGCAGT GGAGCGTTGG   1462
zebrafish Hip-1      AAACGAGCCA TCTATGTTTG ACTTGGGGTC AAGCGGAGGT ACCACCCCTG    817

Consensus            AARYGAGCCW TCWMTKYTWG AMTTSRRRYC AWKCRGHRRY RSHVCBYYKG   1500

human Hip-1          TTGGTGGATT TGTATACCGG GGCTGCCAGT CAGAAAGATT GTATGGAAGC   1524
mouse Hip-1          TTGGTGGATT TGTTTACAGA GGCTGTCAGT CTGAAAGATT GTACGGAAGC   1524
chick Hip-1          TCGGTGGATT TGTCTATCGA GGTTGCCAGT CTGAAAGGCT CTACGGAAGT   1512
zebrafish Hip-1      TTGGTGGATT TATCTACAGA GGATGTCAGT CAAGAAGACT TTACGGAAGT    867

Consensus            TYGGTGGATT TRTHTAYMGR GGHTGYCAGT CWRRAAGRYT BTAYGGAAGY   1550

human Hip-1          TACGTGTTTG GAGATCGTAA TGGGAATTTC CTAACTCTCC AGCAAAGTCC   1574
mouse Hip-1          TATGTGTTCG GAGATCGCAA TGGGAATTTC TTAACCCTCC AGCAAAGCCC   1574
chick Hip-1          TATGTATTTG GAGACCGCAA TGGAAATTTT TTAACGCTGC AACAGAATCC   1562
zebrafish Hip-1      TATGTATTTG GAGACAAAAA TGGGAACTTT AGAATTCTCC AGAGGCCTTT    917

Consensus            TAYGTRTTYG GAGAYMRHAA TGGRAAYTTY HKAAYBCTSC ARMRRMVYYY   1600
```

*Figure 1B (con't)*

Hip-1 cDNA

| | | | | | | |
|---|---|---|---|---|---|---|
| human Hip-1 | TG-TGACAAA | GCAGTGGCAA | GAAAAACCAC | TCTGTCTCGG | CACTAGTGGG | 1623 |
| mouse Hip-1 | AG-TGACCAA | GCAATGGCAA | GAAAAGCCGC | TCTGCCTGGG | TGCCAGCAGC | 1623 |
| chick Hip-1 | TG-CAACTAA | ACAGTGGCAA | GAGAAACCCC | TCTGTCTTGG | CAACAGCGGT | 1611 |
| zebrafish Hip-1 | AGAAGACCGA | -TTGTGGCAA | GAGAAGCCTC | TTTGTCTTGG | TACTAGCAGT | 966 |
| Consensus | WGAHRACHRA | RYWRTGGCAA | GARAARCCNC | TYTGYCTBGG | YRMYAGYRGB | 1650 |
| | | | | | | |
| human Hip-1 | TCCTGTAGAG | GCTACTTTTC | CGGTCACATC | TTGGGATTTG | GAGAAGATGA | 1673 |
| mouse Hip-1 | TCCTGTCGAG | GCTACTTTTC | GGGTCACATC | TTGGGATTTG | GAGAAGATGA | 1673 |
| chick Hip-1 | TCATGTAGAG | GTTTCTTTTC | AGGCCCTGTC | TTGGGATTTG | GTGAAGATGA | 1661 |
| zebrafish Hip-1 | TCCTGTGGTT | CCTCGCTGGT | AGGCCACATC | CTGGGGTTTG | GCGAAGATGA | 1016 |
| Consensus | TCMTGTVGWK | SYTHSYTKKY | VGGYCMYRTC | YTGGGRTTTG | GHGAAGATGA | 1700 |
| | | | | | | |
| human Hip-1 | ACTAGGTGAA | GTTTACATTT | TATCAAGCAG | TAAAAGTAT- | GACCCAGACT | 1722 |
| mouse Hip-1 | ATTAGGAGAG | GTTTACATTC | TATCAAGCAG | TAAGAGTAT- | GACCCAGACT | 1722 |
| chick Hip-1 | ACTAGGCGAG | ATTTACATAT | TATCAAGCAG | TAAAAGTAT- | GACACAGACT | 1710 |
| zebrafish Hip-1 | ATTAGGTGAG | GTCTACATCC | TTGTCTCCAG | CAAGAGCACA | GCCAAACAGT | 1066 |
| Consensus | AYTAGGHGAR | RTYTACATHY | TWKYMWSCAG | YAARAGYAYA | GMCMMASAST | 1750 |
| | | | | | | |
| human Hip-1 | CACAATGGAA | AACTCTACAA | AATTGTAGAT | CCCAAAAGAC | CTTTAATGCC | 1772 |
| mouse Hip-1 | CACAATGGAA | AACTCTACAA | GATCGTAGAC | CCCAAAAGAC | CTTTAATGCC | 1772 |
| chick Hip-1 | CACAATGGAA | AACTCTACAA | GATCATTGAC | CCAAAAAGGC | CTTTAGTTCC | 1760 |
| zebrafish Hip-1 | CGC-ATGGAA | AGATCTACAA | GTTGGTGGAC | CCCAAAAGAC | CACAAGTTCC | 1115 |
| Consensus | CRCAATGGAA | ARMTCTACAA | RWTBRTDGAY | CCMAAAAGRC | CWYWARTKCC | 1800 |
| | | | | | | |
| human Hip-1 | TGAGGAATGC | AGAGCCACGG | TACAACCTGC | ACAGACACTG | ACTTCAGAGT | 1822 |
| mouse Hip-1 | TGAGGAATGC | AGAGTCACAG | TTCAACCTGC | CCAGCCACTG | ACCTCCGATT | 1822 |
| chick Hip-1 | TGAAGAATGC | AAAAGAACAG | CTCGGTCGGC | ACAGATACTG | ACATCTGAAT | 1810 |
| zebrafish Hip-1 | TAAGGAGTGC | AGAAGACCAG | TAGAAGATCC | AGAGATGCTA | AGCACTGCTT | 1165 |
| Consensus | TRARGARTGC | ARARBMMCRG | YWSRRBMKSC | MSAGMYRCTR | ASHWCHGMDT | 1850 |
| | | | | | | |
| human Hip-1 | GCTCCAGGCT | CTGTCGAAAC | GGCTACTGCA | CCCCCACGGG | AAAGTGCTGC | 1872 |
| mouse Hip-1 | GCTCCCGGCT | CTGTCGAAAC | GGCTACTACA | CCCCCACTGG | CAAGTGCTGC | 1872 |
| chick Hip-1 | GCTCAAGGCA | CTGCCGGAAT | GGGCACTGCA | CACCCACAGG | AAAATGCTGC | 1860 |
| zebrafish Hip-1 | GTTCACGTGA | ATGCAAGAAC | GGCCACTGTA | CACCAACTGG | CAAGTGCTGC | 1215 |
| Consensus | GYTCMMGKSW | MTGYMRRAAY | GGSYACTRYA | CMCCMACDGG | MAARTGCTGC | 1900 |
| | | | | | | |
| human Hip-1 | TGCAGTCCAG | GCTGGGAGGG | GGACTTCTGC | AGAACTGCAA | AATGTGAGCC | 1922 |
| mouse Hip-1 | TGCAGTCCCG | GCTGGGAGGG | AGACTTCTGC | AGAATTGCCA | AGTGTGAGCC | 1922 |
| chick Hip-1 | TGTAATCAAG | GCTGGGAAGG | AGAGTTCTGC | AGAACTGCAA | AGTGTGACCC | 1910 |
| zebrafish Hip-1 | TGCAATGCAG | GCTGGGAAGG | CCCCTTCTGC | TTACGAGCCA | AGTGTGAACT | 1265 |
| Consensus | TGYARTSMMG | GCTGGGARGG | VSMSTTCTGC | WKAMBWGCMA | ARTGTGAVCY | 1950 |
| | | | | | | |
| human Hip-1 | AGCATGTCGT | CATGGAGGTG | TCTGTGTTAG | ACCGAACAAG | TGCCTCTGTA | 1972 |
| mouse Hip-1 | AGCGTGCCGT | CATGGAGGTG | TCTGTGTCAG | ACCGAACAAG | TGCCTCTGTA | 1972 |
| chick Hip-1 | AGCATGTCGA | CATGGAGGTG | TCTGTGTAAG | GCCTAATAAA | TGCTTATGTA | 1960 |
| zebrafish Hip-1 | GGCTTGTCGC | AATGGCGGGG | TCTGTGTTGA | GCCCAACAAG | TGTCTCTGCA | 1315 |
| Consensus | RGCDTGYCGH | MATGGMGGKG | TCTGTGTHRR | RCCBAAYAAR | TGYYTMTGYA | 2000 |

*Figure 1B (con't)*

Hip-1 cDNA

```
human Hip-1         AAAAAGGATA TCTTGGTCCT CAATGT-GAA CAAGTG-GAC AGAAACATCC   2020
mouse Hip-1         AAAAGGGCTA TCTTGGTCCT CAATGT-GAA CAAGTG-GAC AGGAACGTCC   2020
chick Hip-1         AAAAAGGCTA TCTTGGCCCC CAGTGT-GAA CAAGTG-GAT AGAAACTTCC   2008
zebrafish Hip-1     AGGAAGGTTT TTCTGGCAAC CAGTGCAGTA AAGGAGAGCG AGGGACAAAA   1365

Consensus           ARRARGGHTW TYYTGGYMMY CARTGYAGWA MARGWGAGMB AGRRACDWMM   2050

human Hip-1         GCAGA--ATG ACCAGGGCAG GTGTTCTTGA TCAGATCTTC GACATGACAT   2068
mouse Hip-1         GCAGA--GTG ACCAGGGCAG GTATCCTTGA TCAGATCATT GACATGACGT   2068
chick Hip-1         GAAAA--GTT ACAAGGCCAG GTATTCTTGA TCAGATCCTA GACATGACAT   2056
zebrafish Hip-1     GGGGACGGTG AGAAAGACA- GCATCCTGGA GCACATCATT GACATGACGA   1414

Consensus           GVRRACGRTK ASMARGVCAG GYRTYCTKGA KCASATCHTH GACATGACRW   2100

human Hip-1         CTTACTTGCT GGATCTAACA AATTACATTG TATAG                   2103
mouse Hip-1         CTTACTTGCT GGATCTCACA AGTTACATTG TATAG                   2103
chick Hip-1         CCTACTTGCT GGATCTAACC AGCTATATTG TATAG                   2091
zebrafish Hip-1     CTTACCTGCT GGACCTCACT AGTTATATTG TTTAA                   1449

Consensus           CYTACYTGCT GGAYCTMACH ARYTAYATTG TWTAR                   2135
```

*Figure 1B (con't)*

Scatchard Analysis

Human Multiple Tissue Northern Blot

Mouse Multiple Tissue Northern Blot

```
                             SEQUENCE LISTING


<160> NUMBER OF SEQ ID NOS: 18

<210> SEQ ID NO 1
<211> LENGTH: 2103
<212> TYPE: DNA
<213> ORGANISM: Mus sp.
<220> FEATURE:
<221> NAME/KEY: CDS
<222> LOCATION: (1)..(2100)

<400> SEQUENCE: 1

atg ctg aag atg ctc tcg ttt aag ctg cta ctg ctg gcc gtg gct ctg        48
Met Leu Lys Met Leu Ser Phe Lys Leu Leu Leu Leu Ala Val Ala Leu
  1               5                  10                  15

ggc ttc ttt gaa gga gat gcg aag ttt ggg gaa agg agc gag ggg agc        96
Gly Phe Phe Glu Gly Asp Ala Lys Phe Gly Glu Arg Ser Glu Gly Ser
             20                  25                  30
y
gga gcg aga agg aga cgg tgc ctg aat ggg aac ccc cca aag cgc cta       144
Gly Ala Arg Arg Arg Arg Cys Leu Asn Gly Asn Pro Pro Lys Arg Leu
         35                  40                  45
y
aag aga agg gac agg cgg gtg atg tcc cag ctg gag ctg ctc agt gga       192
Lys Arg Arg Asp Arg Arg Val Met Ser Gln Leu Glu Leu Leu Ser Gly
     50                  55                  60
y
gga gag atc ctg tgt ggt ggc ttc tac cca cga gta tct tgc tgc ctg       240
Gly Glu Ile Leu Cys Gly Gly Phe Tyr Pro Arg Val Ser Cys Cys Leu
 65                  70                  75                  80
y
cag agt gac agc cct gga ttg ggg cgt ctg gag aac aag atc ttt tct       288
Gln Ser Asp Ser Pro Gly Leu Gly Arg Leu Glu Asn Lys Ile Phe Ser
                 85                  90                  95
y
gcc acc aac aac tca gaa tgc agc agg ctg ctg gag gag atc caa tgt       336
Ala Thr Asn Asn Ser Glu Cys Ser Arg Leu Leu Glu Glu Ile Gln Cys
            100                 105                 110
y
gct ccc tgc tcc ccg cat tcc cag agc ctc ttc tac aca cct gaa aga       384
Ala Pro Cys Ser Pro His Ser Gln Ser Leu Phe Tyr Thr Pro Glu Arg
        115                 120                 125
y
gat gtc ctg gat ggg gac cta gca ctt ccg ctc ctc tgc aaa gac tac       432
Asp Val Leu Asp Gly Asp Leu Ala Leu Pro Leu Leu Cys Lys Asp Tyr
    130                 135                 140
y
tgc aaa gaa ttc ttt tat act tgc cga ggc cat att cca ggt ctt ctt       480
Cys Lys Glu Phe Phe Tyr Thr Cys Arg Gly His Ile Pro Gly Leu Leu
145                 150                 155                 160
y
```

-continued

```
caa aca act gct gat gaa ttt tgc ttt tac tat gca aga aaa gat gct      528
Gln Thr Thr Ala Asp Glu Phe Cys Phe Tyr Tyr Ala Arg Lys Asp Ala
                165                 170                 175
y
ggg tta tgc ttt cca gac ttc ccg aga aag caa gtc aga gga cca gca      576
Gly Leu Cys Phe Pro Asp Phe Pro Arg Lys Gln Val Arg Gly Pro Ala
            180                 185                 190
y
tct aac tac ttg ggc cag atg gaa gac tac gag aaa gtg ggg ggg atc      624
Ser Asn Tyr Leu Gly Gln Met Glu Asp Tyr Glu Lys Val Gly Gly Ile
        195                 200                 205
y
agc aga aaa cac aaa cac aac tgc ctc tgt gtc cag gag gtc atg agt      672
Ser Arg Lys His Lys His Asn Cys Leu Cys Val Gln Glu Val Met Ser
    210                 215                 220
y
ggg ctg cgg cag cct gtg agc gct gtg cac agc ggg gat ggc tcc cat      720
Gly Leu Arg Gln Pro Val Ser Ala Val His Ser Gly Asp Gly Ser His
225                 230                 235                 240
y
cgg ctc ttc att cta gag aag gaa ggc tac gtg aaa att cta acc cca      768
Arg Leu Phe Ile Leu Glu Lys Glu Gly Tyr Val Lys Ile Leu Thr Pro
                245                 250                 255
y
gaa gga gaa ctg ttc aag gag cct tac ttg gac att cac aaa ctt gtt      816
Glu Gly Glu Leu Phe Lys Glu Pro Tyr Leu Asp Ile His Lys Leu Val
            260                 265                 270
y
caa agt gga ata aag gga gga gac gaa agg ggc ctg cta agc ctg gca      864
Gln Ser Gly Ile Lys Gly Gly Asp Glu Arg Gly Leu Leu Ser Leu Ala
        275                 280                 285
y
ttc cat ccc aat tac aag aaa aat gga aag ctg tat gtg tct tat acc      912
Phe His Pro Asn Tyr Lys Lys Asn Gly Lys Leu Tyr Val Ser Tyr Thr
    290                 295                 300
y
acc aac cag gaa cgg tgg gct att ggg cct cac gac cac att ctt cgg      960
Thr Asn Gln Glu Arg Trp Ala Ile Gly Pro His Asp His Ile Leu Arg
305                 310                 315                 320

gtt gtg gaa tac aca gta tcc agg aaa aac ccc cat caa gtt gat gtg     1008
Val Val Glu Tyr Thr Val Ser Arg Lys Asn Pro His Gln Val Asp Val
                325                 330                 335

aga aca gcc agg gtg ttt ctg gaa gtc gca gag ctc cac cga aag cat     1056
Arg Thr Ala Arg Val Phe Leu Glu Val Ala Glu Leu His Arg Lys His
            340                 345                 350

ctt ggg gga cag ctg ctc ttt ggt cct gat ggc ttt ttg tac atc atc     1104
Leu Gly Gly Gln Leu Leu Phe Gly Pro Asp Gly Phe Leu Tyr Ile Ile
        355                 360                 365

ctt ggg gat ggt atg atc aca ttg gat gac atg gaa gag atg gat ggg     1152
Leu Gly Asp Gly Met Ile Thr Leu Asp Asp Met Glu Glu Met Asp Gly
    370                 375                 380

tta agt gac ttc aca ggc tct gtg ctg agg ctg gac gtg gac acc gac     1200
Leu Ser Asp Phe Thr Gly Ser Val Leu Arg Leu Asp Val Asp Thr Asp
385                 390                 395                 400

atg tgc aat gtg cct tat tcc ata cct cgg agt aac cct cac ttc aac     1248
Met Cys Asn Val Pro Tyr Ser Ile Pro Arg Ser Asn Pro His Phe Asn
                405                 410                 415

agc acc aac cag ccc cca gaa gta ttt gcc cac ggc ctc cat gat cca     1296
Ser Thr Asn Gln Pro Pro Glu Val Phe Ala His Gly Leu His Asp Pro
            420                 425                 430

ggc aga tgt gcc gtg gat cga cat cct act gat ata aac atc aat tta     1344
Gly Arg Cys Ala Val Asp Arg His Pro Thr Asp Ile Asn Ile Asn Leu
        435                 440                 445

aca ata ctt tgc tca gat tcc aac ggg aaa aac agg tca tca gcc aga     1392
Thr Ile Leu Cys Ser Asp Ser Asn Gly Lys Asn Arg Ser Ser Ala Arg
    450                 455                 460

atc cta cag ata ata aag gga aga gat tat gaa agt gag cca tct ctt     1440
Ile Leu Gln Ile Ile Lys Gly Arg Asp Tyr Glu Ser Glu Pro Ser Leu
465                 470                 475                 480
```

-continued

```
ctt gaa ttc aag cca ttc agt aac ggc cct ttg gtt ggt gga ttt gtt      1488
Leu Glu Phe Lys Pro Phe Ser Asn Gly Pro Leu Val Gly Gly Phe Val
                485                 490                 495

tac aga ggc tgt cag tct gaa aga ttg tac gga agc tat gtg ttc gga      1536
Tyr Arg Gly Cys Gln Ser Glu Arg Leu Tyr Gly Ser Tyr Val Phe Gly
            500                 505                 510

gat cgc aat ggg aat ttc tta acc ctc cag caa agc cca gtg acc aag      1584
Asp Arg Asn Gly Asn Phe Leu Thr Leu Gln Gln Ser Pro Val Thr Lys
        515                 520                 525

caa tgg caa gaa aag ccg ctc tgc ctg ggt gcc agc agc tcc tgt cga      1632
Gln Trp Gln Glu Lys Pro Leu Cys Leu Gly Ala Ser Ser Ser Cys Arg
    530                 535                 540

ggc tac ttt tcg ggt cac atc ttg gga ttt gga gaa gat gaa tta gga      1680
Gly Tyr Phe Ser Gly His Ile Leu Gly Phe Gly Glu Asp Glu Leu Gly
545                 550                 555                 560

gag gtt tac att cta tca agc agt aag agt atg acc cag act cac aat      1728
Glu Val Tyr Ile Leu Ser Ser Ser Lys Ser Met Thr Gln Thr His Asn
                565                 570                 575

gga aaa ctc tac aag atc gta gac ccc aaa aga cct tta atg cct gag      1776
Gly Lys Leu Tyr Lys Ile Val Asp Pro Lys Arg Pro Leu Met Pro Glu
            580                 585                 590

gaa tgc aga gtc aca gtt caa cct gcc cag cca ctg acc tcc gat tgc      1824
Glu Cys Arg Val Thr Val Gln Pro Ala Gln Pro Leu Thr Ser Asp Cys
        595                 600                 605

tcc cgg ctc tgt cga aac ggc tac tac acc ccc act ggc aag tgc tgc      1872
Ser Arg Leu Cys Arg Asn Gly Tyr Tyr Thr Pro Thr Gly Lys Cys Cys
    610                 615                 620

tgc agt ccc ggc tgg gag gga gac ttc tgc aga att gcc aag tgt gag      1920
Cys Ser Pro Gly Trp Glu Gly Asp Phe Cys Arg Ile Ala Lys Cys Glu
625                 630                 635                 640

cca gcg tgc cgt cat gga ggt gtc tgt gtc aga ccg aac aag tgc ctc      1968
Pro Ala Cys Arg His Gly Gly Val Cys Val Arg Pro Asn Lys Cys Leu
                645                 650                 655

tgt aaa aag ggc tat ctt ggt cct caa tgt gaa caa gtg gac agg aac      2016
Cys Lys Lys Gly Tyr Leu Gly Pro Gln Cys Glu Gln Val Asp Arg Asn
            660                 665                 670

gtc cgc aga gtg acc agg gca ggt atc ctt gat cag atc att gac atg      2064
Val Arg Arg Val Thr Arg Ala Gly Ile Leu Asp Gln Ile Ile Asp Met
        675                 680                 685

acg tct tac ttg ctg gat ctc aca agt tac att gta tag                  2103
Thr Ser Tyr Leu Leu Asp Leu Thr Ser Tyr Ile Val
    690                 695                 700


<210> SEQ ID NO 2
<211> LENGTH: 2103
<212> TYPE: DNA
<213> ORGANISM: Homo sapiens
<220> FEATURE:
<221> NAME/KEY: CDS
<222> LOCATION: (1)..(2100)

<400> SEQUENCE: 2

atg ctg aag atg ctc tcc ttt aag ctg ctg ctg ctg gcc gtg gct ctg        48
Met Leu Lys Met Leu Ser Phe Lys Leu Leu Leu Leu Ala Val Ala Leu
  1               5                  10                  15

ggc ttc ttt gaa gga gat gct aag ttt ggg gaa aga aac gaa ggg agc        96
Gly Phe Phe Glu Gly Asp Ala Lys Phe Gly Glu Arg Asn Glu Gly Ser
             20                  25                  30

gga gca agg agg aga agg tgc ctg aat ggg aac ccc ccg aag cgc ctg       144
Gly Ala Arg Arg Arg Arg Cys Leu Asn Gly Asn Pro Pro Lys Arg Leu
         35                  40                  45
```

-continued

```
aaa agg aga gac agg agg atg atg tcc cag ctg gag ctg ctg agt ggg      192
Lys Arg Arg Asp Arg Arg Met Met Ser Gln Leu Glu Leu Leu Ser Gly
     50                  55                  60

gga gag atg ctg tgc ggt ggc ttc tac cct cgg ctg tcc tgc tgc ctg      240
Gly Glu Met Leu Cys Gly Gly Phe Tyr Pro Arg Leu Ser Cys Cys Leu
 65                  70                  75                  80

cgg agt gac agc ccg ggg cta ggg cgc ctg gag aat aag ata ttt tct      288
Arg Ser Asp Ser Pro Gly Leu Gly Arg Leu Glu Asn Lys Ile Phe Ser
                 85                  90                  95

gtt acc aac aac aca gaa tgt ggg aag tta ctg gag gaa atc aaa tgt      336
Val Thr Asn Asn Thr Glu Cys Gly Lys Leu Leu Glu Glu Ile Lys Cys
            100                 105                 110

gca ctt tgc tct cca cat tct caa agc ctg ttc cac tca cct gag aga      384
Ala Leu Cys Ser Pro His Ser Gln Ser Leu Phe His Ser Pro Glu Arg
        115                 120                 125

gaa gtc ttg gaa aga gac ata gta ctt cct ctg ctc tgc aaa gac tat      432
Glu Val Leu Glu Arg Asp Ile Val Leu Pro Leu Leu Cys Lys Asp Tyr
    130                 135                 140

tgc aaa gaa ttc ttt tac act tgc cga ggc cat att cca ggt ttc ctt      480
Cys Lys Glu Phe Phe Tyr Thr Cys Arg Gly His Ile Pro Gly Phe Leu
145                 150                 155                 160

caa aca act gcg gat gag ttt tgc ttt tac tat gca aga aaa gat ggt      528
Gln Thr Thr Ala Asp Glu Phe Cys Phe Tyr Tyr Ala Arg Lys Asp Gly
                165                 170                 175

ggg ttg tgc ttt cca gat ttt cca aga aaa caa gtc aga gga cca gca      576
Gly Leu Cys Phe Pro Asp Phe Pro Arg Lys Gln Val Arg Gly Pro Ala
            180                 185                 190

tct aac tac ttg gac cag atg gaa gaa tat gac aaa gtg gaa gag atc      624
Ser Asn Tyr Leu Asp Gln Met Glu Glu Tyr Asp Lys Val Glu Glu Ile
        195                 200                 205

agc aga aag cac aaa cac aac tgc ttc tgt att cag gag gtt gtg agt      672
Ser Arg Lys His Lys His Asn Cys Phe Cys Ile Gln Glu Val Val Ser
    210                 215                 220

ggg ctg cgg cag ccc gtt ggt gcc ctg cat agt ggg gat ggc tcg caa      720
Gly Leu Arg Gln Pro Val Gly Ala Leu His Ser Gly Asp Gly Ser Gln
225                 230                 235                 240

cgt ctc ttc att ctg gaa aaa gaa ggt tat gtg aag ata ctt acc cct      768
Arg Leu Phe Ile Leu Glu Lys Glu Gly Tyr Val Lys Ile Leu Thr Pro
                245                 250                 255

gaa gga gaa att ttc aag gag cct tat ttg gac att cac aaa ctt gtt      816
Glu Gly Glu Ile Phe Lys Glu Pro Tyr Leu Asp Ile His Lys Leu Val
            260                 265                 270

caa agt gga ata aag gga gga gat gaa aga gga ctg cta agc ctc gca      864
Gln Ser Gly Ile Lys Gly Gly Asp Glu Arg Gly Leu Leu Ser Leu Ala
        275                 280                 285

ttc cat ccc aat tac aag aaa aat gga aag ttg tat gtg tcc tat acc      912
Phe His Pro Asn Tyr Lys Lys Asn Gly Lys Leu Tyr Val Ser Tyr Thr
    290                 295                 300

acc aac caa gaa cgg tgg gct atc ggg cct cat gac cac att ctt agg      960
Thr Asn Gln Glu Arg Trp Ala Ile Gly Pro His Asp His Ile Leu Arg
305                 310                 315                 320

gtt gtg gaa tac aca gta tcc aga aaa aat cca cac caa gtt gat ttg     1008
Val Val Glu Tyr Thr Val Ser Arg Lys Asn Pro His Gln Val Asp Leu
                325                 330                 335

aga aca gcc aga atc ttt ctt gaa gtt gca gaa ctc cac aga aag cat     1056
Arg Thr Ala Arg Ile Phe Leu Glu Val Ala Glu Leu His Arg Lys His
            340                 345                 350

ctg gga gga caa ctg ctc ttt ggc cct gac ggc ttt ttg tac atc att     1104
Leu Gly Gly Gln Leu Leu Phe Gly Pro Asp Gly Phe Leu Tyr Ile Ile
```

-continued

```
        355                 360                 365

ctt ggt gat ggg atg att aca ctg gat gat atg gaa gaa atg gat ggg     1152
Leu Gly Asp Gly Met Ile Thr Leu Asp Asp Met Glu Glu Met Asp Gly
    370                 375                 380

tta agt gat ttc aca ggc tca gtg cta cgg ctg gat gtg gac aca gac     1200
Leu Ser Asp Phe Thr Gly Ser Val Leu Arg Leu Asp Val Asp Thr Asp
385                 390                 395                 400

atg tgc aac gtg cct tat tcc ata cca agg agc aac cca cac ttc aac     1248
Met Cys Asn Val Pro Tyr Ser Ile Pro Arg Ser Asn Pro His Phe Asn
                405                 410                 415

agc acc aac cag ccc ccc gaa gtg ttt gct cat ggg ctc cac gat cca     1296
Ser Thr Asn Gln Pro Pro Glu Val Phe Ala His Gly Leu His Asp Pro
            420                 425                 430

ggc aga tgt gct gtg gat aga cat ccc act gat ata aac atc aat tta     1344
Gly Arg Cys Ala Val Asp Arg His Pro Thr Asp Ile Asn Ile Asn Leu
        435                 440                 445

acg ata ctg tgt tca gac tcc aat gga aaa aac aga tca tca gcc aga     1392
Thr Ile Leu Cys Ser Asp Ser Asn Gly Lys Asn Arg Ser Ser Ala Arg
    450                 455                 460

att cta cag ata ata aag ggg aaa gat tat gaa agt gag cca tca ctt     1440
Ile Leu Gln Ile Ile Lys Gly Lys Asp Tyr Glu Ser Glu Pro Ser Leu
465                 470                 475                 480

tta gaa ttc aag cca ttc agt aat ggt cct ttg gtt ggt gga ttt gta     1488
Leu Glu Phe Lys Pro Phe Ser Asn Gly Pro Leu Val Gly Gly Phe Val
                485                 490                 495

tac cgg ggc tgc cag tca gaa aga ttg tat gga agc tac gtg ttt gga     1536
Tyr Arg Gly Cys Gln Ser Glu Arg Leu Tyr Gly Ser Tyr Val Phe Gly
            500                 505                 510

gat cgt aat ggg aat ttc cta act ctc cag caa agt cct gtg aca aag     1584
Asp Arg Asn Gly Asn Phe Leu Thr Leu Gln Gln Ser Pro Val Thr Lys
        515                 520                 525

cag tgg caa gaa aaa cca ctc tgt ctc ggc act agt ggg tcc tgt aga     1632
Gln Trp Gln Glu Lys Pro Leu Cys Leu Gly Thr Ser Gly Ser Cys Arg
    530                 535                 540

ggc tac ttt tcc ggt cac atc ttg gga ttt gga gaa gat gaa cta ggt     1680
Gly Tyr Phe Ser Gly His Ile Leu Gly Phe Gly Glu Asp Glu Leu Gly
545                 550                 555                 560

gaa gtt tac att tta tca agc agt aaa agt atg acc cag act cac aat     1728
Glu Val Tyr Ile Leu Ser Ser Ser Lys Ser Met Thr Gln Thr His Asn
                565                 570                 575

gga aaa ctc tac aaa att gta gat ccc aaa aga cct tta atg cct gag     1776
Gly Lys Leu Tyr Lys Ile Val Asp Pro Lys Arg Pro Leu Met Pro Glu
            580                 585                 590

gaa tgc aga gcc acg gta caa cct gca cag aca ctg act tca gag tgc     1824
Glu Cys Arg Ala Thr Val Gln Pro Ala Gln Thr Leu Thr Ser Glu Cys
        595                 600                 605

tcc agg ctc tgt cga aac ggc tac tgc acc ccc acg gga aag tgc tgc     1872
Ser Arg Leu Cys Arg Asn Gly Tyr Cys Thr Pro Thr Gly Lys Cys Cys
    610                 615                 620

tgc agt cca ggc tgg gag ggg gac ttc tgc aga act gca aaa tgt gag     1920
Cys Ser Pro Gly Trp Glu Gly Asp Phe Cys Arg Thr Ala Lys Cys Glu
625                 630                 635                 640

cca gca tgt cgt cat gga ggt gtc tgt gtt aga ccg aac aag tgc ctc     1968
Pro Ala Cys Arg His Gly Gly Val Cys Val Arg Pro Asn Lys Cys Leu
                645                 650                 655

tgt aaa aaa gga tat ctt ggt cct caa tgt gaa caa gtg gac aga aac     2016
Cys Lys Lys Gly Tyr Leu Gly Pro Gln Cys Glu Gln Val Asp Arg Asn
            660                 665                 670

atc cgc aga atg acc agg gca ggt gtt ctt gat cag atc ttc gac atg     2064
```

-continued

```
Ile Arg Arg Met Thr Arg Ala Gly Val Leu Asp Gln Ile Phe Asp Met
        675                 680                 685

aca tct tac ttg ctg gat cta aca aat tac att gta tag              2103
Thr Ser Tyr Leu Leu Asp Leu Thr Asn Tyr Ile Val
    690                 695                 700


<210> SEQ ID NO 3
<211> LENGTH: 2091
<212> TYPE: DNA
<213> ORGANISM: Gallus sp.
<220> FEATURE:
<221> NAME/KEY: CDS
<222> LOCATION: (1)..(2088)

<400> SEQUENCE: 3

atg ctc aag atg ctg ccg ttc aag ctg ctg ctg gtg gcc gtg gct ctg       48
Met Leu Lys Met Leu Pro Phe Lys Leu Leu Leu Val Ala Val Ala Leu
  1               5                  10                  15

tgc ttc ttc gag ggg gat gcc aag ttc ggg gag agc ggc gcg cgg agg       96
Cys Phe Phe Glu Gly Asp Ala Lys Phe Gly Glu Ser Gly Ala Arg Arg
             20                  25                  30

aga agg tgc ctc aac ggg acc ccg ccg cgg cgg ctg aag aag cgc gac      144
Arg Arg Cys Leu Asn Gly Thr Pro Pro Arg Arg Leu Lys Lys Arg Asp
         35                  40                  45

cgg cgg ctg ctg tcc ccg gag gcg ccg ggc ggc gcg gag gcg atg tgc      192
Arg Arg Leu Leu Ser Pro Glu Ala Pro Gly Gly Ala Glu Ala Met Cys
     50                  55                  60

cgc ggc ctc tac ccg cgc ctc tcc tgc tgc tcc cgc gcc gac gcg cag      240
Arg Gly Leu Tyr Pro Arg Leu Ser Cys Cys Ser Arg Ala Asp Ala Gln
 65                  70                  75                  80

ggg ttg ctg cac gcc ggg gcc aag ata ctt tct gtc acg aac aac aca      288
Gly Leu Leu His Ala Gly Ala Lys Ile Leu Ser Val Thr Asn Asn Thr
                 85                  90                  95

gaa tgt gcg aag cta ctg gag gaa atc aaa tgc gca cac tgc tca cct      336
Glu Cys Ala Lys Leu Leu Glu Glu Ile Lys Cys Ala His Cys Ser Pro
            100                 105                 110

cat gcc cag aat ctt ttc cac tca cct gag aaa ggg gaa act tct gaa      384
His Ala Gln Asn Leu Phe His Ser Pro Glu Lys Gly Glu Thr Ser Glu
        115                 120                 125

aga gaa cta act ctt ccc tac ttg tgc aaa gac tat tgt aaa gaa ttc      432
Arg Glu Leu Thr Leu Pro Tyr Leu Cys Lys Asp Tyr Cys Lys Glu Phe
    130                 135                 140

tat tat act tgc aga ggt cac tta cca ggt ttt ctc caa act aca gct      480
Tyr Tyr Thr Cys Arg Gly His Leu Pro Gly Phe Leu Gln Thr Thr Ala
145                 150                 155                 160

gat gag ttt tgc ttt tac tat gca aga aaa gat ggt ggt gta tgc ttt      528
Asp Glu Phe Cys Phe Tyr Tyr Ala Arg Lys Asp Gly Gly Val Cys Phe
                165                 170                 175

cca gat ttt cca aga aaa caa gtg cga ggg cca gct tct aac tcc ctg      576
Pro Asp Phe Pro Arg Lys Gln Val Arg Gly Pro Ala Ser Asn Ser Leu
            180                 185                 190

gac cac atg gag gaa tat gac aaa gag gaa gag atc agc aga aag cac      624
Asp His Met Glu Glu Tyr Asp Lys Glu Glu Glu Ile Ser Arg Lys His
        195                 200                 205

aag cac aac tgc ttc tgt att cag gaa gtc atg agc gga cta agg cag      672
Lys His Asn Cys Phe Cys Ile Gln Glu Val Met Ser Gly Leu Arg Gln
    210                 215                 220

cct gtt gga gcg gta cat tgt ggg gat gga tct cat cgc ctc ttt att      720
Pro Val Gly Ala Val His Cys Gly Asp Gly Ser His Arg Leu Phe Ile
225                 230                 235                 240

ctt gag aaa gaa gga tat gtg aag att ttc agt cct gaa gga gac atg      768
```

-continued

```
Leu Glu Lys Glu Gly Tyr Val Lys Ile Phe Ser Pro Glu Gly Asp Met
                245                 250                 255

atc aag gaa cct ttt ttg gat ata cac aag ctt gtt caa agt gga ata      816
Ile Lys Glu Pro Phe Leu Asp Ile His Lys Leu Val Gln Ser Gly Ile
            260                 265                 270

aag gga gga gat gaa aga gga ctg tta agc ctt gca ttc cat ccc aat      864
Lys Gly Gly Asp Glu Arg Gly Leu Leu Ser Leu Ala Phe His Pro Asn
        275                 280                 285

tac aag aaa aat gga aag ctg tat gtg tct tat acc acc aac caa gaa      912
Tyr Lys Lys Asn Gly Lys Leu Tyr Val Ser Tyr Thr Thr Asn Gln Glu
    290                 295                 300

cgg tgg gct att gga cct cat gat cac atc ctt agg gtg gta gaa tac      960
Arg Trp Ala Ile Gly Pro His Asp His Ile Leu Arg Val Val Glu Tyr
305                 310                 315                 320

aca gta tcc agg aaa aat cca caa caa gtt gat ata aga aca gcc aga     1008
Thr Val Ser Arg Lys Asn Pro Gln Gln Val Asp Ile Arg Thr Ala Arg
                325                 330                 335

gtg ttt tta gaa gta gca gaa cta cat cga aaa cat cta gga ggg cag     1056
Val Phe Leu Glu Val Ala Glu Leu His Arg Lys His Leu Gly Gly Gln
            340                 345                 350

ctt ctg ttt ggc cca gat ggt ttc tta tac gtt ttc ctt gga gat ggc     1104
Leu Leu Phe Gly Pro Asp Gly Phe Leu Tyr Val Phe Leu Gly Asp Gly
        355                 360                 365

atg att acc ctc gac gat atg gaa gaa atg gat ggt tta agc gat ttt     1152
Met Ile Thr Leu Asp Asp Met Glu Glu Met Asp Gly Leu Ser Asp Phe
    370                 375                 380

aca ggt tct gta tta cgc ctc gat gta aat act gac ctg tgc agt gtc     1200
Thr Gly Ser Val Leu Arg Leu Asp Val Asn Thr Asp Leu Cys Ser Val
385                 390                 395                 400

cct tat tcc ata cca cgg agc aac cca cat ttt aat agc aca aac caa     1248
Pro Tyr Ser Ile Pro Arg Ser Asn Pro His Phe Asn Ser Thr Asn Gln
                405                 410                 415

cct cct gaa att ttt gca cac gga ctc cac aat cca ggc cga tgt gct     1296
Pro Pro Glu Ile Phe Ala His Gly Leu His Asn Pro Gly Arg Cys Ala
            420                 425                 430

gtg gat cac cac cca gca gat gta aac atc aat tta aca ata ctt tgc     1344
Val Asp His His Pro Ala Asp Val Asn Ile Asn Leu Thr Ile Leu Cys
        435                 440                 445

tca gat tca aat gga aag aac aga tct tca gca aga atc tta cag ata     1392
Ser Asp Ser Asn Gly Lys Asn Arg Ser Ser Ala Arg Ile Leu Gln Ile
    450                 455                 460

ata aag ggt aaa gac tat gaa agt gag cct tca ctt tta gaa ttc aaa     1440
Ile Lys Gly Lys Asp Tyr Glu Ser Glu Pro Ser Leu Leu Glu Phe Lys
465                 470                 475                 480

cca ttc agc agt gga gcg ttg gtc ggt gga ttt gtc tat cga ggt tgc     1488
Pro Phe Ser Ser Gly Ala Leu Val Gly Gly Phe Val Tyr Arg Gly Cys
                485                 490                 495

cag tct gaa agg ctc tac gga agt tat gta ttt gga gac cgc aat gga     1536
Gln Ser Glu Arg Leu Tyr Gly Ser Tyr Val Phe Gly Asp Arg Asn Gly
            500                 505                 510

aat ttt tta acg ctg caa cag aat cct gca act aaa cag tgg caa gag     1584
Asn Phe Leu Thr Leu Gln Gln Asn Pro Ala Thr Lys Gln Trp Gln Glu
        515                 520                 525

aaa ccc ctc tgt ctt ggc aac agc ggt tca tgt aga ggt ttc ttt tca     1632
Lys Pro Leu Cys Leu Gly Asn Ser Gly Ser Cys Arg Gly Phe Phe Ser
    530                 535                 540

ggc cct gtc ttg gga ttt ggt gaa gat gaa cta ggc gag att tac ata     1680
Gly Pro Val Leu Gly Phe Gly Glu Asp Glu Leu Gly Glu Ile Tyr Ile
545                 550                 555                 560
```

-continued

```
tta tca agc agt aaa agt atg aca cag act cac aat gga aaa ctc tac      1728
Leu Ser Ser Ser Lys Ser Met Thr Gln Thr His Asn Gly Lys Leu Tyr
                565                 570                 575

aag atc att gac cca aaa agg cct tta gtt cct gaa gaa tgc aaa aga      1776
Lys Ile Ile Asp Pro Lys Arg Pro Leu Val Pro Glu Glu Cys Lys Arg
            580                 585                 590

aca gct cgg tcg gca cag ata ctg aca tct gaa tgc tca agg cac tgc      1824
Thr Ala Arg Ser Ala Gln Ile Leu Thr Ser Glu Cys Ser Arg His Cys
        595                 600                 605

cgg aat ggg cac tgc aca ccc aca gga aaa tgc tgc tgt aat caa ggc      1872
Arg Asn Gly His Cys Thr Pro Thr Gly Lys Cys Cys Cys Asn Gln Gly
    610                 615                 620

tgg gaa gga gag ttc tgc aga act gca aag tgt gac cca gca tgt cga      1920
Trp Glu Gly Glu Phe Cys Arg Thr Ala Lys Cys Asp Pro Ala Cys Arg
625                 630                 635                 640

cat gga ggt gtc tgt gta agg cct aat aaa tgc tta tgt aaa aaa ggc      1968
His Gly Gly Val Cys Val Arg Pro Asn Lys Cys Leu Cys Lys Lys Gly
                645                 650                 655

tat ctt ggc ccc cag tgt gaa caa gtg gat aga aac ttc cga aaa gtt      2016
Tyr Leu Gly Pro Gln Cys Glu Gln Val Asp Arg Asn Phe Arg Lys Val
            660                 665                 670

aca agg cca ggt att ctt gat cag atc cta gac atg aca tcc tac ttg      2064
Thr Arg Pro Gly Ile Leu Asp Gln Ile Leu Asp Met Thr Ser Tyr Leu
        675                 680                 685

ctg gat cta acc agc tat att gta tag                                  2091
Leu Asp Leu Thr Ser Tyr Ile Val
    690                 695


<210> SEQ ID NO 4
<211> LENGTH: 1449
<212> TYPE: DNA
<213> ORGANISM: Brachydanio rerio
<220> FEATURE:
<221> NAME/KEY: CDS
<222> LOCATION: (1)..(1446)

<400> SEQUENCE: 4

cag gag atc cat agt ggt ctt caa caa cct gtt ggc gtg gtg cat tgt        48
Gln Glu Ile His Ser Gly Leu Gln Gln Pro Val Gly Val Val His Cys
  1               5                  10                  15

gga gat gga tcg cag cgg ctt ttt ata ttg gag agg gaa ggc ttt gtg        96
Gly Asp Gly Ser Gln Arg Leu Phe Ile Leu Glu Arg Glu Gly Phe Val
            20                  25                  30

tgg atc ctc aca cat gac atg gaa ctc cta aaa gag cct ttt ctg gac       144
Trp Ile Leu Thr His Asp Met Glu Leu Leu Lys Glu Pro Phe Leu Asp
        35                  40                  45

att cat aag ctg gta caa agt ggt tta aag ggg gga gat gaa agg ggc       192
Ile His Lys Leu Val Gln Ser Gly Leu Lys Gly Gly Asp Glu Arg Gly
     50                  55                  60

ttg cta agc ctt gca ttc cac ccc aat tat aag aaa aat ggc aag ctc       240
Leu Leu Ser Leu Ala Phe His Pro Asn Tyr Lys Lys Asn Gly Lys Leu
 65                  70                  75                  80

tac gtc tcc tat acg acc aac cag gag cga tgg act att gga cca cac       288
Tyr Val Ser Tyr Thr Thr Asn Gln Glu Arg Trp Thr Ile Gly Pro His
                85                  90                  95

gac cac att ctt cgt gta gtg gag tac aca gtg tcc aga aaa aat cca       336
Asp His Ile Leu Arg Val Val Glu Tyr Thr Val Ser Arg Lys Asn Pro
            100                 105                 110

aac cag gtg gac aca agg act cct cgg gtt tta atg gaa gtt gca gaa       384
Asn Gln Val Asp Thr Arg Thr Pro Arg Val Leu Met Glu Val Ala Glu
        115                 120                 125
```

-continued

```
ctt cac cga aag cat ctg gga ggc cag ctc ctc ttt ggg cct gat ggg      432
Leu His Arg Lys His Leu Gly Gly Gln Leu Leu Phe Gly Pro Asp Gly
    130                 135                 140

ctt ctg cac atc ttt tta gga gat ggc atg atc act ttg gac aat atg      480
Leu Leu His Ile Phe Leu Gly Asp Gly Met Ile Thr Leu Asp Asn Met
145                 150                 155                 160

gag gag atg gat ggt ctg agt gat ttc aca ggt tct gtt ctt cgg gtg      528
Glu Glu Met Asp Gly Leu Ser Asp Phe Thr Gly Ser Val Leu Arg Val
                165                 170                 175

gat gtg gac aca gaa tgt tgt agt act ccc tac tcc ata ccc aga aac      576
Asp Val Asp Thr Glu Cys Cys Ser Thr Pro Tyr Ser Ile Pro Arg Asn
            180                 185                 190

aat ccc tat ttc aac agc aca aat caa ccc ccc gaa atc ttt gcc cat      624
Asn Pro Tyr Phe Asn Ser Thr Asn Gln Pro Pro Glu Ile Phe Ala His
        195                 200                 205

ggt ctg cat gac cca ggg agg tgt gca gta gat aag ctc cgc atg gac      672
Gly Leu His Asp Pro Gly Arg Cys Ala Val Asp Lys Leu Arg Met Asp
    210                 215                 220

acc aat ggg agt ctg ctg atc ctg tgc aca gat aca gtt ggc aaa aat      720
Thr Asn Gly Ser Leu Leu Ile Leu Cys Thr Asp Thr Val Gly Lys Asn
225                 230                 235                 240

acg aca aca ggc agg atc cta cag gtc atc aaa ggg aaa gat tac gaa      768
Thr Thr Thr Gly Arg Ile Leu Gln Val Ile Lys Gly Lys Asp Tyr Glu
                245                 250                 255

aac gag cca tct atg ttt gac ttg ggg tca agc gga ggt acc acc cct      816
Asn Glu Pro Ser Met Phe Asp Leu Gly Ser Ser Gly Gly Thr Thr Pro
            260                 265                 270

gtt ggt gga ttt atc tac aga gga tgt cag tca aga aga ctt tac gga      864
Val Gly Gly Phe Ile Tyr Arg Gly Cys Gln Ser Arg Arg Leu Tyr Gly
        275                 280                 285
agt tat gta ttt gga gac aaa aat ggg aac ttt aga att ctc cag agg      912
Ser Tyr Val Phe Gly Asp Lys Asn Gly Asn Phe Arg Ile Leu Gln Arg
    290                 295                 300

cct tta gaa gac cga ttg tgg caa gag aag cct ctt tgt ctt ggt act      960
Pro Leu Glu Asp Arg Leu Trp Gln Glu Lys Pro Leu Cys Leu Gly Thr
305                 310                 315                 320

agc agt tcc tgt ggt tcc tcg ctg gta ggc cac atc ctg ggg ttt ggc     1008
Ser Ser Ser Cys Gly Ser Ser Leu Val Gly His Ile Leu Gly Phe Gly
                325                 330                 335

gaa gat gaa tta ggt gag gtc tac atc ctt gtc tcc agc aag agc aca     1056
Glu Asp Glu Leu Gly Glu Val Tyr Ile Leu Val Ser Ser Lys Ser Thr
            340                 345                 350

gcc aaa cag tcg cat gga aag atc tac aag ttg gtg gac ccc aaa aga     1104
Ala Lys Gln Ser His Gly Lys Ile Tyr Lys Leu Val Asp Pro Lys Arg
        355                 360                 365

cca caa gtt cct aag gag tgc aga aga cca gta gaa gat cca gag atg     1152
Pro Gln Val Pro Lys Glu Cys Arg Arg Pro Val Glu Asp Pro Glu Met
    370                 375                 380

cta agc act gct tgt tca cgt gaa tgc aag aac ggc cac tgt aca cca     1200
Leu Ser Thr Ala Cys Ser Arg Glu Cys Lys Asn Gly His Cys Thr Pro
385                 390                 395                 400

act ggc aag tgc tgc tgc aat gca ggc tgg gaa ggc ccc ttc tgc tta     1248
Thr Gly Lys Cys Cys Cys Asn Ala Gly Trp Glu Gly Pro Phe Cys Leu
                405                 410                 415

cga gcc aag tgt gaa ctg gct tgt cgc aat ggc ggg gtc tgt gtt gag     1296
Arg Ala Lys Cys Glu Leu Ala Cys Arg Asn Gly Gly Val Cys Val Glu
            420                 425                 430

ccc aac aag tgt ctc tgc aag gaa ggt ttt tct ggc aac cag tgc agt     1344
Pro Asn Lys Cys Leu Cys Lys Glu Gly Phe Ser Gly Asn Gln Cys Ser
        435                 440                 445
```

-continued

```
aaa gga gag cga ggg aca aaa ggg gac ggt gag aaa gac agc atc ctg      1392
Lys Gly Glu Arg Gly Thr Lys Gly Asp Gly Glu Lys Asp Ser Ile Leu
    450                 455                 460

gag cac atc att gac atg acg act tac ctg ctg gac ctc act agt tat      1440
Glu His Ile Ile Asp Met Thr Thr Tyr Leu Leu Asp Leu Thr Ser Tyr
465                 470                 475                 480

att gtt taa                                                          1449
Ile Val


<210> SEQ ID NO 5
<211> LENGTH: 700
<212> TYPE: PRT
<213> ORGANISM: Mus sp.

<400> SEQUENCE: 5

Met Leu Lys Met Leu Ser Phe Lys Leu Leu Leu Leu Ala Val Ala Leu
  1               5                  10                  15

Gly Phe Phe Glu Gly Asp Ala Lys Phe Gly Glu Arg Ser Glu Gly Ser
             20                  25                  30

Gly Ala Arg Arg Arg Arg Cys Leu Asn Gly Asn Pro Pro Lys Arg Leu
         35                  40                  45

Lys Arg Arg Asp Arg Arg Val Met Ser Gln Leu Glu Leu Leu Ser Gly
     50                  55                  60

Gly Glu Ile Leu Cys Gly Gly Phe Tyr Pro Arg Val Ser Cys Cys Leu
 65                  70                  75                  80

Gln Ser Asp Ser Pro Gly Leu Gly Arg Leu Glu Asn Lys Ile Phe Ser
                 85                  90                  95

Ala Thr Asn Asn Ser Glu Cys Ser Arg Leu Leu Glu Glu Ile Gln Cys
            100                 105                 110

Ala Pro Cys Ser Pro His Ser Gln Ser Leu Phe Tyr Thr Pro Glu Arg
        115                 120                 125

Asp Val Leu Asp Gly Asp Leu Ala Leu Pro Leu Leu Cys Lys Asp Tyr
    130                 135                 140

Cys Lys Glu Phe Phe Tyr Thr Cys Arg Gly His Ile Pro Gly Leu Leu
145                 150                 155                 160

Gln Thr Thr Ala Asp Glu Phe Cys Phe Tyr Tyr Ala Arg Lys Asp Ala
                165                 170                 175

Gly Leu Cys Phe Pro Asp Phe Pro Arg Lys Gln Val Arg Gly Pro Ala
            180                 185                 190

Ser Asn Tyr Leu Gly Gln Met Glu Asp Tyr Glu Lys Val Gly Gly Ile
        195                 200                 205

Ser Arg Lys His Lys His Asn Cys Leu Cys Val Gln Glu Val Met Ser
    210                 215                 220

Gly Leu Arg Gln Pro Val Ser Ala Val His Ser Gly Asp Gly Ser His
225                 230                 235                 240

Arg Leu Phe Ile Leu Glu Lys Glu Gly Tyr Val Lys Ile Leu Thr Pro
                245                 250                 255

Glu Gly Glu Leu Phe Lys Glu Pro Tyr Leu Asp Ile His Lys Leu Val
            260                 265                 270

Gln Ser Gly Ile Lys Gly Gly Asp Glu Arg Gly Leu Leu Ser Leu Ala
        275                 280                 285

Phe His Pro Asn Tyr Lys Lys Asn Gly Lys Leu Tyr Val Ser Tyr Thr
    290                 295                 300

Thr Asn Gln Glu Arg Trp Ala Ile Gly Pro His Asp His Ile Leu Arg
305                 310                 315                 320
```

-continued

```
Val Val Glu Tyr Thr Val Ser Arg Lys Asn Pro His Gln Val Asp Val
                325                 330                 335

Arg Thr Ala Arg Val Phe Leu Glu Val Ala Glu Leu His Arg Lys His
            340                 345                 350

Leu Gly Gly Gln Leu Leu Phe Gly Pro Asp Gly Phe Leu Tyr Ile Ile
        355                 360                 365

Leu Gly Asp Gly Met Ile Thr Leu Asp Asp Met Glu Glu Met Asp Gly
    370                 375                 380

Leu Ser Asp Phe Thr Gly Ser Val Leu Arg Leu Asp Val Asp Thr Asp
385                 390                 395                 400

Met Cys Asn Val Pro Tyr Ser Ile Pro Arg Ser Asn Pro His Phe Asn
                405                 410                 415

Ser Thr Asn Gln Pro Pro Glu Val Phe Ala His Gly Leu His Asp Pro
            420                 425                 430

Gly Arg Cys Ala Val Asp Arg His Pro Thr Asp Ile Asn Ile Asn Leu
        435                 440                 445

Thr Ile Leu Cys Ser Asp Ser Asn Gly Lys Asn Arg Ser Ser Ala Arg
    450                 455                 460

Ile Leu Gln Ile Ile Lys Gly Arg Asp Tyr Glu Ser Glu Pro Ser Leu
465                 470                 475                 480

Leu Glu Phe Lys Pro Phe Ser Asn Gly Pro Leu Val Gly Gly Phe Val
                485                 490                 495

Tyr Arg Gly Cys Gln Ser Glu Arg Leu Tyr Gly Ser Tyr Val Phe Gly
            500                 505                 510

Asp Arg Asn Gly Asn Phe Leu Thr Leu Gln Gln Ser Pro Val Thr Lys
        515                 520                 525

Gln Trp Gln Glu Lys Pro Leu Cys Leu Gly Ala Ser Ser Ser Cys Arg
    530                 535                 540

Gly Tyr Phe Ser Gly His Ile Leu Gly Phe Gly Glu Asp Glu Leu Gly
545                 550                 555                 560

Glu Val Tyr Ile Leu Ser Ser Ser Lys Ser Met Thr Gln Thr His Asn
                565                 570                 575

Gly Lys Leu Tyr Lys Ile Val Asp Pro Lys Arg Pro Leu Met Pro Glu
            580                 585                 590

Glu Cys Arg Val Thr Val Gln Pro Ala Gln Pro Leu Thr Ser Asp Cys
        595                 600                 605

Ser Arg Leu Cys Arg Asn Gly Tyr Tyr Thr Pro Thr Gly Lys Cys Cys
    610                 615                 620

Cys Ser Pro Gly Trp Glu Gly Asp Phe Cys Arg Ile Ala Lys Cys Glu
625                 630                 635                 640

Pro Ala Cys Arg His Gly Gly Val Cys Val Arg Pro Asn Lys Cys Leu
                645                 650                 655

Cys Lys Lys Gly Tyr Leu Gly Pro Gln Cys Glu Gln Val Asp Arg Asn
            660                 665                 670

Val Arg Arg Val Thr Arg Ala Gly Ile Leu Asp Gln Ile Ile Asp Met
        675                 680                 685

Thr Ser Tyr Leu Leu Asp Leu Thr Ser Tyr Ile Val
    690                 695                 700
```

<210> SEQ ID NO 6
<211> LENGTH: 700
<212> TYPE: PRT
<213> ORGANISM: Homo sapiens

<400> SEQUENCE: 6

-continued

```
Met Leu Lys Met Leu Ser Phe Lys Leu Leu Leu Leu Ala Val Ala Leu
  1               5                  10                  15

Gly Phe Phe Glu Gly Asp Ala Lys Phe Gly Glu Arg Asn Glu Gly Ser
             20                  25                  30

Gly Ala Arg Arg Arg Arg Cys Leu Asn Gly Asn Pro Pro Lys Arg Leu
         35                  40                  45

Lys Arg Arg Asp Arg Arg Met Met Ser Gln Leu Glu Leu Leu Ser Gly
     50                  55                  60

Gly Glu Met Leu Cys Gly Gly Phe Tyr Pro Arg Leu Ser Cys Cys Leu
 65                  70                  75                  80

Arg Ser Asp Ser Pro Gly Leu Gly Arg Leu Glu Asn Lys Ile Phe Ser
                 85                  90                  95

Val Thr Asn Asn Thr Glu Cys Gly Lys Leu Leu Glu Glu Ile Lys Cys
            100                 105                 110

Ala Leu Cys Ser Pro His Ser Gln Ser Leu Phe His Ser Pro Glu Arg
        115                 120                 125

Glu Val Leu Glu Arg Asp Ile Val Leu Pro Leu Leu Cys Lys Asp Tyr
    130                 135                 140

Cys Lys Glu Phe Phe Tyr Thr Cys Arg Gly His Ile Pro Gly Phe Leu
145                 150                 155                 160

Gln Thr Thr Ala Asp Glu Phe Cys Phe Tyr Tyr Ala Arg Lys Asp Gly
                165                 170                 175

Gly Leu Cys Phe Pro Asp Phe Pro Arg Lys Gln Val Arg Gly Pro Ala
            180                 185                 190

Ser Asn Tyr Leu Asp Gln Met Glu Glu Tyr Asp Lys Val Glu Glu Ile
        195                 200                 205

Ser Arg Lys His Lys His Asn Cys Phe Cys Ile Gln Glu Val Val Ser
    210                 215                 220

Gly Leu Arg Gln Pro Val Gly Ala Leu His Ser Gly Asp Gly Ser Gln
225                 230                 235                 240

Arg Leu Phe Ile Leu Glu Lys Glu Gly Tyr Val Lys Ile Leu Thr Pro
                245                 250                 255

Glu Gly Glu Ile Phe Lys Glu Pro Tyr Leu Asp Ile His Lys Leu Val
            260                 265                 270

Gln Ser Gly Ile Lys Gly Gly Asp Glu Arg Gly Leu Leu Ser Leu Ala
        275                 280                 285

Phe His Pro Asn Tyr Lys Lys Asn Gly Lys Leu Tyr Val Ser Tyr Thr
    290                 295                 300

Thr Asn Gln Glu Arg Trp Ala Ile Gly Pro His Asp His Ile Leu Arg
305                 310                 315                 320

Val Val Glu Tyr Thr Val Ser Arg Lys Asn Pro His Gln Val Asp Leu
                325                 330                 335

Arg Thr Ala Arg Ile Phe Leu Glu Val Ala Glu Leu His Arg Lys His
            340                 345                 350

Leu Gly Gly Gln Leu Leu Phe Gly Pro Asp Gly Phe Leu Tyr Ile Ile
        355                 360                 365

Leu Gly Asp Gly Met Ile Thr Leu Asp Asp Met Glu Glu Met Asp Gly
    370                 375                 380

Leu Ser Asp Phe Thr Gly Ser Val Leu Arg Leu Asp Val Asp Thr Asp
385                 390                 395                 400

Met Cys Asn Val Pro Tyr Ser Ile Pro Arg Ser Asn Pro His Phe Asn
                405                 410                 415
```

-continued

```
Ser Thr Asn Gln Pro Pro Glu Val Phe Ala His Gly Leu His Asp Pro
            420                 425                 430

Gly Arg Cys Ala Val Asp Arg His Pro Thr Asp Ile Asn Ile Asn Leu
        435                 440                 445

Thr Ile Leu Cys Ser Asp Ser Asn Gly Lys Asn Arg Ser Ser Ala Arg
    450                 455                 460

Ile Leu Gln Ile Ile Lys Gly Lys Asp Tyr Glu Ser Glu Pro Ser Leu
465                 470                 475                 480

Leu Glu Phe Lys Pro Phe Ser Asn Gly Pro Leu Val Gly Gly Phe Val
                485                 490                 495

Tyr Arg Gly Cys Gln Ser Glu Arg Leu Tyr Gly Ser Tyr Val Phe Gly
            500                 505                 510

Asp Arg Asn Gly Asn Phe Leu Thr Leu Gln Gln Ser Pro Val Thr Lys
        515                 520                 525

Gln Trp Gln Glu Lys Pro Leu Cys Leu Gly Thr Ser Gly Ser Cys Arg
    530                 535                 540

Gly Tyr Phe Ser Gly His Ile Leu Gly Phe Gly Glu Asp Glu Leu Gly
545                 550                 555                 560

Glu Val Tyr Ile Leu Ser Ser Ser Lys Ser Met Thr Gln Thr His Asn
                565                 570                 575

Gly Lys Leu Tyr Lys Ile Val Asp Pro Lys Arg Pro Leu Met Pro Glu
            580                 585                 590

Glu Cys Arg Ala Thr Val Gln Pro Ala Gln Thr Leu Thr Ser Glu Cys
        595                 600                 605

Ser Arg Leu Cys Arg Asn Gly Tyr Cys Thr Pro Thr Gly Lys Cys Cys
    610                 615                 620

Cys Ser Pro Gly Trp Glu Gly Asp Phe Cys Arg Thr Ala Lys Cys Glu
625                 630                 635                 640

Pro Ala Cys Arg His Gly Gly Val Cys Val Arg Pro Asn Lys Cys Leu
                645                 650                 655

Cys Lys Lys Gly Tyr Leu Gly Pro Gln Cys Glu Gln Val Asp Arg Asn
            660                 665                 670

Ile Arg Arg Met Thr Arg Ala Gly Val Leu Asp Gln Ile Phe Asp Met
        675                 680                 685

Thr Ser Tyr Leu Leu Asp Leu Thr Asn Tyr Ile Val
    690                 695                 700


<210> SEQ ID NO 7
<211> LENGTH: 696
<212> TYPE: PRT
<213> ORGANISM: Gallus sp.

<400> SEQUENCE: 7

Met Leu Lys Met Leu Pro Phe Lys Leu Leu Leu Val Ala Val Ala Leu
  1               5                  10                  15

Cys Phe Phe Glu Gly Asp Ala Lys Phe Gly Glu Ser Gly Ala Arg Arg
             20                  25                  30

Arg Arg Cys Leu Asn Gly Thr Pro Pro Arg Arg Leu Lys Lys Arg Asp
         35                  40                  45

Arg Arg Leu Leu Ser Pro Glu Ala Pro Gly Gly Ala Glu Ala Met Cys
     50                  55                  60

Arg Gly Leu Tyr Pro Arg Leu Ser Cys Cys Ser Arg Ala Asp Ala Gln
 65                  70                  75                  80

Gly Leu Leu His Ala Gly Ala Lys Ile Leu Ser Val Thr Asn Asn Thr
                 85                  90                  95
```

-continued

```
Glu Cys Ala Lys Leu Leu Glu Glu Ile Lys Cys Ala His Cys Ser Pro
            100                 105                 110

His Ala Gln Asn Leu Phe His Ser Pro Glu Lys Gly Glu Thr Ser Glu
        115                 120                 125

Arg Glu Leu Thr Leu Pro Tyr Leu Cys Lys Asp Tyr Cys Lys Glu Phe
    130                 135                 140

Tyr Tyr Thr Cys Arg Gly His Leu Pro Gly Phe Leu Gln Thr Thr Ala
145                 150                 155                 160

Asp Glu Phe Cys Phe Tyr Tyr Ala Arg Lys Asp Gly Gly Val Cys Phe
                165                 170                 175

Pro Asp Phe Pro Arg Lys Gln Val Arg Gly Pro Ala Ser Asn Ser Leu
            180                 185                 190

Asp His Met Glu Glu Tyr Asp Lys Glu Glu Glu Ile Ser Arg Lys His
        195                 200                 205

Lys His Asn Cys Phe Cys Ile Gln Glu Val Met Ser Gly Leu Arg Gln
    210                 215                 220

Pro Val Gly Ala Val His Cys Gly Asp Gly Ser His Arg Leu Phe Ile
225                 230                 235                 240

Leu Glu Lys Glu Gly Tyr Val Lys Ile Phe Ser Pro Glu Gly Asp Met
                245                 250                 255

Ile Lys Glu Pro Phe Leu Asp Ile His Lys Leu Val Gln Ser Gly Ile
            260                 265                 270

Lys Gly Gly Asp Glu Arg Gly Leu Leu Ser Leu Ala Phe His Pro Asn
        275                 280                 285

Tyr Lys Lys Asn Gly Lys Leu Tyr Val Ser Tyr Thr Thr Asn Gln Glu
    290                 295                 300

Arg Trp Ala Ile Gly Pro His Asp His Ile Leu Arg Val Val Glu Tyr
305                 310                 315                 320

Thr Val Ser Arg Lys Asn Pro Gln Gln Val Asp Ile Arg Thr Ala Arg
                325                 330                 335

Val Phe Leu Glu Val Ala Glu Leu His Arg Lys His Leu Gly Gly Gln
            340                 345                 350

Leu Leu Phe Gly Pro Asp Gly Phe Leu Tyr Val Phe Leu Gly Asp Gly
        355                 360                 365

Met Ile Thr Leu Asp Asp Met Glu Glu Met Asp Gly Leu Ser Asp Phe
    370                 375                 380

Thr Gly Ser Val Leu Arg Leu Asp Val Asn Thr Asp Leu Cys Ser Val
385                 390                 395                 400

Pro Tyr Ser Ile Pro Arg Ser Asn Pro His Phe Asn Ser Thr Asn Gln
                405                 410                 415

Pro Pro Glu Ile Phe Ala His Gly Leu His Asn Pro Gly Arg Cys Ala
            420                 425                 430

Val Asp His His Pro Ala Asp Val Asn Ile Asn Leu Thr Ile Leu Cys
        435                 440                 445

Ser Asp Ser Asn Gly Lys Asn Arg Ser Ser Ala Arg Ile Leu Gln Ile
    450                 455                 460

Ile Lys Gly Lys Asp Tyr Glu Ser Glu Pro Ser Leu Leu Glu Phe Lys
465                 470                 475                 480

Pro Phe Ser Ser Gly Ala Leu Val Gly Gly Phe Val Tyr Arg Gly Cys
                485                 490                 495

Gln Ser Glu Arg Leu Tyr Gly Ser Tyr Val Phe Gly Asp Arg Asn Gly
            500                 505                 510
```

-continued

```
Asn Phe Leu Thr Leu Gln Gln Asn Pro Ala Thr Lys Gln Trp Gln Glu
        515                 520                 525

Lys Pro Leu Cys Leu Gly Asn Ser Gly Ser Cys Arg Gly Phe Phe Ser
    530                 535                 540

Gly Pro Val Leu Gly Phe Gly Glu Asp Glu Leu Gly Glu Ile Tyr Ile
545                 550                 555                 560

Leu Ser Ser Ser Lys Ser Met Thr Gln Thr His Asn Gly Lys Leu Tyr
                565                 570                 575

Lys Ile Ile Asp Pro Lys Arg Pro Leu Val Pro Glu Glu Cys Lys Arg
            580                 585                 590

Thr Ala Arg Ser Ala Gln Ile Leu Thr Ser Glu Cys Ser Arg His Cys
        595                 600                 605

Arg Asn Gly His Cys Thr Pro Thr Gly Lys Cys Cys Cys Asn Gln Gly
    610                 615                 620

Trp Glu Gly Glu Phe Cys Arg Thr Ala Lys Cys Asp Pro Ala Cys Arg
625                 630                 635                 640

His Gly Gly Val Cys Val Arg Pro Asn Lys Cys Leu Cys Lys Lys Gly
                645                 650                 655

Tyr Leu Gly Pro Gln Cys Glu Gln Val Asp Arg Asn Phe Arg Lys Val
            660                 665                 670

Thr Arg Pro Gly Ile Leu Asp Gln Ile Leu Asp Met Thr Ser Tyr Leu
        675                 680                 685

Leu Asp Leu Thr Ser Tyr Ile Val
    690                 695


<210> SEQ ID NO 8
<211> LENGTH: 482
<212> TYPE: PRT
<213> ORGANISM: Brachydanio rerio

<400> SEQUENCE: 8

Gln Glu Ile His Ser Gly Leu Gln Gln Pro Val Gly Val Val His Cys
  1               5                  10                  15

Gly Asp Gly Ser Gln Arg Leu Phe Ile Leu Glu Arg Glu Gly Phe Val
            20                  25                  30

Trp Ile Leu Thr His Asp Met Glu Leu Leu Lys Glu Pro Phe Leu Asp
        35                  40                  45

Ile His Lys Leu Val Gln Ser Gly Leu Lys Gly Gly Asp Glu Arg Gly
     50                  55                  60

Leu Leu Ser Leu Ala Phe His Pro Asn Tyr Lys Lys Asn Gly Lys Leu
 65                  70                  75                  80

Tyr Val Ser Tyr Thr Thr Asn Gln Glu Arg Trp Thr Ile Gly Pro His
                85                  90                  95

Asp His Ile Leu Arg Val Val Glu Tyr Thr Val Ser Arg Lys Asn Pro
            100                 105                 110

Asn Gln Val Asp Thr Arg Thr Pro Arg Val Leu Met Glu Val Ala Glu
        115                 120                 125

Leu His Arg Lys His Leu Gly Gly Gln Leu Leu Phe Gly Pro Asp Gly
    130                 135                 140

Leu Leu His Ile Phe Leu Gly Asp Gly Met Ile Thr Leu Asp Asn Met
145                 150                 155                 160

Glu Glu Met Asp Gly Leu Ser Asp Phe Thr Gly Ser Val Leu Arg Val
                165                 170                 175

Asp Val Asp Thr Glu Cys Cys Ser Thr Pro Tyr Ser Ile Pro Arg Asn
            180                 185                 190
```

-continued

```
Asn Pro Tyr Phe Asn Ser Thr Asn Gln Pro Pro Glu Ile Phe Ala His
        195                 200                 205

Gly Leu His Asp Pro Gly Arg Cys Ala Val Asp Lys Leu Arg Met Asp
    210                 215                 220

Thr Asn Gly Ser Leu Leu Ile Leu Cys Thr Asp Thr Val Gly Lys Asn
225                 230                 235                 240

Thr Thr Thr Gly Arg Ile Leu Gln Val Ile Lys Gly Lys Asp Tyr Glu
                245                 250                 255

Asn Glu Pro Ser Met Phe Asp Leu Gly Ser Ser Gly Gly Thr Thr Pro
            260                 265                 270

Val Gly Gly Phe Ile Tyr Arg Gly Cys Gln Ser Arg Arg Leu Tyr Gly
        275                 280                 285

Ser Tyr Val Phe Gly Asp Lys Asn Gly Asn Phe Arg Ile Leu Gln Arg
    290                 295                 300

Pro Leu Glu Asp Arg Leu Trp Gln Glu Lys Pro Leu Cys Leu Gly Thr
305                 310                 315                 320

Ser Ser Ser Cys Gly Ser Ser Leu Val Gly His Ile Leu Gly Phe Gly
                325                 330                 335

Glu Asp Glu Leu Gly Glu Val Tyr Ile Leu Val Ser Ser Lys Ser Thr
            340                 345                 350

Ala Lys Gln Ser His Gly Lys Ile Tyr Lys Leu Val Asp Pro Lys Arg
        355                 360                 365

Pro Gln Val Pro Lys Glu Cys Arg Arg Pro Val Glu Asp Pro Glu Met
    370                 375                 380

Leu Ser Thr Ala Cys Ser Arg Glu Cys Lys Asn Gly His Cys Thr Pro
385                 390                 395                 400

Thr Gly Lys Cys Cys Cys Asn Ala Gly Trp Glu Gly Pro Phe Cys Leu
                405                 410                 415

Arg Ala Lys Cys Glu Leu Ala Cys Arg Asn Gly Gly Val Cys Val Glu
            420                 425                 430

Pro Asn Lys Cys Leu Cys Lys Glu Gly Phe Ser Gly Asn Gln Cys Ser
        435                 440                 445

Lys Gly Glu Arg Gly Thr Lys Gly Asp Gly Glu Lys Asp Ser Ile Leu
    450                 455                 460

Glu His Ile Ile Asp Met Thr Thr Tyr Leu Leu Asp Leu Thr Ser Tyr
465                 470                 475                 480

Ile Val
```

```
<210> SEQ ID NO 9
<211> LENGTH: 444
<212> TYPE: DNA
<213> ORGANISM: Homo sapiens

<400> SEQUENCE: 9

atgctgaaga tgctctcgtt taagctgctg ctgctggccg tggctctggg cttctttgaa      60

ggagatgcta agtttgggga aagaaacgaa gggagcggag caaggaggag aaggtgcctg     120

aatgggaacc ccccgaagcg cctgaaaagg agagacagga ggatgatgtc ccagctggag     180

ctgctgagtg gggagagat gctgtgcggt ggcttctacc ctcggctgtc ctgctgcctg     240

cggagtgaca gcccggggct agggcgcctg gagaataaga tattttctgt taccaacaac     300

acagaatgtg ggaagttact ggaggaaatc aaatgtgcac tttgctctcc acattctcaa     360

agcctgttcc actcacctga gagagaagtc ttggaaagag acatagtact tcctctgctc     420
```

-continued

```
tgcaaagact attgcaaaga attc                                           444

<210> SEQ ID NO 10
<211> LENGTH: 958
<212> TYPE: DNA
<213> ORGANISM: Homo sapiens

<400> SEQUENCE: 10

gaattctttt acacttgccg aggccatatt ccaggtttcc ttcaaacaac tgcggatgag     60

ttttgctttt actatgcaag aaaagatggt gggttgtgct ttccagattt tccaagaaaa    120

caagtcagag gaccagcatc taactacttg gaccagatgg aagaatatga caaagtggaa    180

gagatcagca gaaagcacaa acacaactgc ttctgtattc aggaggttgt gagtgggctg    240

cggcagcccg ttggtgccct gcatagtggg gatggctcgc aacgtctctt cattctggaa    300

aaagaaggtt atgtgaagat acttacccct gaaggagaaa ttttcaagga gccttatttg    360

gacattcaca aacttgttca aagtggaata aagggaggag atgaaagagg actgctaagc    420

ctcgcattcc atcccaatta caagaaaaat ggaaagttgt atgtgtccta taccaccaac    480

caagaacggt gggctatcgg gcctcatgac cacattctta gggttgtgga atacacagta    540

tccagaaaaa atccacacca agttgatttg agaacagcca gaatctttct tgaagttgca    600

gaactccaca gaaagcatct gggaggacaa ctgctctttg gccctgacgg ctttttgtac    660

atcattcttg gtgatgggat gattacactg gatgatatgg aagaaatgga tgggttaagt    720

gatttcacag gctcagtgct acggctggat gtggacacag acatgtgcaa cgtgccttat    780

tccataccaa ggagcaaccc acacttcaac agcaccaacc agcccccga agtgtttgct     840

catgggctcc acgatccagg cagatgtgct gtggatagac atcccactga tataaacatc    900

aatttaacga tactgtgttc agactccaat ggaaaaaaca gatcatcagc cagaattc      958

<210> SEQ ID NO 11
<211> LENGTH: 597
<212> TYPE: DNA
<213> ORGANISM: Homo sapiens

<400> SEQUENCE: 11

gaattcaagc cattcagtaa tggtcctttg gttggtggat ttgtataccg ggctgccag      60

tcagaaagat tgtatggaag ctacgtgttt ggagatcgta atgggaattt cctaactctc    120

cagcaaagtc ctgtgacaaa gcagtggcaa gaaaaaccac tctgtctcgg cactagtggg    180

tcctgtagag gctacttttc cggtcacatc ttgggatttg gagaagatga actaggtgaa    240

gtttacattt tatcaagcag taaaagtatg acccagactc acaatggaaa actctacaaa    300

attgtagatc ccaaaagacc tttaatgcct gaggaatgca gagccacggt acaacctgca    360

cagacactga cttcagagtg ctccaggctc tgtcgaaacg gctactgcac ccccacggga    420

aagtgctgct gcagtccagg ctgggagggg gacttctgca gaactgcaaa atgtgagcca    480

gcatgtcgtc atggaggtgt ctgtgttaga ccgaacaagt gcctctgtaa aaaaggatat    540

cttggtcctc aatgtgaaca agtggacaga aacatccgca gagtgaccag ggcaggt       597

<210> SEQ ID NO 12
<211> LENGTH: 426
<212> TYPE: DNA
<213> ORGANISM: Mus sp.

<400> SEQUENCE: 12

atgctcaaga tgctgccgtt caagctgctg ctggtggccg tggctctgtg cttcttcgag     60
```

-continued

```
ggggatgcca agttcgggga gagcggcgcg cggaggagaa ggtgcctcaa cgggaccccc    120

gcggcggctg aagaagcgcg accggcggct gctgtccccg gaccgggcgg cgcggaggcg    180

atgtgccgcg gcctctaccc gcgcctctcc tgctgctccc cggccgacgc gcaggggttg    240

ctgcacgccg gggccaagat actttctgtc acgaacaaca cagaatgtgc gaagctactg    300

gaggaaatca aatgcgcaca ctgctcacct catgcccaga atcttttcca ctcacctgag    360

aaaggggaaa cttctgaaag agaactaact cttccctact tgtgcaaaga ctattgtaaa    420

gaattc                                                               426
```

<210> SEQ ID NO 13
<211> LENGTH: 1011
<212> TYPE: DNA
<213> ORGANISM: Mus sp.

<400> SEQUENCE: 13

```
gaattctatt atacttgcag aggtcactta ccaggttttc tccaaactac agctgatgag     60

ttttgctttt actatgcaag aaaagatggt ggtgtatgct ttccagattt tccaagaaaa    120

caagtgcgag ggccagcttc taactccctg gaccacatgg aggaatatga caaagaggaa    180

gagatcagca gaaagcacaa gcacaactgc ttctgtattc aggaagtcat gagcggacta    240

aggcagcctg ttggagcggt acattgtggg gatggatctc atcgcctctt tattcttgag    300

aaagaaggat atgtgaagat tttcagtcct gaaggagaca tgatcaagga acctttttttg    360

gatatacaca agcttgttca aagtggaata aagggaggag atgaaagagg actgttaagc    420

cttgcattcc atcccaatta caagaaaaat ggaaagctgt atgtgtctta taccaccaac    480

caagaacggt gggctattgg acctcatgat cacatcctta gggtggtaga atacacagta    540

tccaggaaaa atccacaaca agttgatata agaacagcca gagtgttttt agaagtagca    600

gaactacatc gaaaacatct aggagggcag cttctgtttg gcccagatgg tttcttatac    660

gttttccttg gagatggcat gattaccctc gacgatatgg aagaaatgga tggtttaagc    720

gattttacag gttctgtatt acgcctcgat gtaaatactg acctgtgcag tgtcccttat    780

tccataccac ggagcaaccc acattttaat agcacaaacc aacctcctga aatttttgca    840

cacggactcc acaatccagg ccgatgtgct gtggatcacc acccagcaga tgtaaacatc    900

aatttaacaa tactttgctc agattcaaat ggaaagaaca gatcttcagc aagaatctta    960

cagataataa agggtaaaga ctatgaaagt gagccttcac ttttagaatt c            1011
```

<210> SEQ ID NO 14
<211> LENGTH: 660
<212> TYPE: DNA
<213> ORGANISM: Mus sp.

<400> SEQUENCE: 14

```
gaattcaaac cattcagcag tggagcgttg gtcggtggat ttgtctatcg aggttgccag     60

tctgaaaggc tctacggaag ttatgtattt ggagaccgca atggaaattt tttaacgctg    120

caacagaatc ctgcaactaa acagtggcaa gagaaacccc tctgtcttgg caacagcggt    180

tcatgtagag gtttcttttc aggccctgtc ttgggatttg gtgaagatga actaggcgag    240

atttacatat tatcaagcag taaaagtatg acacagactc acaatggaaa actctacaag    300

atcattgacc caaaaaggcc tttagttcct gaagaatgca aaagaacagc tcggtcggca    360

cagatactga catctgaatg ctcaaggcac tgccggaatg ggcactgcac acccacagga    420
```

-continued

```
aaatgctgct gtaatcaagg ctgggaagga gagttctgca gaactgcaaa gtgtgaccca    480

gcatgtcgac atggaggtgt ctgtgtaagg cctaataaat gcttatgtaa aaaaggctat    540

cttggccccc agtgtgaaca attggattta aacttccgaa aagttacaag gccaggtatt    600

cttgatcaga tcctaaacat gacatcctac ttgctggatc taaccagcta tattgtatag    660


<210> SEQ ID NO 15
<211> LENGTH: 656
<212> TYPE: PRT
<213> ORGANISM: Artificial Sequence
<220> FEATURE:
<223> OTHER INFORMATION: Description of Artificial Sequence: Formula
      sequence
<220> FEATURE:
<221> NAME/KEY: MOD_RES
<222> LOCATION: (1)..(656)
<223> OTHER INFORMATION: Xaa may be any natural amino acid

<400> SEQUENCE: 15

Leu Xaa Phe Phe Glu Gly Asp Ala Lys Phe Gly Glu Xaa Xaa Xaa Xaa
  1               5                  10                  15

Ser Gly Ala Arg Arg Arg Arg Cys Leu Asn Gly Xaa Pro Xaa Xaa Xaa
             20                  25                  30

Xaa Xaa Xaa Arg Xaa Arg Xaa Xaa Xaa Xaa Xaa Xaa Xaa Xaa Xaa Xaa
         35                  40                  45

Gly Gly Xaa Xaa Xaa Xaa Xaa Cys Xaa Gly Xaa Tyr Pro Arg Xaa Ser
     50                  55                  60

Cys Cys Xaa Xaa Xaa Asp Xaa Xaa Gly Leu Xaa Xaa Xaa Xaa Xaa Lys
 65                  70                  75                  80

Ile Xaa Ser Xaa Thr Asn Asn Xaa Glu Cys Xaa Xaa Leu Leu Glu Glu
                 85                  90                  95

Ile Xaa Cys Ala Xaa Cys Ser Pro His Xaa Gln Xaa Leu Phe Xaa Thr
            100                 105                 110

Pro Glu Xaa Xaa Xaa Xaa Xaa Xaa Xaa Xaa Xaa Xaa Leu Pro Xaa Leu
        115                 120                 125

Cys Lys Asp Tyr Cys Lys Glu Phe Phe Tyr Thr Cys Arg Gly His Ile
    130                 135                 140

Pro Gly Xaa Leu Gln Thr Thr Ala Asp Glu Phe Cys Phe Tyr Tyr Ala
145                 150                 155                 160

Arg Lys Asp Xaa Gly Leu Cys Phe Pro Asp Phe Pro Arg Lys Gln Val
                165                 170                 175

Arg Gly Pro Ala Ser Asn Tyr Leu Xaa Xaa Met Glu Xaa Tyr Xaa Lys
            180                 185                 190

Xaa Xaa Xaa Ile Ser Arg Lys His Lys His Asn Cys Xaa Cys Xaa Gln
        195                 200                 205

Glu Val Xaa Ser Gly Leu Arg Gln Pro Val Xaa Ala Xaa His Xaa Gly
    210                 215                 220

Asp Gly Xaa Xaa Arg Leu Phe Ile Leu Glu Lys Glu Gly Tyr Val Lys
225                 230                 235                 240

Ile Xaa Xaa Pro Glu Gly Xaa Xaa Xaa Lys Glu Pro Xaa Leu Asp Ile
                245                 250                 255

His Lys Leu Val Gln Ser Gly Ile Lys Gly Gly Asp Glu Arg Gly Leu
            260                 265                 270

Leu Ser Leu Ala Phe His Pro Asn Tyr Lys Lys Asn Gly Lys Leu Tyr
        275                 280                 285

Val Ser Tyr Thr Thr Asn Gln Glu Arg Trp Ala Ile Gly Pro His Asp
    290                 295                 300
```

-continued

```
His Ile Leu Arg Val Val Glu Tyr Thr Val Ser Arg Lys Asn Pro Xaa
305                 310                 315                 320

Gln Val Asp Xaa Arg Thr Ala Arg Xaa Phe Leu Glu Val Ala Glu Leu
                325                 330                 335

His Arg Lys His Leu Gly Gly Gln Leu Leu Phe Gly Pro Asp Gly Phe
            340                 345                 350

Leu Tyr Xaa Xaa Leu Gly Asp Gly Met Ile Thr Leu Asp Asp Met Glu
        355                 360                 365

Glu Met Asp Gly Leu Ser Asp Phe Thr Gly Ser Val Leu Arg Leu Asp
    370                 375                 380

Val Xaa Thr Asp Xaa Cys Xaa Val Pro Tyr Ser Ile Pro Arg Ser Asn
385                 390                 395                 400

Pro His Phe Asn Ser Thr Asn Gln Pro Pro Glu Xaa Phe Ala His Gly
                405                 410                 415

Leu His Xaa Pro Gly Arg Cys Ala Val Asp Xaa His Pro Thr Asp Xaa
            420                 425                 430

Asn Ile Asn Leu Thr Ile Leu Cys Ser Asp Ser Asn Gly Lys Asn Arg
        435                 440                 445

Ser Ser Ala Arg Ile Leu Gln Ile Ile Lys Gly Arg Asp Tyr Glu Ser
    450                 455                 460

Glu Pro Ser Leu Leu Glu Phe Lys Pro Phe Ser Xaa Gly Xaa Leu Val
465                 470                 475                 480

Gly Gly Phe Val Tyr Arg Gly Cys Gln Ser Glu Arg Leu Tyr Gly Ser
                485                 490                 495

Tyr Val Phe Gly Asp Arg Asn Gly Asn Phe Leu Thr Leu Gln Gln Xaa
            500                 505                 510

Pro Xaa Thr Lys Gln Trp Gln Glu Lys Pro Leu Cys Leu Gly Xaa Ser
        515                 520                 525

Xaa Ser Cys Arg Gly Xaa Phe Ser Gly Xaa Xaa Leu Gly Phe Gly Glu
    530                 535                 540

Asp Glu Leu Gly Glu Xaa Tyr Ile Leu Ser Ser Ser Lys Ser Met Thr
545                 550                 555                 560

Gln Thr His Asn Gly Lys Leu Tyr Lys Ile Xaa Asp Pro Lys Arg Pro
                565                 570                 575

Leu Xaa Pro Glu Glu Cys Xaa Xaa Thr Xaa Xaa Xaa Ala Gln Xaa Leu
            580                 585                 590

Thr Ser Xaa Cys Ser Arg Xaa Cys Arg Asn Gly Xaa Xaa Thr Pro Thr
        595                 600                 605

Gly Lys Cys Cys Cys Xaa Xaa Gly Trp Glu Gly Xaa Phe Cys Arg Xaa
    610                 615                 620

Ala Lys Cys Xaa Pro Ala Cys Arg His Gly Gly Val Cys Val Arg Pro
625                 630                 635                 640

Asn Lys Cys Leu Cys Lys Lys Gly Tyr Leu Gly Pro Gln Cys Glu Gln
                645                 650                 655
```

<210> SEQ ID NO 16
<211> LENGTH: 663
<212> TYPE: PRT
<213> ORGANISM: Artificial Sequence
<220> FEATURE:
<223> OTHER INFORMATION: Description of Artificial Sequence: Formula
sequence
<220> FEATURE:
<221> NAME/KEY: MOD_RES
<222> LOCATION: (1)..(663)
<223> OTHER INFORMATION: Xaa may be any natural amino acid -continued

<400> SEQUENCE: 16

```
Leu Gly Phe Phe Glu Gly Asp Ala Lys Phe Gly Glu Arg Xaa Glu Gly
  1               5                  10                  15

Ser Gly Ala Arg Arg Arg Arg Cys Leu Asn Gly Asn Pro Pro Lys Arg
             20                  25                  30

Leu Lys Arg Arg Asp Arg Arg Xaa Met Ser Gln Leu Glu Leu Leu Ser
         35                  40                  45

Gly Gly Glu Xaa Leu Cys Gly Gly Phe Tyr Pro Arg Xaa Ser Cys Cys
     50                  55                  60

Leu Xaa Ser Asp Ser Pro Gly Leu Gly Arg Leu Glu Asn Lys Ile Phe
 65                  70                  75                  80

Ser Xaa Thr Asn Asn Xaa Glu Cys Xaa Xaa Leu Leu Glu Glu Ile Xaa
                 85                  90                  95

Cys Ala Xaa Cys Ser Pro His Ser Gln Ser Leu Phe Xaa Xaa Pro Glu
            100                 105                 110

Arg Xaa Val Leu Xaa Xaa Asp Xaa Xaa Leu Pro Leu Leu Cys Lys Asp
        115                 120                 125

Tyr Cys Lys Glu Phe Phe Tyr Thr Cys Arg Gly His Ile Pro Gly Xaa
    130                 135                 140

Leu Gln Thr Thr Ala Asp Glu Phe Cys Phe Tyr Tyr Ala Arg Lys Asp
145                 150                 155                 160

Xaa Gly Leu Cys Phe Pro Asp Phe Pro Arg Lys Gln Val Arg Gly Pro
                165                 170                 175

Ala Ser Asn Tyr Leu Xaa Gln Met Glu Xaa Tyr Xaa Lys Val Xaa Xaa
            180                 185                 190

Ile Ser Arg Lys His Lys His Asn Cys Xaa Cys Xaa Gln Glu Val Xaa
        195                 200                 205

Ser Gly Leu Arg Gln Pro Val Xaa Ala Xaa His Ser Gly Asp Gly Ser
    210                 215                 220

Xaa Arg Leu Phe Ile Leu Glu Lys Glu Gly Tyr Val Lys Ile Leu Thr
225                 230                 235                 240

Pro Glu Gly Glu Xaa Phe Lys Glu Pro Tyr Leu Asp Ile His Lys Leu
                245                 250                 255

Val Gln Ser Gly Ile Lys Gly Gly Asp Glu Arg Gly Leu Leu Ser Leu
            260                 265                 270

Ala Phe His Pro Asn Tyr Lys Lys Asn Gly Lys Leu Tyr Val Ser Tyr
        275                 280                 285

Thr Thr Asn Gln Glu Arg Trp Ala Ile Gly Pro His Asp His Ile Leu
    290                 295                 300

Arg Val Val Glu Tyr Thr Val Ser Arg Lys Asn Pro His Gln Val Asp
305                 310                 315                 320

Xaa Arg Thr Ala Arg Xaa Phe Leu Glu Val Ala Glu Leu His Arg Lys
                325                 330                 335

His Leu Gly Gly Gln Leu Leu Phe Gly Pro Asp Gly Phe Leu Tyr Ile
            340                 345                 350

Ile Leu Gly Asp Gly Met Ile Thr Leu Asp Asp Met Glu Glu Met Asp
        355                 360                 365

Gly Leu Ser Asp Phe Thr Gly Ser Val Leu Arg Leu Asp Val Asp Thr
    370                 375                 380

Asp Met Cys Asn Val Pro Tyr Ser Ile Pro Arg Ser Asn Pro His Phe
385                 390                 395                 400

Asn Ser Thr Asn Gln Pro Pro Glu Val Phe Ala His Gly Leu His Asp
```

-continued 405 410 415

Pro Gly Arg Cys Ala Val Asp Arg His Pro Thr Asp Ile Asn Ile Asn
420 425 430

Leu Thr Ile Leu Cys Ser Asp Ser Asn Gly Lys Asn Arg Ser Ser Ala
435 440 445

Arg Ile Leu Gln Ile Ile Lys Gly Arg Asp Tyr Glu Ser Glu Pro Ser
450 455 460

Leu Leu Glu Phe Lys Pro Phe Ser Asn Gly Pro Leu Val Gly Gly Phe
465 470 475 480

Val Tyr Arg Gly Cys Gln Ser Glu Arg Leu Tyr Gly Ser Tyr Val Phe
485 490 495

Gly Asp Arg Asn Gly Asn Phe Leu Thr Leu Gln Gln Ser Pro Val Thr
500 505 510

Lys Gln Trp Gln Glu Lys Pro Leu Cys Leu Gly Xaa Ser Xaa Ser Cys
515 520 525

Arg Gly Tyr Phe Ser Gly His Ile Leu Gly Phe Gly Glu Asp Glu Leu
530 535 540

Gly Glu Val Tyr Ile Leu Ser Ser Ser Lys Ser Met Thr Gln Thr His
545 550 555 560

Asn Gly Lys Leu Tyr Lys Ile Val Asp Pro Lys Arg Pro Leu Met Pro
565 570 575

Glu Glu Cys Arg Xaa Thr Val Gln Pro Ala Gln Xaa Leu Thr Ser Xaa
580 585 590

Cys Ser Arg Leu Cys Arg Asn Gly Tyr Xaa Thr Pro Thr Gly Lys Cys
595 600 605

Cys Cys Ser Pro Gly Trp Glu Gly Asp Phe Cys Arg Xaa Ala Lys Cys
610 615 620

Glu Pro Ala Cys Arg His Gly Gly Val Cys Val Arg Pro Asn Lys Cys
625 630 635 640

Leu Cys Lys Lys Gly Tyr Leu Gly Pro Gln Cys Glu Gln Val Asp Arg
645 650 655

Asn Xaa Arg Arg Val Thr Arg
660

<210> SEQ ID NO 17
<211> LENGTH: 2135
<212> TYPE: DNA
<213> ORGANISM: Artificial Sequence
<220> FEATURE:
<223> OTHER INFORMATION: Description of Artificial Sequence: Consensus sequence
<220> FEATURE:
<221> NAME/KEY: MOD_RES
<222> LOCATION: (1)..(2135)
<223> OTHER INFORMATION: “n” base may be a, t, c or g

<400> SEQUENCE: 17
atgctsaaga tgctsycstt yaagctgctr ctgstggccg tggctctgkg cttcttygar 60
ggrgatgcba agttyggga aagrarcgar gggagcggmg crmgraggag amggtgccts 120
aaygggamcc csccrmrgcg sctraararr mgvgacmggm ggvtgmtgtc ccagcyggag 180
sygcysrgyg gvgsrgagry smtgtgysgy ggcytctacc cdcgvstvtc ytgctgcyys 240
crsrsygacr sscmkggryt rskgcrysys grgrmyaaga tmytttctgy yacsaacaac 300
wcagaatgyr ssargytrct ggaggaratc maatgygcwc hytgctchcc dcatkcycar 360
aryctbttcy acwcacctga raaaggrgaw ryyyykgawr grgammtary wcttccbyws 420

-continued

```
ytstgcaaag actaytgyaa agaattctwt tayacttgcm gaggycaywt wccaggtyty    480

ctycaaacwa cwgckgatga rttttgcttt tactatgcaa gaaaagatgs tggkktrtgc    540

tttccagayt tyccragaaa rcaagtsmga ggrccagcwt ctaactmcyt ggrccasatg    600

gargamtayg asaaagwggr rgrgatcagc agaaarcaca arcacaactg cytctgtrty    660

caggarrtyv wkagyggdct dmrrcarccy gtkrghgybs trcaywgygg rgatggmtcb    720

cadcgbctyt tyatwytdga rarrgaaggh twygtgwrra thythashcm wgamrkrgam    780

mtbhtmaarg arccttwyyt ggayatwcay aarctkgtwc aaagtggwwt aaagggrgga    840

gaygaaagrg gmytgytaag cctbgcattc caycccaatt ayaagaaaaa tggmaagyts    900

taygtstcyt atacsaccaa ccargarcgr tggrctatyg grccwcayga ycacatyctt    960

mgkgtdgtrg artacacagt rtccagraaa aayccmmahc argtkgaydy ragracwscy   1020

mgrrtbttwh tdgaagthgc agarcthcay mgaaarcatc tdggrggvca rctbctsttt   1080

ggbccwgayg gbytyytrya crtywtyytw ggdgatggba tgatyachyt sgayrayatg   1140

gargaratgg atggkytrag ygayttyaca ggytcwgtdy tdmgsstsga ygtrrayach   1200

gacmtgttgy aryrybccyt aytccatacc hmgraryaay cchyayttya ayagcacmaa   1260

ycarccycch gaartntttg chcayggnct scayraycca ggsmgrtgtg chgtrgatmr   1320

vcwycshryd gayrymaayr ksartytrmy ratmctktgy wcagaywcmr wyggcraara   1380

tacgacaaca ggcaggatcc tacagrtcwt cagcmagaat yytacagata ataaagggda   1440

ragaytayga aarygagccw tcwmtkytwg amttsrrryc awkcrghrry rshvcbyykg   1500

tyggtggatt trthtaymgr gghtgycagt cwrraagryt btayggaagy taygtrttyg   1560

gagaymrhaa tggraaytty hkaaybctsc armrrmvyyy wgahrachra rywrtggcaa   1620

garaarccnc tytgyctbgg yrmyagyrgb tcmtgtvgwk sythsytkky vggycmyrtc   1680

ytgggrtttg ghgaagatga aytagghgar rtytacathy twkymwscag yaaragyaya   1740

gmcmmasast crcaatggaa armtctacaa rwtbrtdgay ccmaaaagrc cwywartkcc   1800

trargartgc ararbmmcrg ywsrrbmksc msagmyrctr ashwchgmdt gytcmmgksw   1860

mtgymrraay ggsyactrya cmccmacdgg maartgctgc tgyartsmmg gctgggargg   1920

vsmsttctgc wkambwgcma artgtgavcy rgcdtgycgh matggmggkg tctgtgthrr   1980

rccbaayaar tgyytmtgya arrarggghtw tyytggymmy cartgyagwa margwgagmb   2040

agrracdwmm gvrracgrtk asmargvcag gyrtyctkga kcasatchth gacatgacrw   2100

cytacytgct ggayctmach arytayattg twtar                              2135
```

```
<210> SEQ ID NO 18
<211> LENGTH: 592
<212> TYPE: PRT
<213> ORGANISM: Artificial Sequence
<220> FEATURE:
<223> OTHER INFORMATION: Description of Artificial Sequence: Consensus
      sequence

<400> SEQUENCE: 18

Met Leu Lys Met Leu Phe Lys Leu Leu Leu Ala Val Ala Leu Phe Phe
  1               5                  10                  15

Glu Gly Asp Ala Lys Phe Gly Glu Ser Gly Ala Arg Arg Arg Arg Cys
             20                  25                  30

Leu Asn Gly Pro Pro Arg Leu Lys Arg Asp Arg Arg Ser Glu Gly Glu
         35                  40                  45

Cys Gly Tyr Pro Arg Ser Cys Cys Asp Gly Leu Lys Ile Ser Thr Asn
```

-continued

```
    50                  55                  60

Asn Glu Cys Leu Leu Glu Glu Ile Cys Ala Cys Ser Pro His Gln Leu
 65                  70                  75                  80

Phe Pro Glu Leu Pro Leu Cys Lys Asp Tyr Cys Lys Glu Phe Tyr Thr
                 85                  90                  95

Cys Arg Gly His Pro Gly Leu Gln Thr Thr Ala Asp Glu Phe Cys Phe
            100                 105                 110

Tyr Tyr Ala Arg Lys Asp Gly Cys Phe Pro Asp Phe Pro Arg Lys Gln
        115                 120                 125

Val Arg Gly Pro Ala Ser Asn Leu Met Glu Tyr Lys Ile Ser Arg Lys
    130                 135                 140

His Lys His Asn Cys Cys Gln Glu Val Ser Gly Leu Arg Gln Pro Val
145                 150                 155                 160

Gly Ala Val His Gly Asp Gly Ser Arg Phe Leu Ile Leu Glu Lys Glu
                165                 170                 175

Gly Tyr Val Lys Ile Leu Thr Pro Glu Gly Glu Lys Glu Pro Leu Asp
            180                 185                 190

Ile His Lys Leu Val Gln Ser Gly Ile Lys Gly Gly Asp Glu Arg Gly
        195                 200                 205

Leu Leu Ser Leu Ala Phe His Pro Asn Tyr Lys Lys Asn Gly Lys Leu
    210                 215                 220

Tyr Val Ser Tyr Thr Thr Asn Gln Glu Arg Trp Ala Ile Gly Pro His
225                 230                 235                 240

Asp His Ile Leu Arg Val Val Glu Tyr Thr Val Ser Arg Lys Asn Pro
                245                 250                 255

Gln Val Asp Arg Thr Ala Arg Val Phe Leu Glu Val Ala Glu Leu His
            260                 265                 270

Arg Lys His Leu Gly Gly Gln Leu Leu Phe Gly Pro Asp Gly Phe Leu
        275                 280                 285

Tyr Ile Leu Gly Asp Gly Met Ile Thr Leu Asp Asp Met Glu Glu Met
    290                 295                 300

Asp Gly Leu Ser Asp Phe Thr Gly Ser Val Leu Arg Leu Asp Val Asp
305                 310                 315                 320

Thr Asp Cys Val Pro Tyr Ser Ile Pro Arg Ser Asn Pro His Phe Asn
                325                 330                 335

Ser Thr Asn Gln Pro Pro Glu Phe Ala His Gly Leu His Asp Pro Gly
            340                 345                 350

Arg Cys Ala Val Asp His Pro Asp Asn Ile Asn Leu Thr Ile Leu Cys
        355                 360                 365

Ser Asp Ser Asn Gly Lys Asn Arg Ser Ser Ala Arg Ile Leu Gln Ile
    370                 375                 380

Ile Lys Gly Lys Asp Tyr Glu Ser Glu Pro Ser Leu Leu Glu Phe Lys
385                 390                 395                 400

Pro Phe Ser Gly Leu Val Gly Gly Phe Val Tyr Arg Gly Cys Gln Ser
                405                 410                 415

Glu Arg Leu Tyr Gly Ser Tyr Val Phe Gly Asp Arg Asn Gly Asn Phe
            420                 425                 430

Leu Thr Leu Gln Gln Pro Thr Lys Gln Trp Gln Glu Lys Pro Leu Cys
        435                 440                 445

Leu Gly Ser Ser Cys Arg Gly Phe Ser Gly His Ile Leu Gly Phe Gly
    450                 455                 460

Glu Asp Glu Leu Gly Glu Val Tyr Ile Leu Ser Ser Ser Lys Ser Met
465                 470                 475                 480
```

-continued

```
Thr Gln Thr His Asn Gly Lys Leu Tyr Lys Ile Val Asp Pro Lys Arg
                485                 490                 495

Pro Leu Pro Glu Glu Cys Arg Thr Val Ala Gln Leu Thr Ser Cys Ser
            500                 505                 510

Arg Cys Arg Asn Gly Cys Thr Pro Thr Gly Lys Cys Cys Cys Gly Trp
        515                 520                 525

Glu Gly Phe Cys Arg Ala Lys Cys Glu Pro Ala Cys Arg His Gly Gly
    530                 535                 540

Val Cys Val Arg Pro Asn Lys Cys Leu Cys Lys Lys Gly Tyr Leu Gly
545                 550                 555                 560

Pro Gln Cys Glu Gln Val Asp Arg Asn Arg Thr Arg Gly Ile Leu Asp
                565                 570                 575

Gln Ile Asp Met Thr Ser Tyr Leu Leu Asp Leu Thr Ser Tyr Ile Val
            580                 585                 590
```

HEDGEHOG INTERACTING PROTEINS AND USES RELATED THERETO

RELATED APPLICATIONS

This application is a continuation of U.S. application Ser. No. 10/288,556, filed Nov. 4, 2002, now U.S. Pat. No. 7,115, 394 which is a continuation of U.S. application Ser. No. 08/933,711, filed Sep. 19, 1997, now U.S. Pat. No. 6,514,724, which claims benefit of U.S. Provisional Application No. 60/026,155, filed Sep. 20, 1996, the specifications of each of which are incorporated by reference herein.

FUNDING

Work described herein was supported by funding from the National Institutes of Health (NIH) grant no. NS33642. The United States Government has certain rights to the invention.

BACKGROUND OF THE INVENTION

Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development from the earliest establishment of the body plan, to the patterning of the organ systems, to the generation of diverse cell types during tissue differentiation (Davidson, E., (1990) *Development* 108: 365-389; Gurdon, J. B., (1992) *Cell* 68: 185-199; Jessell, T. M. et al., (1992) *Cell* 68: 257-270). The effects of developmental cell interactions are varied. Typically, responding cells are diverted from one route of cell differentiation to another by inducing cells that differ from both the uninduced and induced states of the responding cells (inductions). Sometimes cells induce their neighbors to differentiate like themselves (homoiogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation (J. B. Gurdon (1992) *Cell* 68:185-199).

The origin of the nervous system in all vertebrates can be traced to the end of gastrulation. At this time, the ectoderm in the dorsal side of the embryo changes its fate from epidermal to neural. The newly formed neuroectoderm thickens to form a flattened structure called the neural plate which is characterized, in some vertebrates, by a central groove (neural groove) and thickened lateral edges (neural folds). At its early stages of differentiation, the neural plate already exhibits signs of regional differentiation along its anterior posterior (A-P) and mediolateral axis (M-L). The neural folds eventually fuse at the dorsal midline to form the neural tube which will differentiate into brain at its anterior end and spinal cord at its posterior end. Closure of the neural tube creates dorsal/ventral differences by virtue of previous mediolateral differentiation. Thus, at the end of neurulation, the neural tube has a clear anterior-posterior (A-P), dorsal ventral (D-V) and mediolateral (M-L) polarities (see, for example, *Principles in Neural Science* (3*rd*), eds. Kandel, Schwartz and Jessell, Elsevier Science Publishing Company: NY, 1991; and *Developmental Biology* (3*rd*), ed. S. F. Gilbert, Sinauer Associates: Sunderland Mass., 1991). Inductive interactions that define the fate of cells within the neural tube establish the initial pattern of the embryonic vertebrate nervous system. In the spinal cord, the identify of cell types is controlled, in part, by signals from two midline cell groups, the notochord and floor plate, that induce neural plate cells to differentiate into floor plate, motor neurons, and other ventral neuronal types (van Staaaten et al. (1988) *Anat. Embryol.* 177:317-324; Placzek et al. (1993) *Development* 117:205-218; Yamada et al. (1991) *Cell* 64:035-647; and Hatta et al. (1991) *Nature* 350:339-341). In addition, signals from the floor plate are responsible for the orientation and direction of commissural neuron outgrowth (Placzek, M. et al., (1990) *Development* 110: 19-30). Besides patterning the neural tube, the notochord and floorplate are also responsible for producing signals which control the patterning of the somites by inhibiting differentiation of dorsal somite derivatives in the ventral regions (Brand-Saberi, B. et al., (1993) *Anat. Embryol.* 188: 239-245; Porquie, O. et al., (1993) *Proc. Natl. Acad. Sci. USA* 90: 5242-5246).

Another important signaling center exists in the posterior mesenchyme of developing limb buds, called the Zone of Polarizing Activity, or "ZPA". When tissue from the posterior region of the limb bud is grafted to the anterior border of a second limb bud, the resultant limb will develop with additional digits in a mirror-image sequence along the anteroposterior axis (Saunders and Gasseling, (1968) *Epithelial-Mesenchymal Interaction*, pp. 78-97). This finding has led to the model that the ZPA is responsible for normal anteroposterior patterning in the limb. The ZPA has been hypothesized to function by releasing a signal, termed a "morphogen", which forms a gradient across the early embryonic bud. According to this model, the fate of cells at different distances from the ZPA is determined by the local concentration of the morphogen, with specific thresholds of the morphogen inducing successive structures (Wolpert, (1969) *Theor. Biol.* 25:147). This is supported by the finding that the extent of digit duplication is proportional to the number of implanted ZPA cells (Tickle, (1981) *Nature* 254:199-202).

Although the existence of inductive signals in the ZPA has been known for years, the molecular identities of these signals are only now beginning to be elucidated. An important step forward has been the discovery that the secreted protein Sonic hedgehog (Shh) is produced in several tissues with organizing properties, including notochord, floor plate and ZPA (Echelard et al. (1993), *Cell* 75: 1417-1430; Bitgood, M. J. and A. P. McMahon (1995) *Dev. Biol.* 172:126-38). Misexpressing Shh mimics the inductive effects on ectopic notochord in the neural tube and somites (Echelard et al. (1993) supra) and also mimics ZPA function in the limb bud (Riddle et al. (1993) *Cell* 75:1401-16; Chang et al. (1994) *Development* 120: 3339-53).

The vertebrate family of hedgehog genes includes at least four members, e.g., paralogs of the single *drosophila* hedgehog gene. Exemplary hedgehog genes and proteins are described in PCT publications WO 95/18856 and WO 96/17924. Three of these members, herein referred to as Desert hedgehog (Dhh), Sonic hedgehog (Shh) and Indian hedgehog (Ihh), apparently exist in all vertebrates, including fish, birds, and mammals. A fourth member, herein referred to as tiggie-winkle hedgehog (Thh), appears specific to fish. Desert hedgehog (Dhh) is expressed principally in the testes, both in mouse embryonic development and in the adult rodent and human; Indian hedgehog (Ihh) is involved in bone development during embryogenesis and in bone formation in the adult; and, Shh, which as described above, is primarily involved in morphogenic and neuroinductive activities. Given the critical inductive roles of hedgehog polypeptides in the development and maintenance of vertebrate organs, the identification of hedgehog interacting proteins is of paramount significance in both clinical and research contexts.

SUMMARY OF THE INVENTION

The present invention relates to the discovery of a new class of hedgehog-binding protein, referred to herein as HIP (for hedgehog interacting protein). The HIP polypeptides of the present invention include polypeptides which bind the products of the hedgehog gene family. Hedgehog family members are known for their broad involvement in the formation and maintenance of ordered spatial arrangements of differentiated tissues invertebrates, both adult and embryonic, and can be used to generate and/or maintain an array of different vertebrate tissue both in vitro and in vivo.

In general, the invention features isolated HIP polypeptides, preferably substantially pure preparations of the subject HIP polypeptides. The invention also provides recombinantly produced HIP polypeptides. In preferred embodiments the polypeptide has a biological activity including the ability to bind a hedgehog protein with high affinity, e.g., with a nanomolar or smaller dissociation constant ($K_D$). HIP polypeptides which specifically antagonize such activities, such as may be provided by truncation mutants, are also specifically contemplated.

In one embodiment, the polypeptide is identical with or homologous to a HIP polypeptide represented in SEQ ID No: 5, SEQ ID No: 6, SEQ ID No: 7 and SEQ ID No: 8, or the core polypeptide sequence thereof (e.g., corresponding to residues 16-678 of SEQ ID. 5 or 6). Related members of the HIP family are also contemplated, for instance, a HIP polypeptide preferably has an amino acid sequence at least 65%, 67%, 69%, 70%, 75% or 80% homologous to a polypeptide represented by SEQ ID No: 5, SEQ ID No: 6, SEQ ID No: 7 and SEQ ID No: 8 though polypeptides with higher sequence homologies of, for example, 82%, 85%, 90% and 95% or are also contemplated. In a preferred embodiment, the HIP polypeptide is encoded by a nucleic acid which hybridizes under stringent conditions with a nucleic acid sequence represented in any one or more of SEQ ID Nos: 1-4 and 9-14. Homologs of the subject HIP proteins also include versions of the protein which are resistant to post-translation modification, as for example, due to mutations which alter modification sites (such as tyrosine, threonine, serine or aspargine residues), or which prevent glycosylation of the protein, or which prevent interaction of the protein with a HIP ligand, e.g. a hedgehog polypeptide.

The HIP polypeptide can comprise a full length protein, such as represented in SEQ ID No: 5, SEQ ID No: 6 or SEQ ID No: 7, or it may include the core polypeptide sequence thereof (e.g., corresponding to residues 16-678 of SEQ ID. 5 or 6), or it can include a fragment corresponding to one or more particular motifs/domains, or to arbitrary sizes, e.g., at least 5, 10, 25, 50, 100, 150 or 200 amino acids in length. In preferred embodiments, the HIP polypeptide includes a sufficient portion of the excellular ligand binding domain to be able to specifically bind to a hedgehog ligand, preferably with a $K_D$ of 9 μM or less and even more preferably of 9 nM or less. Truncated forms of the protein include, but are not limited to, soluble ligand binding domain fragments.

In certain preferred embodiments, the invention features a purified or recombinant HIP polypeptide having a core polypeptide molecular weight of about 78.4 kd. In other embodiments, the peptide core of a mature HIP protein preferably has a molecular weight in the range of 38.6 to 76.8 kD. It will be understood that certain post-translational modifications, e.g., glycosylation, prenylation, myristylation and the like, can increase the apparent molecular weight of the HIP protein relative to the unmodified polypeptide chain.

The subject proteins can also be provided as chimeric molecules, such as in the form of fusion proteins. For instance, the HIP protein can be provided as a recombinant fusion protein which includes a second polypeptide portion, e.g., a second polypeptide having an amino acid sequence unrelated (heterologous) to the HIP polypeptide, e.g. the second polypeptide portion is glutathione-S-transferase, e.g. the second polypeptide portion is an enzymatic activity such as alkaline phosphatase, e.g. the second polypeptide portion is an epitope tag.

In yet another embodiment, the invention features nucleic acids encoding HIP polypeptides, which have the ability to modulate, e.g., either mimic or antagonize, at least a portion of the activity of a wild-type HIP polypeptide. Exemplary HIP-encoding nucleic acid sequences are represented by SEQ ID No: 1, SEQ ID No: 2, SEQ ID No: 3 or SEQ ID No: 4.

In another embodiment, the nucleic acids of the present invention include coding sequences which hybridize under stringent conditions with all or a portion of the coding sequences designated in one or more of SEQ ID Nos: 1-4. The coding sequences of the nucleic acids can comprise sequences which are identical to coding sequences represented in SEQ ID Nos: 1, 2, 3, 4, 9, 10, 11, 12, 13 or 14, or it can merely be homologous to those sequences. In preferred embodiments, the nucleic acids encode polypeptides which specifically modulate, by acting as either agonists or antagonists, one or more of the bioactivities of wild-type HIP polypeptides.

Furthermore, in certain preferred embodiments, the subject HIP nucleic acids will include a transcriptional regulatory sequence, e.g. at least one of a transcriptional promoter or transcriptional enhancer sequence, which regulatory sequence is operably linked to the HIP gene sequences. Such regulatory sequences can be used in to render the HIP gene sequences suitable for use as an expression vector. The transcriptional regulatory sequence can be from a HIP gene, or from a heterologous gene.

This invention also contemplates the cells transfected with said expression vector whether prokaryotic or eukaryotic and a method for producing HIP proteins by employing said expression vectors.

In still other embodiments, the subject invention provides a gene activation construct, wherein the gene activation construct is deigned to recombine with a genomic HIP gene in a cell to provide, e.g., by heterologous recombination, a heterologous transcriptional regulatory sequence operatively linked to a coding sequence of a genomic HIP gene. Cells having genomic HIP genes modified by gene activation constructs are also specifically contemplated.

In yet another embodiment, the present invention provides nucleic acids which hybridize under stringent conditions to nucleic acid probes corresponding to at least 12 consecutive nucleotides of either sense or antisense sequences of SEQ ID No: 1, SEQ ID No: 2, SEQ ID No: 3 and SEQ ID No: 4; though preferably to at least 25 consecutive nucleotides; and more preferably to at least 40, 50 or 75 consecutive nucleotides of either sense or antisense sequence of SEQ ID No: 1, SEQ ID No: 2, SEQ ID No: 3 and SEQ ID No: 4.

Yet another aspect of the present invention concerns an immunogen comprising a HIP polypeptide in an immunogenic preparation, the immunogen being capable of eliciting an immune response specific for a HIP polypeptide; e.g. a humoral response, e.g. an antibody response; e.g. a cellular response. In preferred embodiments, the immunogen comprising an antigenic determinant, e.g. a unique determinant, from a protein represented by one of SEQ ID No: 5, SEQ ID No: 6. SEQ ID No: 7 and/or SEQ ID No: 8.

A still further aspect of the present invention features antibodies and antibody preparations specifically reactive with an epitope of the HIP immunogen.

The invention also features transgenic non-human animals, e.g. mice, rats, rabbits, chickens, frogs or pigs, having a transgene, e.g., animals which include (and preferably express) a heterologous form of a HIP gene described herein, or which misexpress an endogenous HIP gene, e.g., an animal in which expression of one or more of the subject HIP proteins is disrupted. Such a transgenic animal can serve as an animal model for studying cellular and tissue disorders comprising mutated or mis-expressed HIP alleles or for use in drug screening.

The invention also provides a probe/primer comprising a substantially purified oligonucleotide, wherein the oligonucleotide comprises a region of nucleotide sequence which hybridizes under stringent conditions to at least 12 consecutive nucleotides of sense or antisense sequences of any one or more of SEQ ID Nos: 1-4 and 9-14, or naturally occurring mutants thereof. In preferred embodiments, the probe/primer further includes a label group attached thereto and able to be detected. The label group can be selected, e.g., from a group consisting of radioisotopes, fluorescent compounds, enzymes, and enzyme co-factors. Probes of the invention can be used as a part of a diagnostic test kit for identifying dysfunctions associated with mis-expression of a HIP protein, such as for detecting in a sample of cells isolated from a patient, a level of a nucleic acid encoding a HIP protein; e.g. measuring a HIP mRNA level in a cell, or determining whether a genomic HIP gene has been mutated or deleted. These so-called "probes/primers" of the invention can also be used as a part of "antisense" therapy which refers to administration or in situ generation of oligonucleotide probes or their derivatives which specifically hybridize (e.g. bind) under cellular conditions, with the cellular mRNA and/or genomic DNA encoding one or more of the subject HIP proteins so as to inhibit expression of that protein, e.g. by inhibiting transcription and/or translation. Preferably, the oligonucleotide is at least 12 nucleotides in length, though primers of 25, 40, 50, or 75 nucleotides in length are also contemplated.

In yet another aspect, the invention provides an assay for screening test compounds for inhibitors, or alternatively, potentiators, of an interaction between a hedgehog protein and a HIP polypeptide receptor. An exemplary method includes the steps of (a) forming a reaction mixture including: (i) a hedgehog polypeptide, (ii) a HIP polypeptide, and (iii) a test compound; and (b) detecting interaction of the hedgehog and HIP polypeptides. A statistically significant change (potentiation or inhibition) in the interaction of the hedgehog and HIP polypeptides in the presence of the test compound, relative to the interaction in the absence of the test compound, indicates a potential agonist (mimetic or potentiator) or antagonist (inhibitor) of hedgehog bioactivity for the test compound. The reaction mixture can be a cell-free protein preparation, e.g., a reconsistuted protein mixture or a cell lysate, or it can be a recombinant cell including a heterologous nucleic acid recombinantly expressing the HIP polypeptide.

In preferred embodiments, the step of detecting interaction of the hedgehog and HIP polypeptides is a competitive binding assay. In other preferred embodiments, the step of detecting interaction of the hedgehog and HIP polypeptides involves detecting, in a cell-based assay, change(s) in the level of an intracellular second messenger responsive to signaling mediated by the HIP polypeptide. In still another preferred embodiment, the step of detecting interaction of the hedgehog and HIP polypeptides comprises detecting, in a cell-based assay, change(s) in the level of expression of a gene controlled by a transcriptional regulatory sequence responsive to signaling by the HIP polypeptide.

In preferred embodiments, the steps of the assay are repeated for a variegated library of at least 100 different test compounds, more preferably at least $10^3$, $10^4$ or $10^5$ different test compounds. The test compound can be, e.g., a peptide, a nucleic acid, a carbohydrate, a small organic molecule, or natural product extract (or fraction thereof).

The present invention further contemplates the pharmaceutical formulation of one or more agents identified in such drug screening assays.

In other embodiments, the present invention provides a molecule, preferably a small organic molecule, which binds to HIP and either mimics or antagonizes hedgehog-induced signaling in cells expressing HIP.

Yet another aspect of the present invention concerns a method for modulating one or more of growth, differentiation, or survival of a cell by modulating HIP bioactivity, e.g., by potentiating or disrupting certain protein-protein interactions. In general, whether carried out in vivo, in vitro, or in situ, the method comprises treating the cell with an effective amount of a HIP therapeutic so as to alter, relative to the cell in the absence of treatment, at least one of (i) rate of growth, (ii) differentiation, or (iii) survival of the cell. Accordingly, the method can be carried out with HIP therapeutics such as peptide and peptidomimetics or other molecules identified in the above-referenced drug screens which agonize or antagonize the effects of signaling from a HIP protein or ligand binding of a HIP protein, e.g., a hedgehog protein. Other HIP therapeutics include antisense constructs for inhibiting expression of HIP proteins, dominant negative mutants of HIP proteins which competitively inhibit ligand interactions upstream and signal transduction downstream of the wild-type HIP protein, and gene therapy constructs including gene activation constructs.

In one embodiment, the subject method of modulating HIP bioactivity can be used in the treatment of testicular cells, so as to modulate spermatogenesis. In another embodiment, the subject method is used to modulate osteogenesis, comprising the treatment of osteogenic cells with an agent that modulates HIP boactivity. Likewise, where the treated cell is a chondrogenic cell, the present method is used to modulate chondrogenesis. In still, another embodiment, the subject method can be used to modulate the differentiation of a neuronal cell, to maintain a neuronal cell in a differentiated state, and/or to enhance the survival of a neuronal cell, e.g., to prevent apoptosis or other forms of cell death. For instance the present method can be used to affect the differentiation of neuronal cells such as motor neurons, cholinergic neurons, dopaminergic neurons, serotonergic neurons, and peptidergic neurons.

Another aspect of the present invention provides a method of determining if a subject, e.g. an animal patient, is at risk for a disorder characterized by unwanted cell proliferation or aberrant control of differentiation or apoptosis. The method includes detecting, in a tissue of the subject, the presence or absence of a genetic lesion characterized by at least one of (i) a mutation of a gene encoding a HIP protein; or (ii) the mis-expression of a HIP gene. In preferred embodiments, detecting the genetic lesion includes ascertaining the existence of at least one of: a deletion of one or more nucleotides from a HIP gene; an addition of one or more nucleotides to the gene, a substitution of one or more nucleotides of the gene, a gross chromosomal rearrangement of the gene; an alteration in the level of a messenger RNA transcript of the gene; the presence of a non-wild type splicing pattern of a messenger RNA transcript of the gene; a non-wild type level of the protein; and/or an aberrant level of soluble HIP protein.

For example, detecting the genetic lesion can include (i) providing a probe/primer including an oligonucleotide containing a region of nucleotide sequence which hybridizes to a sense or antisense sequence of a HIP gene or naturally occurring mutants thereof, or 5' or 3' flanking sequences naturally associated with the HIP gene; (ii) exposing the probe/primer to nucleic acid of the tissue; and (iii) detecting, by hybridization of the probe/primer to the nucleic acid, the presence or absence of the genetic lesion; e.g. wherein detecting the lesion comprises utilizing the probe/primer to determine the nucleotide sequence of the HIP gene and, optionally, of the flanking nucleic acid sequences. For instance, the probe/primer can be employed in a polymerase chain reaction (PCR) or in a ligation chain reaction (LCR). In alternate embodiments, the level of a HIP protein is detected in an immunoassay using an antibody which is specifically immunoreactive with the HIP protein.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

Other features and advantages of the invention will be apparent from the following detailed description, and from the claims.

BRIEF DESCRIPTION OF THE DRAWINGS

FIG. 1A is an alignment of the HIP protein sequences for the mouse (SEQ ID NO: 5), human (SEQ ID NO: 6), chicken (SEQ ID NO: 7), and zebrafish (SEQ ID NO: 8) homologs. The Consensus (SEQ ID NO: 18) represents amino acid residues which are conserved in at least three of the four HIP protein sequences from mouse, human, chicken and zebrafish. The up-arrow indicates the C-terminal hydrophobic anchor.

FIG. 1B is an alignment of the coding sequences for HIP cDNAs isolated from mouse (SEQ ID NO: 1), human (SEQ ID NO: 2), chicken (SEQ ID NO: 3), and zebrafish (SEQ ID NO: 4). The Consensus (SEQ ID NO: 17) represents a consensus nucleotide sequence based on the HIP cDNA sequences from mouse, human, chicken and zebrafish. Nucleotides are represented by the one-letter code according to the WIPO standard.

DETAILED DESCRIPTION OF THE INVENTION

Of particular importance in the development and maintenance of tissue in vertebrate animals is a type of extracellular communication called induction, which occurs between neighboring cell layers and tissues. In inductive interactions, chemical signals secreted by one cell population influence the developmental fate of a second cell population. Typically, cells responding to the inductive signals are diverted from one cell fate to another, neither of which is the same as the fate of the signaling cells.

Inductive signals are key regulatory proteins that function in vertebrate pattern formation, and are present in important signaling centers known to operate embryonically, for example, to define the organization of the vertebrate embryo. For example, these signaling structures include the notochord, a transient structure which initiates the formation of the nervous system and helps to define the different types of neurons within it. The notochord also regulates mesodermal patterning along the body axis. Another distinct group of cells having apparent signaling activity is the floorplate of the neural tube (the precursor of the spinal cord and brain) which also signals the differentiation of different nerve cell types. It is also generally believed that the region of mesoderm at the bottom of the buds which form the limbs (called the Zone of Polarizing Activity or ZPA) operates as a signaling center by secreting a morphogen which ultimately produces the correct patterning of the developing limbs.

The regulation of hedgehog protein signaling is an important mechanism for developmental control. The present invention concerns the discovery of a new family of hedgehog binding proteins, referred to herein as "hedgehog interacting proteins" or "HIPs", which are demonstrated to bind to hedgehog polypeptides with high affinity. The mouse HIP clone was first identified by expression cloning techniques by its ability to bind to hedgehog protein. Subsequently, a variety of other vertebrate homologs have been cloned using probes and primers based on the mouse clone, again by standard techniques. As described herein, the vertebrate HIP proteins exhibit spatially and temporally restricted expression domains indicative of important roles in hedgehog-mediated induction.

Figure 2:
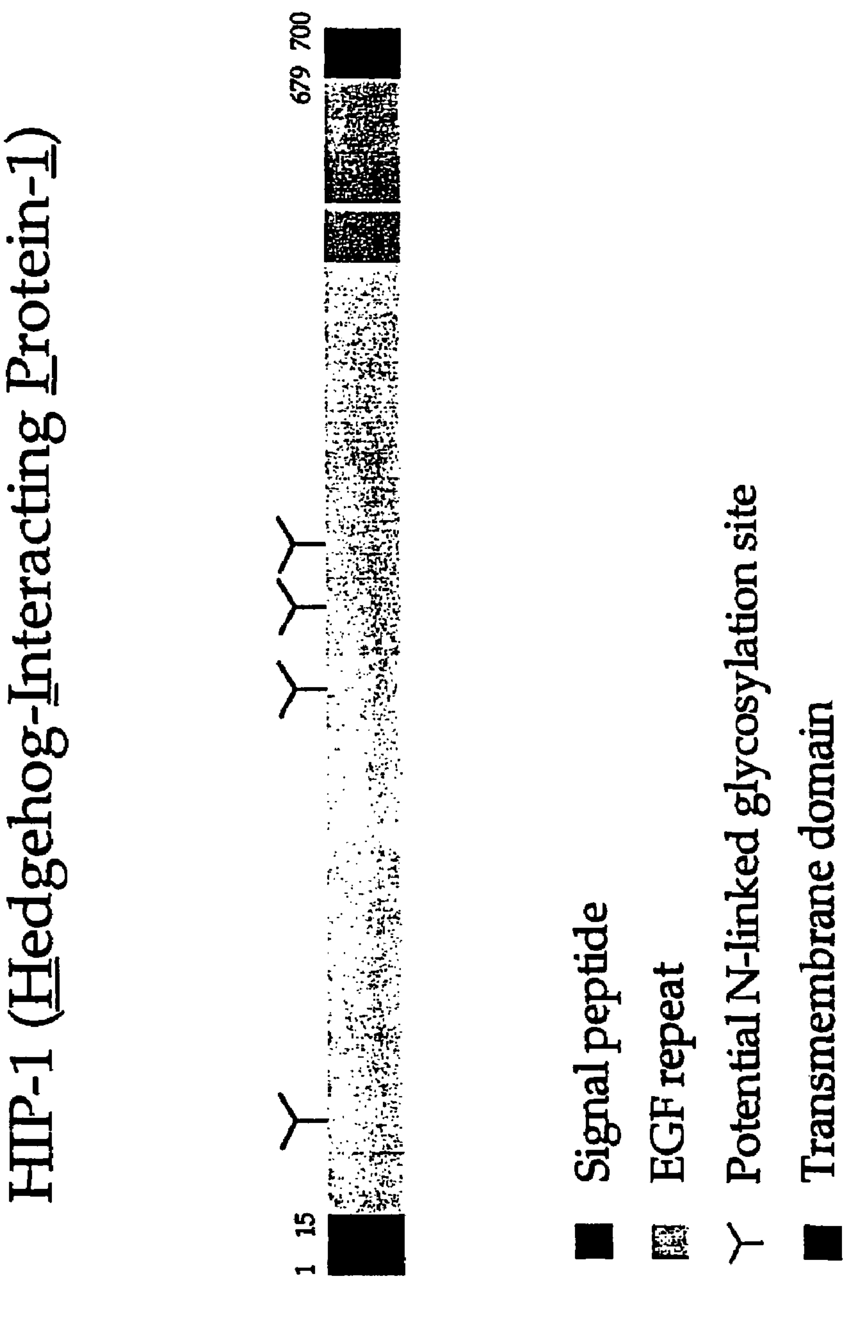
FIG. 2 is a schematic representation of the HIP protein.

The sequence of exemplary HIP genes cloned from various vertebrates (c.f., Table 1 below) indicates it encodes a secreted protein that may be anchored at the cell membrane. Comparison of HIP sequences from mouse, human, chick and zebrafish (see FIG. 1) suggests a conserved signal peptide sequence, a conserved hedgehog binding domain, and a potential transmembrane domain. Moreover, analysis of the protein sequences suggests 2 EGF-like domains in the C-terminal portion of the protein (see FIG. 2). Other than those domains, the HIP coding sequences do not show close sequence homology to any previously F identified genes, suggesting that these genes comprise a novel gene family.

The HIP proteins, through their ability to bind to hedgehog proteins, are apparently capable of modulating hedgehog signaling. The HIP proteins may function as a hedgehog receptor (or subunit thereof), or may act to sequester hedgehog proteins at the cell surface and thus control the effective concentration of hedgehog polypeptide available to other hedgehog receptors such as patched. The HIP proteins may mediate formation of a hedgehog gradient by forming complexes with soluble hedgehog proteins and affecting the ability of those proteins to interact with cell-surface receptors. Thus, the HIP polypeptides of the present invention may affect a number of hedgehog-mediated biological activities including: an ability to modulate proliferation, survival and/or differentiation of mesodermally-derived tissue, such as tissue derived from dorsal mesoderm, cartilage and tissue involved in spermatogenesis; the ability to modulate proliferation, survival and/or differentiation of ectodermally-derived tissue, such as tissue derived from the epidermis, neural tube, neural crest, or head mesenchyme; the ability to modulate proliferation, survival and/or differentiation of endodermally-derived tissue, such as tissue derived from the primitive gut.

Figure 3:
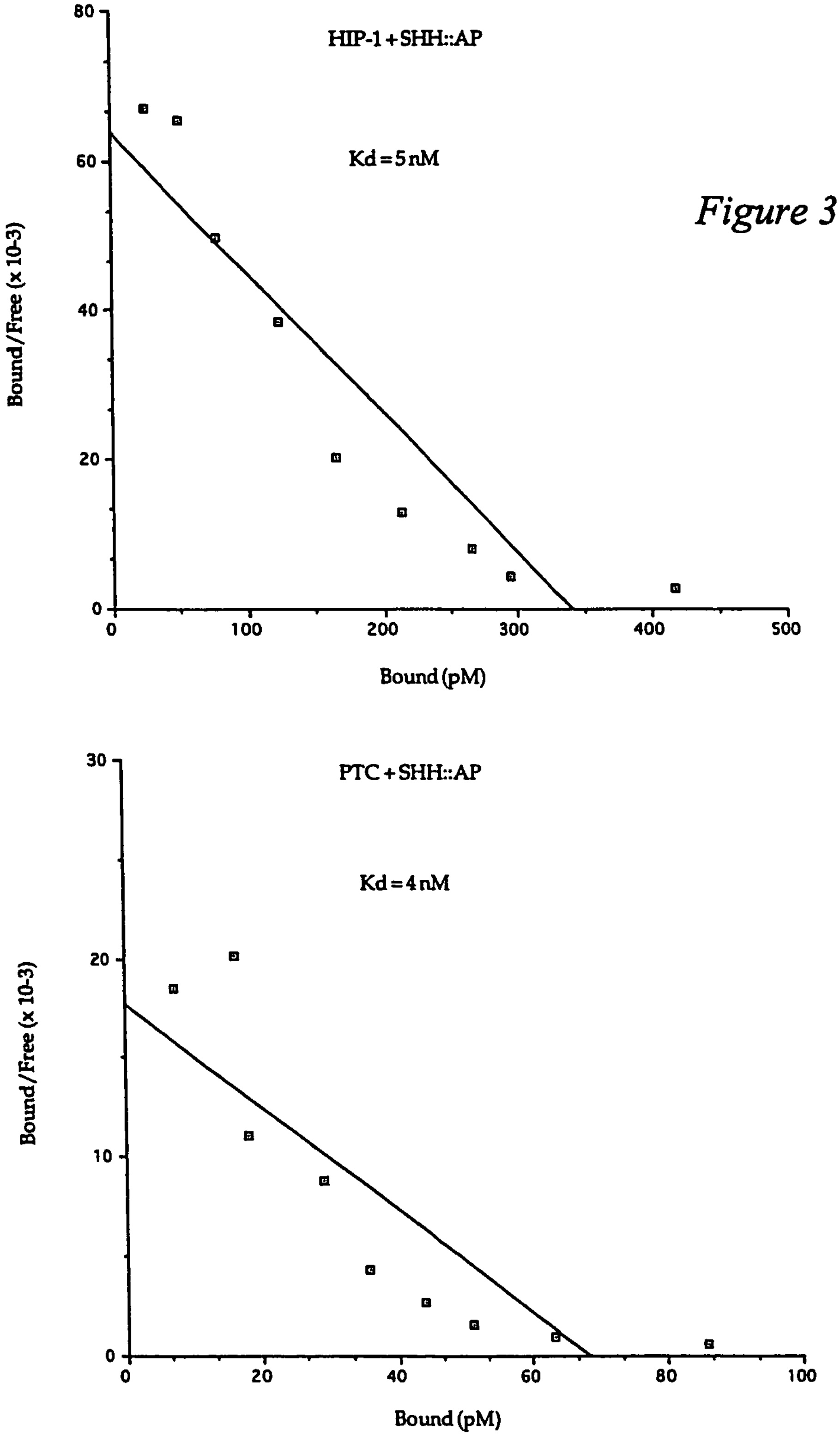
FIG. 3 shows two scatchard plots of the binding of a Shh-AP fusion protein (Ap=alkaline phosphatase) with HIP and PTC proteins.

A mouse HIP cDNA was identified in a screen for potential hedgehog-binding proteins using a mouse limb bud cDNA library cloned into a plasmid which allowed expression in cells, and detecting the amount of labeled Shh protein that bound specifically to the expressed proteins. A single positive cone was identified in 70,000 screened. Ligand-receptor binding studies indicate that the HIP polypeptide can bind various members of the hedgehog family with high affinity. For instance, the binding of the murine HIP polypeptide to each of Shh and Dhh occurred with a dissociation constant ($k_d$) of approximately 1 nM. For example, see FIG. 3. This binding is comparable to the hedgehog binding affinity observed for patched (see FIG. 3). This finding suggests that mouse HIP cDNA may encode a general hedgehog binding protein as opposed to a binding protein that selectively discriminates between hedgehog homologs. However, it is anticipated that other homologs of that protein may be able to distinguish, by binding affinity, between Shh, Ihh and Dhh.

In addition to the murine HIP clone, we have also obtained cDNA clones from other vertebrates, including human, avian and fish HIP genes, utilizing the mouse cDNA as a probe. According to the appended sequence listing, (see also Table 1) a murine HIP polypeptide is encoded by SEQ ID No:1; a human HIP polypeptide is encoded by SEQ ID No:2; a chicken HIP polypeptide is encoded by SEQ ID No:3; and a zebrafish HIP polypeptide is encoded by SEQ ID No:4.

TABLE 1

Guide to HIP sequences in Sequence Listing

| | Nucleotide | Amino Acid |
|---|---|---|
| Mouse HIP | SEQ ID No. 1 | SEQ ID No. 5 |
| Human HIP | SEQ ID No. 2 | SEQ ID No. 6 |
| 5' partial | SEQ ID No. 9 | |
| internal | SEQ ID No. 10 | |
| 3' partial | SEQ ID No. 11 | |
| Chicken HIP | SEQ ID No. 3 | SEQ ID No. 7 |
| 5' partial | SEQ ID No. 12 | |
| internal | SEQ ID No. 13 | |
| 3' partial | SEQ ID No. 14 | |
| Zebrafish HIP | SEQ ID No. 4 | SEQ ID No. 8 |

The overall sequence homology between the HIP proteins is shown in Table 2.

TABLE 2

Amino acid sequence identity between vertebrate HIP proteins.

| | Mouse | Human | Chicken |
|---|---|---|---|
| Human | 95% | | |
| Chicken | 82% | 85% | |
| Fish | 69% | 69% | 67% |

Figure 4:
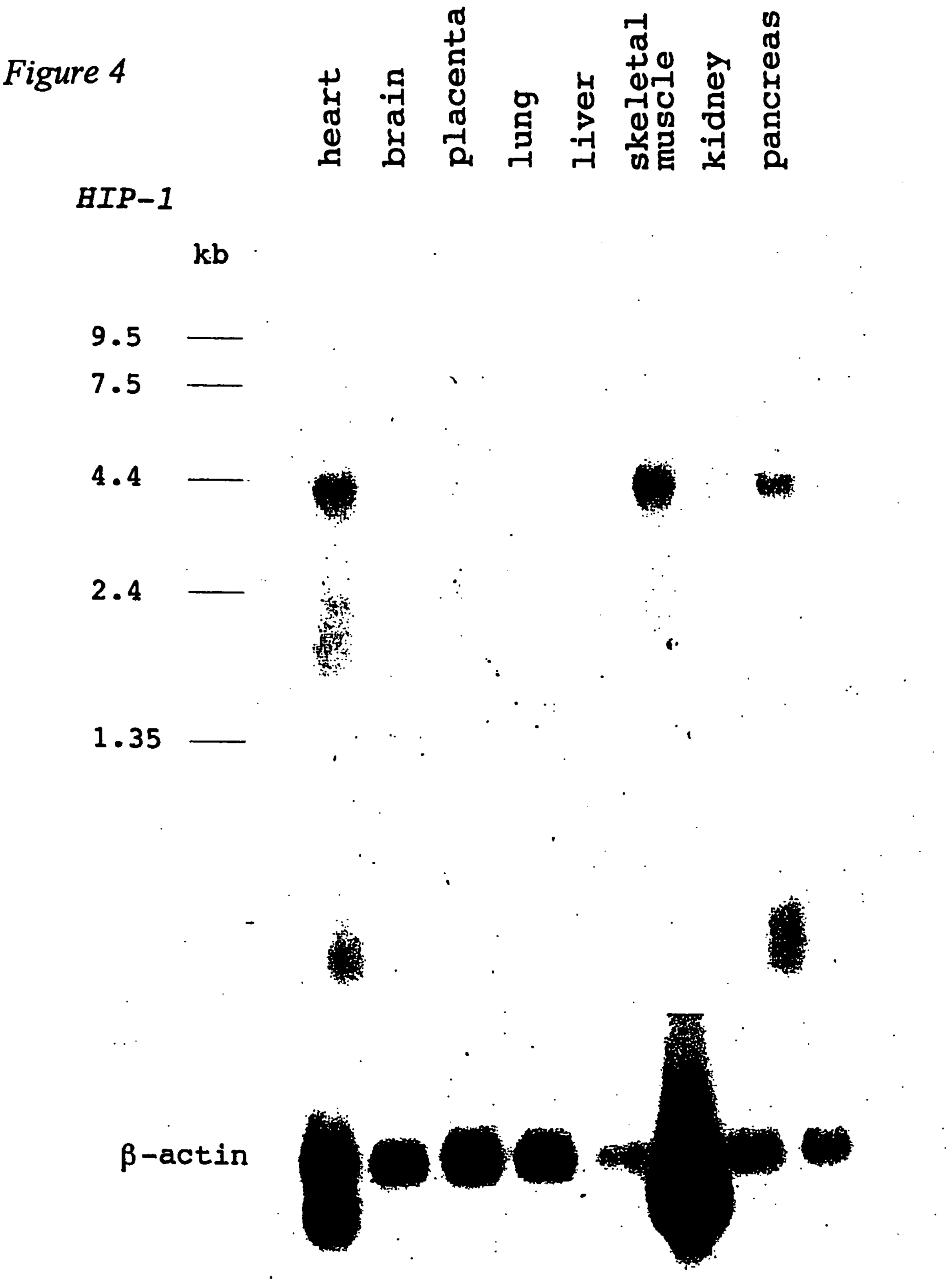
FIG. 4 is a human multiple tissue Northern blot for HIP transcripts.
Figure 5:
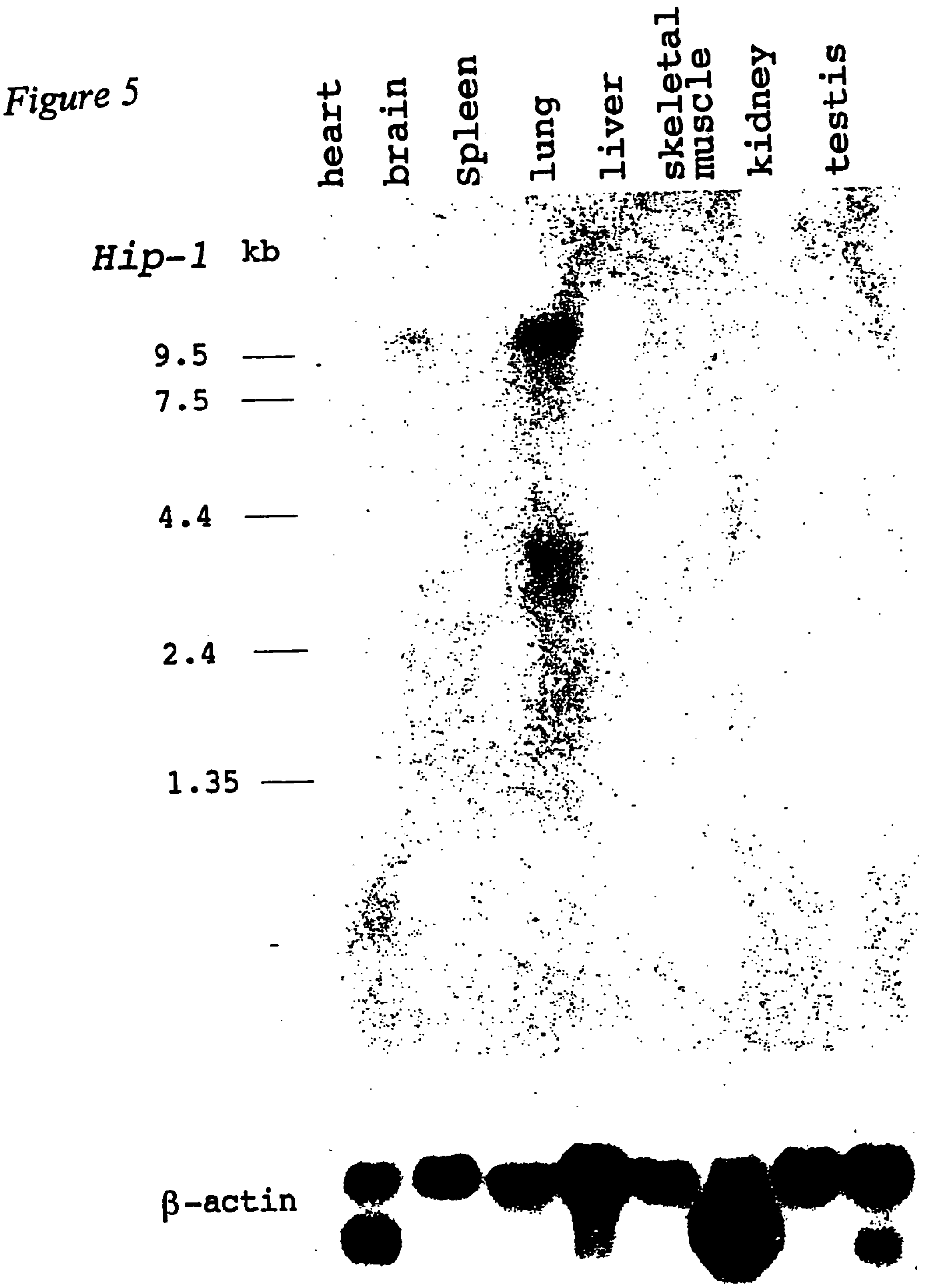
FIG. 5 is a mouse multiple tissue Northern blot for HIP transcripts.

By fluorescence in situ hybridization (FISH), a human HIP gene has been localized to chromosomal position 4Q31. As illustrated in FIGS. 4 and 5, Northern blot analysis suggests that a HIP gene is expressed in certain adult tissues, with higher levels indicated in heart, skeletal muscle and pancreas, at least in the tissue samples tested to date.

It is contemplated by the present invention that the cloned HIP genes set out in the appended sequence listing, in addition to representing a inter-species family of related genes, are also each part of an intra-species family. That is, it is anticipated that other paralogs of the human and mouse HIP proteins exist in those animals, and orthologs of each HIP gene are conserved amongst other animals. For instance, at low to medium stringency conditions, transcripts of about 4.4 kb and 9 kb were observed by Northern analysis of mouse samples (see FIG. 5), the latter representing a likely paralog and/or splice variant of the HIP cDNA set forth in SEQ ID No. 1.

In addition to the sequence variation between the various HIP homologs, the vertebrate HIP proteins are apparently present naturally in a number of different forms, including a pro-form. The pro-form includes an N-terminal signal peptide (approximately N-terminal residues 1-15) for directed secretion of at least the N terminal domain of the protein, while the full-length mature form lacks this signal sequence. Further processing of the mature form may also occur in some instances to yield biologically active fragments of the protein.

Figure 6:
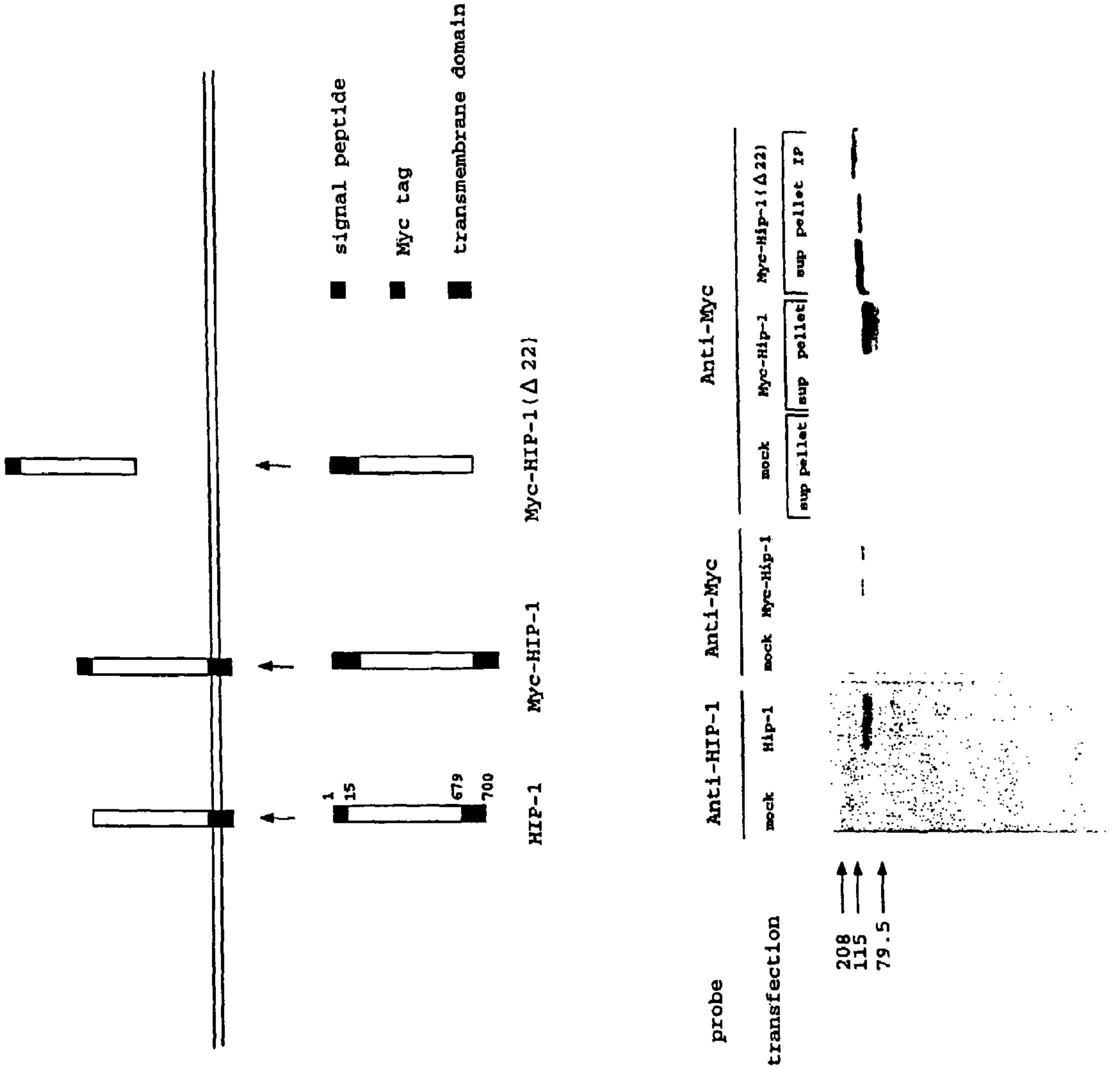
FIG. 6 illustrates that truncated forms of the HIP protein, in this instance lacking the C-terminal 22 amino acids, are secreted into the cell supernatant, whereas the full length HIP protein is retained in the cell fraction, e.g., remains membrane bound. Moreover, in the presence of Shh, anti-Shh can immunoprecipitate a complex including the secreted form of HIP protein.

Likewise, as illustrated in FIG. 6, the full-length HIP protein also includes a membrane anchor domain, e.g., a transmembrane domain, comprised of about the C-terminal 22 amino acids of the protein. HIP polypeptides lacking this sequence are shown to be fully secreted rather than membrane bound. Briefly, a myc-tagged fusion protein was created with the full length HIP sequence, myc-HIP-1, and a truncated form of HIP missing the C-terminal 22 amino acids, myc-HIP-1(Δ22). The myc-HIP-1 fusion protein was shown to run just slightly slower (high MW) than the full-length HIP protein when each was detected by anti-myc and anti-HIP antibodies, respectively. The anti-myc antibody was used to immunoblot samples of cell pellets and cell supernatant produced by cells expressing either the myc-HIP-1 fusion protein or the myc-HIP-1(Δ22) fusion protein. For the cells expressing myc-HIP-1, e.g., which retains the putative membrane anchoring domain, the protein was detected essentially exclusively in the cell pellet. On the other hand, the myc-HIP-1(Δ22) protein could be detected in both in the supernatant and the cell pellet. Moreover, the myc-HIP-1(Δ22) protein could be immunoprecipitated by anti-Shh antibody when the HIP protein was incubated with Shh protein.

While there is presently no evidence to suggest that the wild-type protein is glycosylated, it is formally possible that the HIP proteins may, under certain circumstances, also be modified post-translationally, such as by O-, S- and/or N-linked glycosylation. Potential Asn-glycosylation sites, relative to the mouse HIP protein sequence, include Asn99, Asn416, Asn447 and Asn459. Potential attachment sites for proteoglycan-like GAG chains (e.g., heparan sulfate, chondroitin sulfate and the like) include Ser235.

In order to determine, the expression pattern of the various HIP clones across species, in situ hybridization studies were performed in developing embryos of mice, chicken and fish. As described in the Examples below, HIP RNA distribution and its temporal expression is consistent with a role of HIP polypeptides as downstream targets of hedgehog signaling. In situ hybridization of mouse embryos indicate that HIP RNA is expressed at low levels at sites where hedgehog signaling is minimal, i.e. expression of Shh, Ihh or Dhh, is minimal and a dramatic upregulation of HIP expression occurs in response to the hedgehog upregulation. Firstly, upregulation of HIP polypeptides coincides temporarily with hh upregulation and its expression occurs opposite to the site of hh gene expression. Secondly, ectopic expression of HIP (RNA) occurs in response to ectopic expression of Shh in the CNS. Furthermore, HIP expression is activated in response to the expression of a dominant negative form of cAmp-dependent protein kinase A (PKA), which also activates other hh target genes such as patched. Furthermore, analysis of null Dhh-deficient mutant mice reveals loss of HIP expression in the testes, which is the target site for Dhh signaling.

1 Accordingly, certain aspects of the present invention relate to nucleic acids encoding HIP polypeptides, the HIP polypeptides themselves (including various fragments), antibodies immunoreactive with HIP proteins, and preparations of such compositions. Moreover, the present invention provides diagnostic and therapeutic assays and reagents for detecting and treating disorders involving, for example, aberrant expression (or loss thereof) of HIP, HIP ligands (particularly hedgehog proteins), or signal transducers thereof.

In addition, drug discovery assays are provided for identifying agents which can modulate the biological function of HIP proteins, such as by altering the binding of HIP molecules to hedgehog proteins or other extracellular/matrix factors, or the ability of the bound HIP protein to transduce hedgehog signals. Such agents can be useful therapeutically to alter the growth, maintenance and/or differentiation of a tissue, particularly a mesodermally-derived tissue, such cartilage, tissue involved in spermatogenesis and tissue derived from dorsal mesoderm; ectodermally-derived tissue, such as tissue derived from the epidermis, neural tube, neural crest, or head mesenchyme; endodermally-derived tissue, such as tissue derived from the primitive gut. Other aspects of the invention are described below or will be apparent to those skilled in the art in light of the present disclosure.

For convenience, certain terms employed in the specification and appended claims are collected here.

The term "hedgehog-binding protein" or "HIP" polypeptide refers to a family of polypeptides characterized at least in part by being identical or sharing a degree of sequence homology with all or a portion of the a HIP polypeptide represented in any of SEQ ID Nos: 5-8. The HIP polypeptides can be cloned or purified from any of a number of eukaryotic organisms, especially vertebrates, and particularly mammals. Moreover, other HIP polypeptides can be generated according to the present invention, which polypeptides do not ordinarily exist in nature, but rather are generated by non-natural mutagenic techniques.

A number of features of the HIP protein have been observed upon inspection. In particular, we have noted that HIP sequence encodes a secreted protein having a secretory signal sequence (e.g., a peptidyl portion which causes extracellular secretion of at least a portion of the protein) corresponding to residues 1-15 of SEQ ID No. 5. A membrane-anchoring domain, e.g., in the form of a transmembrane domain, may be provided by residues corresponding to either 357-377 or 680-700 of SEQ ID No: 5.

A "membrane-anchoring" region refers to sequence of amino acids that is capable of retaining the HIP polypeptide at the cell surface.

A "glycosylated" HIP polypeptide is an HIP polypeptide having a covalent linkage with a glycosyl group (e.g. a derivatized with a carbohydrate). For instance, the HIP protein can be glycosylated on an existing residue, or can be mutated to preclude carbohydrate attachment, or can be mutated to provide new glycosylation sites, such as for N-linked or O-linked glycosylation.

As used herein, the term "vertebrate hedgehog protein" refers to vertebrate inter-cellular signaling molecules related to the *Drosophilia* hedgehog protein. Three of the vertebrate hedgehog proteins, Desert hedgehog (Dhh), Sonic hedgehog (Shh) and Indian hedgehog (Ihh), apparently exist in all vertebrates, including amphibians, fish, birds, and mammals. Other members of this family, such as Banded hedgehog, Cephalic hedgehog, tiggy-wrinkle hedgehog, and echidna hedgehog have been so far identified in fish and/or amphibians. Exemplary hedgehog polypeptides are described in PCT applications WO96/17924, WO96/16668, WO95/18856.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "gene" or "recombinant gene" refers to a nucleic acid comprising an open reading frame encoding a HIP polypeptide, including both exon and (optionally) intron sequences. A "recombinant gene" refers to nucleic acid encoding a HIP polypeptide and comprising HIP-encoding exon sequences, though it may optionally include intron sequences which are derived from, for example, a chromosomal HIP gene or from an unrelated chromosomal gene. Exemplary recombinant genes encoding the subject HIP polypeptide are represented in the appended Sequence Listing. The term "intron" refers to a DNA sequence present in a given HIP gene which is not translated into protein and is generally found between exons.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a HIP polypeptide or, where anti-sense expression occurs from the transferred gene, the expression of a naturally-occurring form of the HIP protein is disrupted.

As used herein, the term "specifically hybridizes" refers to the ability of a nucleic acid probe/primer of the invention to hybridize to at least 15 consecutive nucleotides of a HIP gene, such as a HIP sequence designated in any one or more of SEQ ID Nos: 1-4 and 9-14, or a sequence complementary thereto, or naturally occurring mutants thereof, such that it has less than 15%, preferably less than 10%, and more preferably less than 5% background hybridization to a cellular nucleic acid (e.g., mRNA or genomic DNA) encoding a protein other than a HIP protein, as defined herein.

An "effective amount" of a hedgehog polypeptide, or a bioactive fragment thereof, with respect to the subject method of treatment, refers to an amount of agonist or antagonist in a preparation which, when applied as part of a desired dosage regimen, provides modulation of growth, differentiation or survival of cells, e.g., modulation of spermatogenesis, neuronal differentiation, or skeletogenesis, e.g., osteogenesis, chondrogenesis, or limb patterning.

As used herein, "phenotype" refers to the entire physical, biochemical, and physiological makeup of a cell, e.g., having any one trait or any group of traits.

The terms "induction" or "induce", as relating to the biological activity of a hedgehog protein, refers generally to the process or act of causing to occur a specific effect on the phenotype of cell. Such effect can be in the form of causing a change in the phenotype, e.g., differentiation to another cell phenotype, or can be in the form of maintaining the cell in a particular cell, e.g., preventing dedifferentation or promoting survival of a cell.

A "patient" or "subject" to be treated can mean either a human or non-human animal.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of a recombinant HIP gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of HIP genes.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of neuronal or hematopoietic origin. The term also covers so-called "leaky" promoters, which regulate expression of a selected DNA primarily in one tissue, but can cause at least low level expression in other tissues as well.

As used herein, the term "target tissue" refers to connective tissue, cartilage, bone tissue or limb tissue, which is either present in an animal, e.g., a mammal, e.g., a human or is present in in vitro culture, e.g, a cell culture.

As used herein, a "transgenic animal" is any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In an exemplary transgenic animal, the transgene causes cells to express a recombinant form of a HIP protein, e.g. either agonistic or antagonistic forms. However, transgenic animals in which the recombinant HIP gene is silent are also contemplated, as for example, the FLP or CRE recombinase dependent constructs described below. Moreover, "transgenic animal" also includes those recombinant animals in which gene disruption of one or more HIP genes is caused by human intervention, including both recombination and antisense techniques.

The "non-human animals" of the invention include vertebrates such as rodents, non-human primates, livestock, avian species, amphibians, reptiles, etc. The term "chimeric animal" is used herein to refer to animals in which the recombinant gene is found, or in which the recombinant is expressed in some but not all cells of the animal. The term "tissue-specific chimeric animal" indicates that a recombinant HIP gene is present and/or expressed or disrupted in some tissues but not others.

As used herein, the term "transgene" means a nucleic acid sequence (encoding, e.g., a HIP polypeptide, or pending an antisense transcript thereto), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a HIP polypeptide" may thus refer to one or more genes within a particular individual. Moreover, certain differences in nucleotide sequences may exist between individuals of the same species, which are called alleles. Such allelic differences may or may not result in differences in amino acid sequence of the encoded polypeptide yet still encode a protein with the same biological activity.

"Homology" and "identity" each refer to sequence similarity between two polypeptide sequences, with identity being a more strict comparison. Homology and identity can each be determined by comparing a position in each sequence which may be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be referred to as homologous at that position. A percentage of homology or identity between sequences is a function of the number of matching or homologous positions shared by the sequences. An "unrelated" or "non-homologous" sequence shares less than 40 percent identity, though preferably less than 25 percent identity, with a HIP sequence of the present invention.

The term "ortholog" refers to genes or proteins which are homologs via speciation, e.g., closely related and assumed to have common descent based on structural and functional considerations. Orthologous proteins function as recognizably the same activity in different species. The term "paralog" refers to genes or proteins which are homologs via gene duplication, e.g., duplicated variants of a gene within a genome. See also, Fritch, W M (1970) *Syst Zool* 19:99-113.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding a HIP polypeptide with a second amino acid sequence defining a domain (e.g. polypeptide portion) foreign to and not substantially homologous with any domain of a HIP protein. A chimeric protein may present a foreign domain which is found (albeit in a different protein) in an organism which also expresses the first protein, or it may be an "interspecies", "intergenic". etc. fusion of protein structures expressed by different kinds of organisms. In general, a fusion protein can be represented by the general formula X-HIP-Y, wherein HIP represents a portion of the fusion protein which is derived from a HIP protein, and X and Y are, independently, absent or represent amino acid sequences which are not related to a HIP sequences in an organism.

As used herein, a "reporter gene construct" is a nucleic acid that includes a "reporter gene" operatively linked to a transcriptional regulatory sequences. Transcription of the reporter gene is controlled by these sequences. The activity of at least one or more of these control sequences is directly or indirectly regulated by a signal transduction pathway involving a phospholipase, e.g., is directly or indirectly regulated by a second messenger produced by the phospholipase activity. The transcriptional regulatory sequences can include a promoter and other regulatory regions, such as enhancer sequences, that modulate the activity of the promoter, or regulatory sequences that modulate the activity or efficiency of the RNA polymerase that recognizes the promoter, or regulatory sequences that are recognized by effector molecules, including those that are specifically induced upon activation of a phospholipase. For example, modulation of the activity of the promoter may be effected by altering the RNA polymerase binding to the promoter region, or, alternatively, by interfering with initiation of transcription or elongation of the mRNA. Such sequences are herein collectively referred to as transcriptional regulatory elements or sequences. In addition, the construct may include sequences of nucleotides that alter the stability or rate of translation of the resulting mRNA in response to second messages, thereby altering the amount of reporter gene product.

As used herein, the terms "transforming growth factor-beta" and "TGF-β" denote a family of structurally related paracrine polypeptides found ubiquitously in vertebrates, and prototypic of a large family of metazoan growth, differentiation, and morphogenesis factors (see, for review, Massaque et al. (1990) *Ann Rev Cell Biol* 6:597-641; and Sporn et al. (1992) *J Cell Biol* 119:1017-1021). Included in this family are the "bone morphogenetic-proteins" or "BMPs", which refers to proteins isolated from bone, and fragments thereof and synthetic peptides which are capable of inducing bone deposition alone or when combined with appropriate cofactors. Preparation of BMPs, such as BMP-1, -2, -3, and -4, is described in, for example, PCT publication WO 88/00205. Wozney (1989) *Growth Fact Res* 1:267-280 describes additional BMP proteins closely related to BMP-2, and which have been designated BMP-5, -6, and -7. PCT publications WO89/09787 and WO89/09788 describe a protein called "OP-1," now known to be BMP-7. Other BMPs are known in the art.

The term "isolated" as also used herein with respect to nucleic acids, such as DNA or RNA, refers to molecules separated from other DNAs, or RNAs, respectively, that are present in the natural source of the macromolecule. For example, an isolated nucleic acid encoding a HIP polypeptide preferably includes no more than 10 kilobases (kb) of nucleic acid sequence which naturally immediately flanks the HIP gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

As described below, one aspect of the invention pertains to isolated nucleic acids comprising nucleotide sequences encoding HIP polypeptides, and/or equivalents of such nucleic acids. The term nucleic acid as used herein is intended to include fragments as equivalents. The term equivalent is understood to include nucleotide sequences encoding functionally equivalent HIP polypeptides or functionally equivalent peptides having an activity of a HIP protein such as described herein. Equivalent nucleotide sequences will include sequences that differ by one or more nucleotide substitutions, additions or deletions, such as allelic variants; and will, therefore, include sequences that differ from the nucleotide sequence of the HIP coding sequences shown in any one or more of SEQ ID Nos: 1-4 and 9-14 due to the degeneracy of the genetic code. Equivalents will also include nucleotide sequences that hybridize under stringent conditions (i.e., equivalent to about 20-27° C. below the melting temperature ($T_m$) of the DNA duplex formed in about 1M salt) to the nucleotide sequences represented in SEQ ID No: 1, 2, 3, 4, 9, 10, 11, 12, 13 or 14. In one embodiment, equivalents will further include nucleic acid sequences derived from and evolutionarily related to, a nucleotide sequences shown in SEQ ID No: 1, SEQ ID No: 2, SEQ ID No: 3 and SEQ ID No: 4.

Moreover, it will be generally appreciated that, under certain circumstances, it may be advantageous to provide homologs of a HIP polypeptide which function in a limited capacity as one of either an agonist (e.g., mimics or potentiates a bioactivity of the wild-type HIP protein) or an antagonist (e.g., inhibits a bioactivity of the wild-type HIP protein), in order to promote or inhibit only a subset of the biological activities of the naturally-occurring form of the protein. Thus, specific biological effects can be elicited by treatment with a homolog of limited function. For example, truncated forms of the hedgehog interacting protein, e.g., soluble fragments of the extracellular domain, can be provided to competitively inhibit ligand (hedgehog) binding to the wild-type HIP protein.

Homologs of the subject HIP protein can be generated by mutagenesis, such as by discrete point mutation(s), or by truncation. For instance, mutation can give rise to homologs which retain substantially the same, or merely a subset, of the biological activity of the HIP polypeptide from which it was derived. Alternatively, antagonistic forms of the protein can be generated which are able to inhibit the function of the naturally occurring form of the protein, such as by competitively binding to hedgehog proteins and competing with wild-type HIP, or binding to other hedgehog interacting proteins (such as subunits of a hedgehog receptor) to form unresponsive hedgehog receptor complexes. Thus, the HIP protein and homologs thereof provided by the subject invention may be either positive or negative regulators of cell growth, death and/or differentiation.

In general, polypeptides referred to herein as having an activity of a HIP protein (e.g., are "bioactive") are defined as polypeptides which include an amino acid sequence corresponding (e.g., identical or homologous) to all or a portion of the amino acid sequences of the HIP protein shown in SEQ ID No: 5, SEQ ID No: 6, SEQ ID No: 7 or SEQ ID No: 8, and which agonize or antagonize all or a portion of the biological/biochemical activities of a naturally occurring HIP protein. Examples of such biological activity includes the ability to bind with high affinity hedgehog proteins. The bioactivity of certain embodiments of the subject HIP polypeptides can be characterized in terms of an ability to promote differentiation and/or maintenance of cells and tissue from mesodermally-derived tissue, such as tissue derived from dorsal mesoderm; ectodermally-origin, such as tissue derived from the neural tube, neural crest, or head mesenchyme; or endodermally-derived tissue, such as tissue derived from the primitive gut.

Other biological activities of the subject HIP proteins are described herein or will be reasonably apparent to those skilled in the art. According to the present invention, a polypeptide has biological activity if it is a specific agonist or antagonist of a naturally-occurring form of a HIP protein.

Preferred nucleic acids encode a HIP polypeptide comprising an amino acid sequence at least 60%, 70% or 80% homologous, more preferably at least 85% homologous and most preferably at least 95% homologous with an amino acid sequence of a naturally occurring HIP protein, e.g., such as represented in SEQ ID No: 5, SEQ ID No: 6, SEQ ID No: 7 or SEQ ID No: 8. Nucleic acids which encode polypeptides at least about 98-99% homology with an amino acid sequence represented in SEQ ID No: 5, SEQ ID No: 6, SEQ ID No: 7 or SEQ ID No: 8 are of course also within the scope of the invention, as are nucleic acids identical in sequence with the enumerated HIP sequence of the Sequence listing. In one embodiment, the nucleic acid is a cDNA encoding a polypeptide having at least one activity of the subject HIP polypeptide.

In certain preferred embodiments, the invention features a purified or recombinant HIP polypeptide having peptide chain with a molecular weight in the range of 68 kd to 88 kd, even more preferably in the range of 76 kd to 80 kd (for a full-length HIP protein). It will be understood that certain post-translational modifications, e.g., glycosylation, phosphorylation and the like, can increase the apparent molecular weight of the HIP protein relative to the unmodified polypeptide chain, and cleavage of certain sequences, such as pro-sequences, can likewise decrease the apparent molecular weight. Other preferred HIP polypeptides include: a mature HIP polypeptide which lacks the signal sequence peptide, e.g., corresponding to residues 16-700 of SEQ ID No: 5, e.g., having a molecular weight of about 76.8 kD; a mature, extracellular fragment (soluble) of the receptor, e.g., corresponding to residues 16-356 of SEQ ID No: 5, e.g., having a molecular weight of about 74.4 kD; or, e.g., corresponding to residues 16-679 of SEQ ID No: 5, e.g., having a molecular weight of about 38.6 kD. In a preferred embodiments, the nucleic acid encodes a HIP polypeptide which includes the hedgehog binding domain. By a "molecular weight of about" it is meant with in about ±5 kd.

Another aspect of the invention provides a nucleic acid which hybridizes under high or low stringency conditions to one or more of the nucleic acids represented by SEQ ID Nos: 1-4 and 9-14. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Nucleic acids, having a sequence that differs from the nucleotide sequences shown in SEQ ID No: 1, SEQ ID No: 2, SEQ ID No: 3 or SEQ ID No: 4 due to degeneracy in the genetic code are also within the scope of the invention. Such nucleic acids encode functionally equivalent peptides (i.e., a peptide having a biological activity of a HIP polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of a HIP polypeptide. However, it is expected that DNA sequence polymorphisms that do lead to changes in the amino acid sequences of the subject HIP polypeptides will exist among, for example, humans. One skilled in the art will appreciate that these variations in one or more nucleotides (up to about 3-5% of the nucleotides) of the nucleic acids encoding polypeptides having an activity of a HIP polypeptide may exist among individuals of a given species due to natural allelic variation.

As used herein, a HIP gene fragment refers to a nucleic acid having fewer nucleotides than the nucleotide sequence encoding the entire mature form of a HIP protein yet which (preferably) encodes a polypeptide which retains some biological activity of the full length protein. Fragment sizes contemplated by the present invention include, for example, 5, 10, 25, 50, 75, 100, or 200 amino acids in length. In a preferred embodiment of a truncated receptor, the polypeptide will include all or a sufficient portion of the ligand domain to bind to a hedgehog polypeptide.

As indicated by the examples set out below, HIP protein-encoding nucleic acids can be obtained from mRNA present in cells of metazoan organisms. It should also be possible to obtain nucleic acids encoding HIP polypeptides of the present invention from genomic DNA from both adults and embryos. For example, a gene encoding a HIP protein can be cloned from either a cDNA or a genomic library in accordance with protocols described herein, as well as those generally known to persons skilled in the art. A cDNA encoding a HIP protein can be obtained by isolating total mRNA from a cell, such as a mammalian cell, e.g. a human cell, as desired. Double stranded cDNAs can be prepared from the total mRNA, and subsequently inserted into a suitable plasmid or bacteriophage vector using any one of a number of known techniques. The gene encoding a HIP protein can also be cloned using established polymerase chain reaction techniques in accordance with the nucleotide sequence information provided by the invention. The nucleic acid of the invention can be DNA or RNA. A preferred nucleic acid is a cDNA including a nucleotide sequence represented by any one of SEQ ID No: 1, SEQ ID No: 2, SEQ ID No: 3, SEQ ID No: 4, SEQ ID No: 9, SEQ ID No: 10, or SEQ ID No: 11, SEQ ID No: 12, SEQ ID No: 13 or SEQ ID No: 14.

Another aspect of the invention relates to the use of the isolated nucleic acid in "antisense" therapy. As used herein, "antisense" therapy refers to administration or in situ generation of oligonucleotide probes or their derivatives which specifically hybridize (e.g. binds) under cellular conditions, with the cellular mRNA and/or genomic DNA encoding a subject HIP protein so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a HIP protein. Alternatively, the antisense construct is an oligonucleotide probe which is generated ex vivo and which, when introduced into the cell causes inhibition of expression by hybridizing with the mRNA and/or genomic sequences of a HIP gene. Such oligonucleotide probes are preferably modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775), or peptide nucleic acids (PNAs). Additionally, general approaches to constructing oligomers useful in antisense therapy have been reviewed, for example, by Van der Krol et al. (1988) Biotechniques 6:958-976; and Stein et al. (1988) Cancer Res 48:2659-2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of routes of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as generally known in the art.

In addition to use in therapy, the oligomers of the invention may be used as diagnostic reagents to detect the presence or absence of the target DNA or RNA sequences to which they specifically bind. Such diagnostic tests are described in further detail below.

Likewise, the antisense constructs of the present invention, by antagonizing the normal biological activity of a HIP protein, e.g., by reducing the level of its expression, can be used in the manipulation of tissue, e.g. tissue maintenance, differentiation or growth, both in vivo and ex vivo.

Furthermore, the anti-sense techniques (e.g. microinjection of antisense molecules, or transfection with plasmids whose transcripts are anti-sense with regard to a HIP mRNA or gene sequence) can be used to investigate the role of HIP in developmental events, as well as the normal cellular function of HIP in adult tissue. Such techniques can be utilized in cell culture, but can also be used in the creation of transgenic animals (described infra).

This invention also provides expression vectors containing a nucleic acid encoding a HIP polypeptide, operably linked to at least one transcriptional regulatory sequence. Operably linked is intended to mean that the nucleotide sequence is linked to a regulatory sequence in a manner which allows expression of the nucleotide sequence. Regulatory sequences are art-recognized and are selected to direct expression of the subject HIP proteins. Accordingly, the term transcriptional regulatory sequence includes promoters, enhancers and other expression control elements. Such regulatory sequences are described in Goeddel; Gene Expression Technology: Methods in Enzymology 185, Academic Press, San Diego, Calif. (1990). For instance, any of a wide variety of expression control sequences, sequences that control the expression of a DNA sequence when operatively linked to it, may be used in these vectors to express DNA sequences encoding HIP polypeptides of this invention. Such useful expression control sequences, include, for example, a viral LTR, such as the LTR of the Moloney murine leukemia virus, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage λ, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed.

Moreover, the vector's copy number, the ability to control that copy number and the expression of any other proteins encoded by the vector, such as antibiotic markers, should also be considered. In one embodiment, the expression vector includes a recombinant gene encoding a polypeptide having an agonistic activity of a subject HIP polypeptide, or alternatively, encoding a polypeptide which is an antagonistic form of the HIP protein. An exemplary HIP polypeptide of the present invention is a soluble truncated form of the protein which retains the ligand binding domain, e.g., retains the ability to bind to hedgehog polypeptides. Such expression vectors can be used to transfect cells and thereby produce polypeptides, including fusion proteins, encoded by nucleic acids as described herein.

Moreover, the gene constructs of the present invention can also be used as a part of a gene therapy protocol to deliver nucleic acids, e.g., encoding either an agonistic or antagonistic form of a subject HIP proteins or an antisense molecule described above. Thus, another aspect of the invention features expression vectors for in vivo or in vitro transfection and expression of a HIP polypeptide or antisense molecule in particular cell types so as to reconstitute the function of, or alternatively, abrogate all or a portion of the biological function of HIP-induced transcription in a tissue in which the naturally-occurring form of the protein is misexpressed (or has been disrupted); or to deliver a form of the protein which alters maintenance or differentiation of tissue, or which inhibits neoplastic or hyperplastic proliferation.

Expression constructs of the subject HIP polypeptides, as well as antisense constructs, may be administered in any biologically effective carrier, e.g. any formulation or composition capable of effectively delivering the recombinant gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically. Furthermore, it will be recognized that the particular gene construct provided for in vivo transduction of HIP expression are also useful for in vitro transduction of cells, such as for use in the ex vivo tissue culture systems described below.

A preferred approach for in vivo introduction of nucleic acid into a cell is by use of a viral vector containing nucleic acid, e.g. a cDNA encoding the particular HIP polypeptide desired. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid. Retrovirus vectors, adenovirus vectors and adeno-associated virus vectors are exemplary recombinant gene delivery system for the transfer of exogenous genes in vivo, particularly into humans. These vectors provide efficient delivery of genes into cells, and the transferred nucleic acids are stably integrated into the chromosomal DNA of the host.

In addition to viral transfer methods, such as those illustrated above, non-viral methods can also be employed to cause expression of a subject HIP polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject HIP polypeptide gene by the targeted cell. Exemplary gene delivery systems of this type include liposomal derived systems, poly-lysine conjugates, and artificial viral envelopes.

In clinical settings, the gene delivery systems for the therapeutic HIP gene can be introduced into a patient-animal by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054-3057). A HIP gene can be delivered in a gene therapy construct by electroporation using techniques described, for example, by Dev et al. ((1994) Cancer Treat Rev 20:105-115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

In yet another embodiment, the subject invention provides a "gene activation" construct which, by homologous recombination with a genomic DNA, alters the transcriptional regulatory sequences of an endogenous HIP gene. For instance, the gene activation construct can replace the endogenous promoter of a HIP gene with a heterologous promoter, e.g., one which causes constitutive expression of the HIP gene or which causes inducible expression of the gene under conditions different from the normal expression pattern of HIP. A variety of different formats for the gene activation constructs are available. See, for example, the Transkaryotic Therapies, Inc PCT publications WO93/09222, WO95/31560, WO96/29411, WO95/31560 and WO94/12650.

In preferred embodiments, the nucleotide sequence used as the gene activation construct can be comprised of (1) DNA from some portion of the endogenous HIP gene (exon sequence, intron sequence, promoter sequences, etc.) which direct recombination and (2) heterologous transcriptional regulatory sequence(s) which is to be operably linked to the coding sequence for the genomic HIP gene upon recombination of the gene activation construct. For use in generating cultures of HIP producing cells, the construct may further include a reporter gene to detect the presence of the knockout construct in the cell.

The gene activation construct is inserted into a cell, and integrates with the genomic DNA of the cell in such a position so as to provide the heterologous regulatory sequences in operative association with the native HIP gene. Such insertion occurs by homologous recombination, i.e., recombination regions of the activation construct that are homologous to the endogenous HIP gene sequence hybridize to the genomic DNA and recombine with the genomic sequences so that the construct is incorporated into the corresponding position of the genomic DNA.

The terms "recombination region" or "targeting sequence" refer to a segment (i.e., a portion) of a gene activation construct having a sequence that is substantially identical to or substantially complementary to a genomic gene sequence, e.g., including 5' flanking sequences of the genomic gene, and can facilitate homologous recombination between the genomic sequence and the targeting transgene construct.

As used herein, the term "replacement region" refers to a portion of a activation construct which becomes integrated into an endogenous chromosomal location following homologous recombination between a recombination region and a genomic sequence.

The heterologous regulatory sequences, e.g., which are provided in the replacement region, can include one or more of a variety elements, including: promoters (such as constitutive or inducible promoters), enhancers, negative regulatory elements, locus control regions, transcription factor binding sites, or combinations thereof. Promoters/enhancers which may be used to control the expression of the targeted gene in vivo include, but are not limited to, the cytomegalovirus (CMV) promoter/enhancer (Karasuyama et al., 1989, *J. Exp. Med.,* 169:13), the human β-actin promoter (Gunning et al. (1987) *PNAS* 84:4831-4835), the glucocorticoid-inducible promoter present in the mouse mammary tumor virus long terminal repeat (MMTV LTR) (Klessig et al. (1984) *Mol. Cell Biol.* 4:1354-1362), the long terminal repeat sequences of Moloney murine leukemia virus (MuLV LTR) (Weiss et al. (1985) *RNA Tumor Viruses*, Cold Spring Harbor Laboratory, Cold Spring Harbor, N.Y.), the SV40 early or late region promoter (Bemoist et al. (1981) *Nature* 290:304-310; Templeton et al. (1984) *Mol. Cell Biol.,* 4:817; and Sprague et al. (1983) *J. Virol.,* 45:773), the promoter contained in the 3' long terminal repeat of Rous sarcoma virus (RSV) (Yamamoto et al., 1980, *Cell,* 22:787-797), the herpes simplex virus (HSV) thymidine kinase promoter/enhancer (Wagner et al. (1981) *PNAS* 82:3567-71), and the herpes simplex virus LAT promoter (Wolfe et al. (1992) *Nature Genetics,* 1:379-384).

In still other embodiments, the replacement region merely deletes a negative transcriptional control element of the native gene, e.g., to activate expression, or ablates a positive control element, e.g., to inhibit expression of the targeted gene.

Another aspect of the present invention concerns recombinant forms of the HIP proteins. Recombinant polypeptides preferred by the present invention, in addition to native HIP proteins, are at least 60% or 70% homologous, more preferably at least 80% homologous and most preferably at least 85% homologous with an amino acid sequence represented by one or more of SEQ ID Nos: 5, SEQ ID No: 6, SEQ ID No: 7 and SEQ ID No: 8. Polypeptides which possess an activity of a HIP protein (i.e. either agonistic or antagonistic), and which are at least 90%, more preferably at least 95%, and most preferably at least about 98-99% homologous with SEQ ID No: 5, SEQ ID No: 6, SEQ ID No: 7 and/or SEQ ID No: 8 are also within the scope of the invention. Such polypeptides, as described above, include various truncated forms of the protein.

The term "recombinant HIP polypeptide" refers to a polypeptide which is produced by recombinant DNA techniques, wherein generally, DNA encoding a HIP polypeptide is inserted into a suitable expression vector which is in turn used to transform a host cell to produce the heterologous protein. Moreover, the phrase "derived from", with respect to a recombinant HIP gene, is meant to include within the meaning of "recombinant protein" those proteins having an amino acid sequence of a native HIP protein, or an amino acid sequence similar thereto which is generated by mutations including substitutions and deletions (including truncation) of a naturally occurring form of the protein.

The present invention further pertains to recombinant forms of the subject HIP polypeptides which are encoded by genes derived from a mammal (e.g. a human), reptile or amphibian and which have amino acid sequences evolutionarily related to the HIP protein represented in SEQ ID No: 5, SEQ ID No: 6, SEQ ID No: 7 and SEQ ID No: 8. Such recombinant HIP polypeptides preferably are capable of functioning in one of either role of an agonist or antagonist of at least one biological activity of a wild-type ("authentic") HIP protein of the appended sequence listing. The term "evolutionarily related to", with respect to amino acid sequences of HIP proteins, refers to both polypeptides having amino acid sequences which have arisen naturally, and also to mutational variants of HIP polypeptides which are derived, for example, by combinatorial mutagenesis.

The present invention also provides methods of producing the subject HIP polypeptides. For example, a host cell transfected with a nucleic acid vector directing expression of a nucleotide sequence encoding the subject polypeptides can be cultured under appropriate conditions to allow expression of the peptide to occur. If the recombinant protein is not provided with a secretion signal peptide, such as in the case of a GST fusion protein, the cells may be harvested, lysed and the protein isolated. A cell culture includes host cells, media and other byproducts. Suitable media for cell culture are well known in the art. The recombinant HIP polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant HIP polypeptide is a fusion protein containing a domain which facilitates its purification, such as GST fusion protein or poly(His) fusion protein.

This invention also pertains to a host cell transfected to express recombinant forms of the subject HIP polypeptides. The host cell may be any eukaryotic or prokaryotic cell. Thus, a nucleotide sequence derived from the cloning of HIP proteins, encoding all or a selected portion of a full-length protein, can be used to produce a recombinant form of a HIP polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. hedgehog proteins, TGFβ proteins, as well as a wide range of receptors. Similar procedures, or modifications thereof, can be employed to prepare recombinant HIP polypeptides by microbial means or tissue-culture technology in accord with the subject invention.

The recombinant HIP genes can be produced by ligating nucleic acid encoding a HIP polypeptide into a vector suitable for expression in either prokaryotic cells, eukaryotic cells, or both. Expression vectors for production of recombinant forms of the subject HIP polypeptides include plasmids and other vectors. For instance, suitable vectors for the expression of a HIP polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in Experimental Manipulation of Gene Expression, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. In an illustrative embodiment, a HIP polypeptide is produced recombinantly utilizing an expression vector generated by sub-cloning the coding sequence of a HIP gene represented in SEQ ID No: 1, SEQ ID No: 2, SEQ ID No: 3 or SEQ ID No: 4.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17.

In some instances, it may be desirable to express the recombinant HIP polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When it is desirable to express only a portion of a HIP protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) J. Bacteriol. 169:751-757) and *Salmonella typhimurium* and its in vitro activity has been demonstrated on recombinant proteins (Miller et al. (1987) PNAS 84:2718-1722). Therefore, removal of an N-terminal methionine, if desired, can be achieved either in vivo by expressing HIP-derived polypeptides in a host which produces MAP (e.g., *E. coli* or CM89 or *S. cerevisiae*), or in vitro by use of purified MAP (e.g., procedure of Miller et al., supra).

Alternatively, the coding sequences for the polypeptide can be incorporated as a part of a fusion gene including a nucleotide sequence encoding a different polypeptide. This type of expression system can be useful under conditions where it is desirable to produce an immunogenic fragment of a HIP protein. For example, the VP6 capsid protein of rotavirus can be used as an immunologic carrier protein for portions of the HIP polypeptide, either in the monomeric form or in the form of a viral particle. The nucleic acid sequences corresponding to the portion of a subject HIP protein to which antibodies are to be raised can be incorporated into a fusion gene construct which includes coding sequences for a late vaccinia virus structural protein to produce a set of recombinant viruses expressing fusion proteins comprising HIP epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of a HIP protein and the poliovirus capsid protein can be created to enhance immunogenicity of the set of polypeptide antigens (see, for example, EP Publication No: 0259149; and Evans et al. (1989) Nature 339:385; Huang et al. (1988) J. Virol. 62:3855; and Schlienger et al. (1992) J. Virol. 66:2).

The Multiple Antigen Peptide system for peptide-based immunization can also be utilized to generate an immunogen, wherein a desired portion of a HIP polypeptide is obtained directly from organo-chemical synthesis of the peptide onto an oligomeric branching lysine core (see, for example, Posnett et al. (1988) JBC 263:1719 and Nardelli et al. (1992) J. Immunol. 148:914). Antigenic determinants of HIP proteins can also be expressed and presented by bacterial cells.

In addition to utilizing fusion proteins to enhance immunogenicity, it is widely appreciated that fusion proteins can also facilitate the expression of proteins, and accordingly, can be used in the expression of the HIP polypeptides of the present invention, particularly truncated forms of the HIP protein. For example, HIP polypeptides can be generated as glutathione-S-transferase (GST-fusion) proteins. Such GST-fusion proteins can enable easy purification of the HIP polypeptide, as for example by the use of glutathione-derivatized matrices (see, for example, Current Protocols in Molecular Biology, eds. Ausubel et al. (N.Y.: John Wiley & Sons, 1991)).

In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a Ni2+ metal resin. The purification leader sequence can then be subsequently removed by treatment with enterokinase to provide the purified protein (e.g., see Hochuli et al. (1987) J. Chromatography 411:177; and Janknecht et al. PNAS 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al. John Wiley & Sons: 1992).

The HIP polypeptides may also be chemically modified to create HIP derivatives by forming covalent or aggregate conjugates with other chemical moieties, such as glycosyl groups, lipids, cholesterol, phosphate, acetyl groups and the like. Covalent derivatives of HIP proteins can be prepared by linking the chemical moieties to functional groups on amino acid sidechains of the protein or at the N-terminus or at the C-terminus of the polypeptide.

As appropriate, formulations of multimeric HIP polypeptides are also provided. The multimers of the soluble forms of the subject HIP polypeptides may be produced according to the methods known in the art. In one embodiment, the HIP multimers are cross-linked chemically by using known methods which will result in the formation of either dimers or higher multimers of the soluble forms of the HIP polypeptides. Another way of producing the multimers of the soluble forms of the HIP polypeptides is by recombinant techniques, e.g., by inclusion of hinge regions. This linker can facilitate enhanced flexibility of the chimeric protein allowing the various HIP monomeric subunits to freely and (optionally) simultaneously interact with a HIP ligand by reducing steric hindrance between the two fragments, as well as allowing appropriate folding of each portion to occur. The linker can be of natural origin, such as a sequence determined to exist in random coil between two domains of a protein. Alternatively, the linker can be of synthetic origin. For instance, the sequence $(Gly_4Ser)_3$ can be used as a synthetic unstructured linker. Linkers of this type are described in Huston et al. (1988) PNAS 85:4879; and U.S. Pat. Nos. 5,091,513 and 5,258,498. Naturally occurring unstructured linkers of human origin are preferred as they reduce the risk of immunogenicity.

Each multimer comprises two or more monomers, each comprising the soluble form of a HIP polypeptide or a salt or functional derivative thereof. The upper limit for the number of monomers in a multimer is not important and liposomes having many such monomers thereon may be used. Such multimers preferably have 2-5 monomers and more preferably 2 or 3.

The present invention also makes available isolated HIP polypeptides which are isolated from, or otherwise substantially free of other cellular proteins, especially receptors and/or other inductive polypeptides which may normally be associated with the HIP polypeptide. The term "substantially free of other cellular proteins" (also referred to herein as "contaminating proteins") or "substantially pure or purified preparations" are defined as encompassing preparations of HIP polypeptides having less than 20% (by dry weight) contaminating protein, and preferably having less than 5% contaminating protein. Functional forms of the subject polypeptides can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins. The term "purified" as used herein preferably means at least 80% by dry weight, more preferably in the range of 95-99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions. In preferred embodiments, purified HIP preparations will lack any contaminating proteins from the same animal from that HIP is normally produced, as can be accomplished by recombinant expression of, for example, a mammalian HIP protein in a yeast or bacterial cell.

As described above for recombinant polypeptides, isolated HIP polypeptides can include all or a portion of an amino acid sequences corresponding to a HIP polypeptide represented in SEQ ID No: 5, SEQ ID No: 6, SEQ ID No: 7 and SEQ ID No: 8 or homologous sequences thereto.

Isolated peptidyl portions of HIP proteins can also be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a HIP polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") HIP protein. For example, Roman et al. (1994) *Eur J Biochem* 222:65-73 describe the use of competitive-binding assays using short, overlapping synthetic peptides from larger proteins to identify binding domains.

The recombinant HIP polypeptides of the present invention also include homologs of the authentic HIP proteins, such as versions of those protein which are resistant to proteolytic cleavage, as for example, due to mutations which alter ubiquitination, prenylation or the like, enzymatic release of the extracellular domain, or other enzymatic targeting associated with the protein.

Modification of the structure of the subject HIP polypeptides can be for such purposes as enhancing therapeutic or prophylactic efficacy, stability (e.g., ex vivo shelf life and resistance to proteolytic degradation in vivo), or post-translational modifications. Such modified peptides, when designed to retain at least one activity of the naturally-occurring form of the protein, or to produce specific antagonists thereof, are considered functional equivalents of the HIP polypeptides (though they may be agonistic or antagonistic of the bioactivities of the authentic protein). Such modified peptides can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids are can be divided into four families: (1) acidic aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine (see, for example, Biochemistry, 2nd ed., Ed. by L. Stryer, WH Freeman and Co.: 1981). Whether a change in the amino acid sequence of a peptide results in a functional HIP homolog (e.g. functional in the sense that the resulting polypeptide mimics or antagonizes the authentic form) can be readily determined by assessing the ability of the variant peptide to produce a response in cells in a fashion similar to the wild-type protein, or competitively inhibit such a response. Polypeptides in which more than one replacement has taken place can readily be tested in the same manner.

In one aspect of this method, the amino acid sequences for a population of HIP homologs from different species or other related proteins are aligned, preferably to promote the highest homology possible. Such a population of variants can include, for example, HIP homologs from one or more species. Amino acids which appear at each position of the aligned sequences are selected to create a degenerate set of combinatorial sequences. In a preferred embodiment, the variegated library of HIP variants is generated by combinatorial mutagenesis at the nucleic acid level, and is encoded by a variegated gene library. For instance, a mixture of synthetic oligonucleotides can be enzymatically ligated into gene sequences such that the degenerate set of potential HIP sequences are expressible as individual polypeptides, or alternatively, as a set of larger fusion proteins (e.g. for phage display) containing the set of HIP sequences therein.

In an illustrative embodiment, the full-length sequences aligned in FIG. 1 are compared in order to generate a degenerate library of potential HIP agonists and antagonists. For instance, a library of HIP polypeptides can be generated to include a degenerate core polypeptide sequence represented by the general formula:

```
LXFFEGDAKFGEXXXXSGARRRRCLNGXPXXXXXXRXRXXXXXXXXXXGGXXXXXCXGXYP  (SEQ ID No. 15)

RXSCCXXXDXXGLXXXXXKIXSXTNNXECXXLLEEIXCAXCSPHXQXLFXTPEXXXXXXXX

XXLPXLCKDYCKEFFYTCRGHIPGXLQTTADEFCFYYARKDXGLCFPDFPRKQVRGPASNY

LXXMEXYXKXXXISRKHKHNCXCXQEVXSGLRQPVXAXHXGDGXXRLFILEKEGYVKIXXP

EGXXXKEPXLDIHKLVQSGIKGGDERGLLSLAFHPNYKKNGKLYVSYTTNQERWAIGPHDH

ILRVVEYTVSRKNPXQVDXRTARXFLEVAELHRKHLGGQLLFGPDGFLYXXLGDGMITLDD

MEEMDGLSDFTGSVLRLDVXTDXCXVPYSIPRSNPHFNSTNQPPEXFAHGLHXPGRCAVDX

HPTDXNINLTILCSDSNGKNRSSARILQIIKGRDYESEPSLLEFKPFSXGXLVGGFVYRGC

QSERLYGSYVFGDRNGNFLTLQQXPXTKQWQEKPLCLGXSXSCRGXFSGXXLGFGEDELGE

XYILSSSKSMTQTHNGKLYKIXDPKRPLXPEECXXTXXXAQXLTSXCSRXCRNGXXTPTGK

CCCXXGWEGXFCRXAKCXPACRHGGVCVRPNKCLCKKGYLGPQCEQ
```

This invention further contemplates a method for generating sets of combinatorial point mutants of the subject HIP proteins as well as truncation mutants, and is especially useful for identifying potential variant sequences (e.g. homologs) that are functional in modulating signal transduction and/or ligand binding. The purpose of screening such combinatorial libraries is to generate, for example, novel HIP homologs which can act as either agonists or antagonist, or alternatively, possess novel activities all together. To illustrate, HIP homologs can be engineered by the present method to provide selective, constitutive activation of hedgehog activity, or alternatively, to be dominant negative inhibitors of HIP-dependent signal transduction. For instance, mutagenesis can provide HIP homologs which are able to bind extracellular ligands yet be unable to bind or signal through intracellular regulatory proteins.

where each occurrence of X is, independently, any (natural) amino acid residue, though more preferably is an amino acid residue (or gap) selected from those residues occurring at the corresponding position in the mouse, human or chicken proteins shown in FIG. 1 or a conservative substitution therefor, and even more preferably is an amino acid residue (or gap) selected from those residues occurring at the corresponding position in the mouse, human or chicken proteins shown in FIG. 1. As appropriate for the screening assay, the polypeptides of the library can include a secretion signal sequence and/or a C-terminal membrane anchor sequence derived from one of the HIP proteins.

In another embodiment, the degenerate library is based on comparison of the human and mouse sequences, and may include a degenerate core polypeptide sequence represented by the general formula:

```
LGFFEGDAKFGERXEGSGARRRRCLNGNPPKRLKRRDRRXMSQLELLSGGEXLCGGFYPRX  (SEQ ID No. 16)

SCCLXSDSPGLGRLENKIFSXTNNXECXXLLEEIXCAXCSPHSQSLFXXPERXVLXXDXXL

PLLCKDYCKEFFYTCRGHIPGXLQTTADEFCFYYARKDXGLCFPDFPRKQVRGPASNYLXQ
```

-continued

```
MEXYXKVXXISRKHKHNCXCXQEVXSGLRQPVXAXHSGDGSXRLFILEKEGYVKILTPEGE

XFKEPYLDIHKLVQSGIKGGDERGLLSLAFHPNYKKNGKLYVSYTTNQERWAIGPHDHILR

VVEYTVSRKNPHQVDXRTARXFLEVAELHRKHLGGQLLFGPDGFLYIILGDGMITLDDMEE

MDGLSDFTGSVLRLDVDTDMCNVPYSIPRSWPHFNSTNQPPEVFAHGLHDPGRCAVDRHPT

DININLTILCSDSNGKNRSSARILQIIKGRDYESEPSLLEFKPFSNGPLVGGFVYRGCQSE

RLYGSYVFGDRNGNFLTLQQSPVTKQWQEKPLCLGXSXSCRGYFSGHILGFGEDELGEVYI

LSSSKSMTQTHNGKLYKIVDPKRPLMPEECRXTVQPAQXLTSXCSRLCRNGYXTPTGKCCC

SPGWEGDFCRXAKCEPACRHGGVCVRPNKCLCKKGYLGPQCEQVDRNXRRVTR
```

where each occurrence of X is, independently, any (natural) amino acid residue, though more preferably is an amino acid residue (or gap) selected from those residues occurring at the corresponding position in the mouse or human proteins shown in FIG. 1 or a conservative substitution therefor, and even more preferably is an amino acid residue (or gap) selected from those residues occurring at the corresponding position in the mouse or human proteins shown in FIG. 1.

There are many ways by which such libraries of potential HIP homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential HIP sequences. The synthesis of degenerate oligonucleotides is well known in the art (see for example, Narang, S A (1983) Tetrahedron 39:3; Itakura et al. (1981) Recombinant DNA, Proc 3rd Cleveland Sympos. Macromolecules, ed. AG Walton, Amsterdam: Elsevier pp 273-289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386-390; Roberts et al. (1992) PNAS 89:2429-2433; Devlin et al. (1990) Science 249: 404-406; Cwirla et al. (1990) PNAS 87: 6378-6382; as well as U.S. Pat. Nos. 5,223,409, 5,198,346, and 5,096,815).

Likewise, a library of coding sequence fragments can be provided for a HIP clone in order to generate a variegated population of HIP fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of a HIP coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of HIP homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

In an exemplary embodiment, a library of HIP variants is expressed as a fusion protein on the surface of a viral particle, and the viral particles panned on a hedgehog matrix. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd., and fl are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) *J. Biol. Chem.* 267:16007-16010; Griffiths et al. (1993) *EMBO J.* 12:725-734; Clackson et al. (1991) *Nature* 352:624-628; and Barbas et al. (1992) *PNAS* 89:4457-4461). For example, the recombinant phage antibody system (RPAS, Pharmacia Catalog number 27-9400-01) can be easily modified for use in expressing and screening HIP combinatorial libraries by panning on a matrix-immobilized hedgehog polypeptides to enrich for HIP homologs with enhanced ability to bind the ligand.

The invention also provides for reduction of the HIP protein to generate mimetics, e.g. peptide or non-peptide agents, which are able to disrupt a biological activity of a HIP polypeptide of the present invention, e.g. as inhibitors of protein-protein interactions, such as with ligand proteins. Thus, such mutagenic techniques as described above are also useful to map the determinants of the HIP proteins which participate in protein-protein interactions involved in, for example, interaction of the subject HIP polypeptide with hedgehog polypeptides. Alternatively, a similar system can be used to derive fragments of a hedgehog protein which bind to a HIP protein and competitively inhibit binding of the full length hedgehog protein.

To further illustrate, the critical residues of either a HIP protein or a hedgehog protein which are involved in molecular recognition of the other can be determined and used to generate HIP-derived or hedgehog-derived peptidomimetics which competitively inhibit Hedgehog/HIP protein interactions. By employing, for example, scanning mutagenesis to map the amino acid residues of a protein which is involved in binding other proteins, peptidomimetic compounds can be generated which mimic those residues which facilitate the interaction. Such mimetics may then be used to interfere with the normal function of a HIP protein (or its ligand). For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) *J Med Chem* 29:295; and Ewenson et al. in Peptides: Structure and Function (Proceedings of the 9th American Peptide Symposium) Pierce Chemical Co. Rockland, Ill., 1985), b-turn dipeptide cores (Nagai et al. (1985) *Tetrahedron Lett* 26:647; and Sato et al. (1986) *J Chem Soc Perkin Trans* 1:1231), and b-aminoalcohols (Gordon et al. (1985) *Biochem Biophys Res Commun* 126:419; and Dann et al. (1986) *Biochem Biophys Res Commun* 134:71).

Another aspect of the invention pertains to an antibody specifically reactive with a HIP protein. For example, by using immunogens derived from a HIP protein, e.g. based on the cDNA sequences, anti-protein/anti-peptide antisera or monoclonal antibodies can be made by standard protocols (See, for example, Antibodies: A Laboratory Manual ed. by Harlow and Lane (Cold Spring Harbor Press: 1988)). A mammal, such as a mouse, a hamster or rabbit can be immunized with an immunogenic form of the peptide (e.g., a HIP polypeptide or an antigenic fragment which is capable of eliciting an antibody response). Techniques for conferring immunogenicity on a protein or peptide include conjugation to carriers or other techniques well known in the art. An immunogenic portion of a HIP protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a HIP protein of a organism, such as a mammal, e.g. antigenic determinants of a protein represented by SEQ ID No: 5, SEQ ID No: 6, SEQ ID No: 7 and SEQ ID No: 8 or closely related homologs (e.g. at least 70% homologous, preferably at least 80% homologous, and more preferably at least 90% homologous). In yet a further preferred embodiment of the present invention, in order to provide, for example, antibodies which are immunoselective for discrete HIP homologs the anti-HIP polypeptide antibodies do not substantially cross react (i.e. does not react specifically) with a protein which is, for example, less than 85%, 90% or 95% homologous with the selected HIP. By "not substantially cross react", it is meant that the antibody has a binding affinity for a non-homologous protein which is at least one order of magnitude, more preferably at least 2 orders of magnitude, and even more preferably at least 3 orders of magnitude less than the binding affinity of the antibody for the intended target HIP.

Following immunization of an animal with an antigenic preparation of a HIP polypeptide, anti-HIP antisera can be obtained and, if desired, polyclonal anti-HIP antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with a HIP polypeptide of the present invention and monoclonal antibodies isolated from a culture comprising such hybridoma cells.

The term antibody as used herein is intended to include fragments thereof which are also specifically reactive with a HIP polypeptide. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific and chimeric molecules having affinity for a HIP protein conferred by at least one CDR region of the antibody.

Both monoclonal and polyclonal antibodies (Ab) directed against authentic HIP polypeptides, or HIP variants, and antibody fragments such as Fab, $F(ab)_2$, Fv and scFv can be used to block the action of a HIP protein and allow the study of the role of these proteins in, for example, differentiation of tissue. Experiments of this nature can aid in deciphering the role of HIP proteins that may be involved in control of proliferation versus differentiation, e.g., in patterning and tissue formation.

Antibodies which specifically bind HIP epitopes can also be used in immunohistochemical staining of tissue samples in order to evaluate the abundance and pattern of expression of each of the subject HIP polypeptides. Anti-HIP antibodies can be used diagnostically in immuno-precipitation and immuno-blotting to detect and evaluate HIP protein levels in tissue as part of a clinical testing procedure. For instance, such measurements can be useful in predictive valuations of the onset or progression of proliferative or differentiative disorders. Likewise, the ability to monitor HIP protein levels in an individual can allow determination of the efficacy of a given treatment regimen for an individual afflicted with such a disorder. The level of HIP polypeptides may be measured from cells in bodily fluid, such as in samples of cerebral spinal fluid or amniotic fluid, or can be measured in tissue, such as produced by biopsy. Diagnostic assays using anti-HIP antibodies can include, for example, immunoassays designed to aid in early diagnosis of a disorder, particularly ones which are manifest at birth. Diagnostic assays using anti-HIP polypeptide antibodies can also include immunoassays designed to aid in early diagnosis and phenotyping neoplastic or hyperplastic disorders.

Another application of anti-HIP antibodies of the present invention is in the immunological screening of cDNA libraries constructed in expression vectors such as λgt11, λgt18-23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a HIP protein, e.g. orthologs of the HIP protein from other species, can then be detected with antibodies, as, for example, reacting nitrocellulose filters lifted from infected plates with anti-HIP antibodies. Positive phage detected by this assay can then be isolated from the infected plate. Thus, the presence of HIP homologs can be detected and cloned from other animals, as can alternate isoforms (including splicing variants) from humans.

Moreover, the nucleotide sequences determined from the cloning of HIP genes from organisms will further allow for the generation of probes and primers designed for use in identifying and/or cloning HIP homologs in other cell types, e.g. from other tissues, as well as HIP homologs from other organisms. For instance, the present invention also provides a probe/primer comprising a substantially purified oligonucleotide, which oligonucleotide comprises a region of nucleotide sequence that hybridizes under stringent conditions to at least 15 consecutive nucleotides of sense or anti-sense sequence selected from the group consisting of SEQ ID No: 1, SEQ ID No: 2, SEQ ID No: 3 or SEQ ID No: 4 or naturally occurring mutants thereof. For instance, primers based on the nucleic acid represented in SEQ ID No: 1, SEQ ID No: 2, SEQ ID No: 3 or SEQ ID No: 4, can be used in PCR reactions to clone HIP homologs. Likewise, probes based on the subject HIP sequences can be used to detect transcripts or genomic sequences encoding the same or homologous proteins. In preferred embodiments, the probe further comprises a label group attached thereto and able to be detected, e.g. the label group is selected from amongst radioisotopes, fluorescent compounds, enzymes, and enzyme co-factors.

Such probes can also be used as a part of a diagnostic test kit for identifying cells or tissue which misexpress a HIP protein, such as by measuring a level of a HIP-encoding nucleic acid in a sample of cells from a patient-animal; e.g. detecting HIP mRNA levels or determining whether a genomic HIP gene has been mutated or deleted.

To illustrate, nucleotide probes can be generated from the subject HIP genes which facilitate histological screening of intact tissue and tissue samples for the presence (or absence) of HIP-encoding transcripts. Similar to the diagnostic uses of anti-HIP antibodies, the use of probes directed to HIP messages, or to genomic HIP sequences, can be used for both predictive and therapeutic evaluation of allelic mutations which might be manifest in, for example, degenerative disorders marked by loss of particular cell-types, apoptosis, neoplastic and/or hyperplastic disorders (e.g. unwanted cell growth) or abnormal differentiation of tissue. Used in conjunction with immunoassays as described above, the oligonucleotide probes can help facilitate the determination of the molecular basis for a developmental disorder which may involve some abnormality associated with expression (or lack thereof) of a HIP protein. For instance, variation in polypeptide synthesis can be differentiated from a mutation in a coding sequence.

Accordingly, the present method provides a method for determining if a subject is at risk for a disorder characterized by aberrant apoptosis, cell proliferation and/or differentiation. In preferred embodiments, method can be generally characterized as comprising detecting, in a sample of cells from the subject, the presence or absence of a genetic lesion characterized by at least one of (i) an alteration affecting the integrity of a gene encoding a HIP-protein, or (ii) the mis-expression of the HIP gene. To illustrate, such genetic lesions can be detected by ascertaining the existence of at least one of (i) a deletion of one or more nucleotides from a HIP gene, (ii) an addition of one or more nucleotides to a HIP gene, (iii) a substitution of one or more nucleotides of a HIP gene, (iv) a gross chromosomal rearrangement of a HIP gene, (v) a gross alteration in the level of a messenger RNA transcript of a HIP gene, (vii) aberrant modification of a HIP gene, such as of the methylation pattern of the genomic DNA, (vii) the presence of a non-wild type splicing pattern of a messenger RNA transcript of a HIP gene, (viii) a non-wild type level of a HIP-protein, and (ix) inappropriate post-translational modification of a HIP-protein. As set out below, the present invention provides a large number of assay techniques for detecting lesions in a HIP gene, and importantly, provides the ability to discern between different molecular causes underlying HIP-dependent aberrant cell growth, proliferation and/or differentiation.

In an exemplary embodiment, there is provided a nucleic acid composition comprising a (purified) oligonucleotide probe including a region of nucleotide sequence which is capable of hybridizing to a sense or antisense sequence of a HIP gene, such as represented by any one of SEQ ID Nos: 1-4 and 9-14, or naturally occurring mutants thereof, or 5' or 3' flanking sequences or intronic sequences naturally associated with the subject HIP genes or naturally occurring mutants thereof. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels.

In certain embodiments, detection of the lesion comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1944) PNAS 91:360-364), the later of which can be particularly useful for detecting point mutations in the HIP gene. In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a HIP gene under conditions such that hybridization and amplification of the HIP gene (if present) occurs, and (iv) detecting the presence or absence of an amplification product, or detecting the size of the amplification product and comparing the length to a control sample.

In still another embodiment, the level of a HIP-protein can be detected by immunoassay. For instance, the cells of a biopsy sample can be lysed, and the level of a HIP-protein present in the cell can be quantitated by standard immunoassay techniques. In yet another exemplary embodiment, aberrant methylation patterns of a HIP gene can be detected by digesting genomic DNA from a patient sample with one or more restriction endonucleases that are sensitive to methylation and for which recognition sites exist in the HIP gene (including in the flanking and intronic sequences). See, for example, Buiting et al. (1994) Human Mol Genet 3:893-895. Digested DNA is separated by gel electrophoresis, and hybridized with probes derived from, for example, genomic or cDNA sequences. The methylation status of the HIP gene can be determined by comparison of the restriction pattern generated from the sample DNA with that for a standard of known methylation.

In still other embodiments, the ligand binding domain of the HIP receptor can be used to quantitatively detect the level of HIP ligands, e.g., hedgehog proteins. To illustrate, a soluble form of the HIP protein can be generated which retains hedgehog binding activity. Samples of bodily fluid(s), e.g., plasma, serum, lymph, marrow, cerebral/spinal fluid, urine and the like can be contacted with the receptor under conditions wherein ligand/receptor binding can occur, and the level of ligand/receptor complexes formed can be detected by any of a variety of techniques known in the art. For example, competitive binding assays using standardized samples of hedgehog proteins can be used to quantitate the amount of analyte bound from the fluid sample.

In yet other embodiments, such HIP receptors can be used to detect the presence of a HIP ligand on a cell surface. For instance, the HIP protein can be contacted with cells from a biopsy, and the ability of the HIP protein to decorate certain cells of the sample is ascertained. The binding of the HIP protein to cell populations of the sample can be detected, for example, by the use of antibodies against the HIP protein, or by detection of a label associated with the HIP protein. In the case of the latter, the HIP protein can be labeled, for example, by chemical modification or as a fusion protein. Exemplary labels include radioisotopes, fluorescent compounds, enzyme co-factors, which can be added by chemical modification of the protein, and epitope tags such as myc, pFLAG and the like, or enzymatic activities such as GST or alkaline phosphatase which can be added either by chemical modification or by generation of a fusion protein.

Furthermore, the present invention also contemplates the detection of soluble forms of the HIP receptor in bodily fluid samples. As described in the art, e.g., see Diez-Ruiz et al. (1995) *Eur J Haematol* 54:1-8 and Owen-Schaub et al. (1995) *Cancer Lett* 94:1-8, [describing CNTF receptors] in certain instances soluble forms of receptors are believed to play a role as modulators of the biological function of their cognate ligands in an agonist/antagonist pattern. In various pathologic states, the production and release of soluble HIP proteins may mediate host response and determine the course and outcome of disease by interacting with HIP ligands and competing with cell surface receptors. The determination of soluble HIP receptors in body fluids is a new tool to gain information about various disease states, and may be of prognostic value to a clinician. For example, the level of soluble HIP protein in a body fluid may give useful information for monitoring, inter alia, neurological disorders as well as in the treatment of neoplastic or hyperplastic transformations of ectodermal, mesodermal or endodermal origin.

The level of soluble receptor present in a given sample can be quantitated, in light of the present disclosure, using known procedures and techniques. For example, antibodies immunoselective for the ligand binding domain of the HIP protein can be used to detect and quantify its presence in a sample, e.g., by well-known immunoassay techniques. Alternatively, a labeled ligand of the receptor can be used to detect the presence of the receptor in the fluid sample.

A number of techniques exist in the art for now identifying additional ligands to the HIP receptor. For instance, expression cloning can be carried out on a cDNA or genomic library by isolating cells which are decorated with a labeled form of the receptor. In a preferred embodiment, the technique uses the HIP receptor in an in situ assay for detecting HIP ligands in tissue samples and whole organisms. In general, the RAP-in situ assay described below (for Receptor Affinity Probe) of Flanagan and Leder (see PCT publications WO 92/06220; and also Cheng et al. (1994) *Cell* 79:157-168) involves the use of an expression cloning system whereby a HIP ligand is scored on the basis of binding to a HIP/alkaline phosphatase fusion protein. In general, the method comprises (i) providing a hybrid molecule (the affinity probe) including the HIP receptor, or at least the ligand binding domain thereof, covalently bonded to an enzymatically active tag, preferably for which chromogenic substrates exist, (ii) contacting the tissue or organism with the affinity probe to form complexes between the probe and a cognate ligand in the sample, removing unbound probe, and (iii) detecting the affinity complex using a chromogenic substrate for the enzymatic activity associated with the affinity probe.

This method, unlike other prior art methods which are carried out only on dispersed cell cultures, provides a means for probing non-dispersed and wholemount tissue and animal samples. The method can be used, in addition to facilitating the cloning of HIP ligands, also for detecting patterns of expression for particular ligands of the HIP receptor, for measuring the affinity of receptor/ligand interactions in tissue samples, as well as for generating drug screening assays in tissue samples. Moreover, the affinity probe can also be used in diagnostic screening to determine whether a HIP ligand is misexpressed.

In yet another aspect of the invention, the subject HIP polypeptides can be used to generate a "two hybrid" assay or an "interaction trap" assay (see, for example, U.S. Pat. No. 5,283,317; Zervos et al. (1993) Cell 72:223-232; Madura et al. (1993) J Biol Chem 268:12046-12054; Bartel et al. (1993) Biotechniques 14:920-924; Iwabuchi et al. (1993) Oncogene 8:1693-1696; and Brent WO94/10300), for isolating coding sequences for other proteins which bind HIPs ("HIP-binding proteins" or "HIP-bp").

Briefly, the interaction trap relies on reconstituting in vivo a functional transcriptional activator protein from two separate fusion proteins. In particular, the method makes use of chimeric genes which express hybrid proteins. To illustrate, a first hybrid gene comprises the coding sequence for a DNA-binding domain of a transcriptional activator fused in frame to the coding sequence for a HIP polypeptide. The second hybrid protein encodes a transcriptional activation domain fused in frame to a sample gene from a cDNA library. If the bait and sample hybrid proteins are able to interact, e.g., form a HIP-dependent complex, they bring into close proximity the two domains of the transcriptional activator. This proximity is sufficient to cause transcription of a reporter gene which is operably linked to a transcriptional regulatory site responsive to the transcriptional activator, and expression of the reporter gene can be detected and used to score for the interaction of the HIP and sample proteins.

Furthermore, by making available purified and recombinant HIP polypeptides, the present invention facilitates the development of assays which can be used to screen for drugs which are either agonists or antagonists of the normal cellular function of the subject HIP proteins, or of their role in the pathogenesis of cellular maintenance, differentiation and/or proliferation and disorders related thereto. In a general sense, the assay evaluates the ability of a compound to modulate binding between a HIP polypeptide and a molecule, e.g., a ligand such as a hedgehog protein, that interacts with the HIP polypeptide. Exemplary compounds which can be screened against such HIP-mediated interactions include peptides, nucleic acids, carbohydrates, small organic molecules, and natural product extract libraries, such as isolated from animals, plants, fungus and/or microbes.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with a ligand. Accordingly, in an exemplary screening assay of the present invention, a reaction mixture is generated to include a HIP polypeptide, compound(s) of interest, and a "target molecule", e.g., a protein, which interacts with the HIP polypeptide. Exemplary target molecules include ligands, such as hedgehog proteins, as well as other peptide and non-peptide interacting molecules. Detection and quantification of interaction of the HIP polypeptide with the target molecule provides a means for determining a compound's efficacy at inhibiting (or potentiating) interaction between the HIP and the target molecule. The efficacy of the compound can be assessed by generating dose response curves from data obtained using various concentrations of the test compound. Moreover, a control assay can also be performed to provide a baseline for comparison. In the control assay, interaction of the HIP polypeptide and target molecule is quantitated in the absence of the test compound.

Interaction between the HIP polypeptide and the target molecule may be detected by a variety of techniques. Modulation of the formation of complexes can be quantitated using, for example, detectably labeled proteins such as radiolabeled, fluorescently labeled, or enzymatically labeled HIP polypeptides, by immunoassay, by chromatographic detection, or by detecting the intrinsic activity of the acetylase.

Typically, it will be desirable to immobilize either HIP or the target molecule to facilitate separation of complexes from uncomplexed forms of one or both of the proteins, as well as to accommodate automation of the assay. Binding of HIP to the target molecule, in the presence and absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/HIP (GST/HIP) fusion proteins can be adsorbed onto glutathione sepharose beads (Sigma Chemical, St. Louis, Mo.) or glutathione derivatized microtitre plates, which are then combined with the cell lysates, e.g. an $^{35}$S-labeled, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes can be dissociated from the matrix, separated by SDS-PAGE, and the level of target molecule found in the bead fraction quantitated from the gel using standard electrophoretic techniques.

Other techniques for immobilizing proteins and other molecules on matrices are also available for use in the subject assay. For instance, either HIP or target molecule can be immobilized utilizing conjugation of biotin and streptavidin. For instance, biotinylated HIP molecules can be prepared from biotin-NHS(N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with HIP, but which do not interfere with the interaction between the HIP and target molecule, can be derivatized to the wells of the plate, and HIP trapped in the wells by antibody conjugation. As above, preparations of an target molecule and a test compound are incubated in the HIP-presenting wells of the plate, and the amount of complex trapped in the well can be quantitated. Exemplary methods for detecting such complexes, in addition to those described above for the GST-immobilized complexes, include immunodetection of complexes using antibodies reactive with the target molecule, or which are reactive with HIP protein and compete with the target molecule; as well as enzyme-linked assays which rely on detecting an enzymatic activity associated with the target molecule, either intrinsic or extrinsic activity. In the instance of the latter, the enzyme can be chemically conjugated or provided as a fusion protein with the target molecule. To illustrate, the target molecule can be chemically cross-linked or genetically fused (if it is a polypeptide) with horseradish peroxidase, and the amount of polypeptide trapped in the complex can be assessed with a chromogenic substrate of the enzyme, e.g. 3,3'-diamino-benzadine terahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al (1974) J Biol Chem 249:7130).

For processes which rely on immunodetection for quantitating proteins trapped in the complex, antibodies against the protein, such as anti-HIP antibodies, can be used. Alternatively, the protein to be detected in the complex can be "epitope tagged" in the form of a fusion protein which includes, in addition to the HIP sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150-21157) which includes a 10-residue sequence from c-myc, as well as the pFLAG system (International Biotechnologies, Inc.) or the pEZZ-protein A system (Pharamacia, N.J.).

An exemplary drug screening assay of the present invention includes the steps of (a) forming a reaction mixture including: (i) a hedgehog polypeptide, (ii) a HIP polypeptide, and (iii) a test compound; and (b) detecting interaction of the hedgehog and HIP polypeptides. A statistically significant change (potentiation or inhibition) in the interaction of the hedgehog and HIP polypeptides in the presence of the test compound, relative to the interaction in the absence of the test compound, indicates a potential agonist (mimetic or potentiator) or antagonist (inhibitor) of hedgehog bioactivity for the test compound. The reaction mixture can be a cell-free protein preparation, e.g., a reconsistuted protein mixture or a cell lysate, or it can be a recombinant cell including a heterologous nucleic acid recombinantly expressing the HIP polypeptide.

Where the HIP polypeptide participates as part of an oligomeric complex forming a hedgehog receptor, e.g., which complex includes other protein subunits, the cell-free system can be, e.g., a cell membrane preparation, a reconstituted protein mixture, or a liposome reconstituting the receptor subunits as a hedgehog receptor. Alternatively, liposomal preparations using reconstituted Hip protein can be utilized. For instance, the protein subunits of a hedgehog receptor complex can be purified from detergent extracts from both authentic and recombinant origins can be reconstituted in artificial lipid vesicles (e.g. phosphatidylcholine liposomes) or in cell membrane-derived vesicles (see, for example, Bear et al. (1992) *Cell* 68:809-818; Newton et al. (1983) *Biochemistry* 22:6110-6117; and Reber et al. (1987) *J Biol Chem* 262:11369-11374). The lamellar structure and size of the resulting liposomes can be characterized using electron microscopy. External orientation of the HIP protein in the reconstituted membranes can be demonstrated, for example, by immunoelectron microscopy. The interaction of a hedgehog protein with liposomes containing such HIP complexes and liposomes without the protein, in the presence of candidate agents, can be compared in order to identify potential modulators of the hedgehog-HIP polypeptide interaction.

In yet another embodiment, the drug screening assay is derived to include a whole cell expressing a HIP polypeptide. The ability of a test agent to alter the activity of the HIP protein can be detected by analysis of the recombinant cell. For example, agonists and antagonists of the HIP biological activity can by detected by scoring for alterations in growth or differentiation (phenotype) of the cell. General techniques for detecting each are well known, and will vary with respect to the source of the particular reagent cell utilized in any given assay. For the cell-based assays, the recombinant cell is preferably a metazoan cell, e.g., a mammalian cell, e.g., an insect cell, e.g., a xenopus cell, e.g., an oocyte. In other embodiments, the hedgehog receptor can be reconstituted in a yeast cell.

In an exemplary embodiment, a cell which expresses the HIP receptor, e.g, whether endogenous or heterologous, can be contacted with a ligand of the HIP receptor, e.g., a hedgehog protein, which is capable of inducing signal transduction from the receptor, and the resulting signaling detected either at various points in the pathway, or on the basis of a phenotypic change to the reagent cell. In one embodiment, the reagent cell is contacted with antibody which causes cross-linking of the receptor, and the signal cascade induced by that cross-linking is subsequently detected. A test compound which modulates that pathway, e.g., potentiates or inhibits, can be detected by comparison with control experiments which either lack the receptor or lack the test compound. For example, visual inspection of the morphology of the reagent cell can be used to determine whether the biological activity of the targeted HIP protein has been affected by the added agent.

In addition to morphological studies, change(s) in the level of an intracellular second messenger responsive to signaling by the HIP polypeptide can be detected. For example, in various embodiments the assay may assess the ability of test agent to cause changes in phophorylation patterns, adenylate cyclase activity (cAMP production), GTP hydrolysis, calcium mobilization, and/or phospholipid hydrolysis ($IP_3$, DAG production) upon receptor stimulation. By detecting changes in intracellular signals, such as alterations in second messengers or gene expression, in cells contacted with a hedgehog polypeptide, candidate agonists and antagonists to HIP-dependent hedgehog signaling can be identified.

The transduction of certain intracellular signals can be initiated by the specific interaction of an hh polypeptide with HIP protein, while other signals can be indirecetly altered by that iteraction. In *Drosophila*, and presumptively in vertebrate cells as well, a number of gene products, including HIP, patched, the transcription factor cubitus interruptus (ci), the serine/threonine kinase fused (fu) and the gene products of costal-2, smoothened and suppressor of fused, have been implicated as putative components of hedgehog-dependent signal transduction pathways. The recent cloning of vertebrate homologs of the *drosophila* genes suggests that the hedgehog signaling pathway is highly conserved from *drosophila* to vertebrate species. The activity of each of these proteins can be detected directly (such as the kinase activity of fused, or can detected indirectly by monitoring the level of second messengers produced downstream in the signal pathway.

To further illustrate, recent studies have implicated protein kinase A (PKA) as a possible component of hedgehog signaling in *drosophila* and vertebrate organisms (Hammerschmidt et al. (1996) *Genes & Dev* 10:647). High PKA activity has been shown to antagonize hedgehog signaling in these systems. Although it is unclear whether PKA acts directly downstream or in parallel with hedgehog signaling, it is possible that hedgehog signaling occurring through a HIP protein effects inhibition of PKA activity. Thus, detection of PKA activity provides a potential readout for the instant assays.

Binding of hedgehog to HIP proteins may stimulate the activity of phospholipases. Inositol lipids can be extracted and analyzed using standard lipid extraction techniques. Water soluble derivatives of all three inositol lipids ($IP_1$, $IP_2$, $IP_3$) can also be quantitated using radiolabelling techniques or HPLC.

The mobilization of intracellular calcium or the influx of calcium from outside the cell may be a response to hedgehog stimulation or lack there of. Calcium flux in the reagent cell can be measured using standard techniques. The choice of the appropriate calcium indicator, fluorescent, bioluminescent, metallochromic, or $Ca^{++}$-sensitive microelectrodes depends on the cell type and the magnitude and time constant of the event under study (Borle (1990) *Environ Health Perspect* 84:45-56). As an exemplary method of $Ca^{++}$ detection, cells could be loaded with the $Ca^{++}$ sensitive fluorescent dye fura-2 or indo-1, using standard methods, and any change in $Ca^{++}$ measured using a fluorometer.

In certain embodiments of the assay, it may be desirable to screen for changes in cellular phosphorylation. As an example, the *drosophila* gene fused (fu) which encodes a serine/threonine kinase has been identified as a potential downstream target in hedgehog signaling. (Preat et al., 1990 *Nature* 347, 87-89; Therond et al. 1993*, Mech. Dev.* 44. 65-80). The ability of compounds to modulate serine/threonine kinase activation could be screened using colony immunoblotting (Lyons and Nelson (1984) *PNAS* 81:7426-7430) using antibodies against phosphorylated serine or threonine residues. Reagents for performing such assays are commercially available, for example, phosphoserine and phosphothreonine specific antibodies which measure increases in phosphorylation of those residues can be purchased from commercial sources.

The interaction of a hedgehog protein with a HIP protein may set in motion a cascade involving the activation and inhibition of downstream effectors, the ultimate consequence of which is, in some instances, a detectable change in the transcription or translation of a gene. Potential transcriptional targets of HIP-dependent hedgehog signaling include the HIP gene itself, the patched gene (Hidalgo and Ingham (1990) *Development* 110, 291-301; Marigo et al. (1996) *Development* 122:1225-1233), and the vertebrate homologs of the *drosophila* cubitus interruptus (ci) gene, the GLI genes (Hui et al. (1994) *Dev Biol* 162:402-413). Patched gene expression has been shown to be induced in cells of the limb bud and the neural plate that are responsive to Shh. (Marigo et al. (1996)

*PNAS*, in press; Marigo et al., supra). The GLI genes encode putative transcription factors having zinc finger DNA binding domains (Orenic et al. (1990) *Genes & Dev* 4:1053-1067; Kinzler et al. (1990) *Mol Cell Biol* 10:634-642). Transcription of the GLI gene has been reported to be upregulated in response to hedgehog in limb buds, while transcription of the GLI3 gene is downregulated in response to hedgehog induction (Marigo et al. (1996) *Development* 122:1225-1233). By selecting transcriptional regulatory sequences from such target genes, e.g. from Hip or GLI genes, that are responsible for the up- or down-regulation of these genes in response to hedgehog induction, and operatively linking such promoters to a reporter gene, the present invention provides a transcription based assay which is sensitive to the ability of a specific test compound to influence hedgehog signalling pathways.

In an exemplary embodiment, the step of detecting interaction of the hedgehog and HIP polypeptides comprises detecting, in a cell-based assay, change(s) in the level of expression of a gene controlled by a transcriptional regulatory sequence responsive to signaling by the HIP polypeptide. Reporter gene based assays of this invention measure the end stage of the above described cascade of events, e.g., transcriptional modulation. Accordingly, in practicing one embodiment of the assay, a reporter gene construct is inserted into the reagent cell in order to generate a detection signal dependent on hedgehog signaling. Expression of the reporter gene, thus, provides a valuable screening tool for the development of compounds that act as agonists or antagonists of HIP-dependent hedgehog induction.

In practicing one embodiment of the assay, a reporter gene construct is inserted into the reagent cell in order to generate a detection signal dependent on second messengers generated by HIP-dependent induction with a hedgehog protein. Typically, the reporter gene construct will include a reporter gene in operative linkage with one or more transcriptional regulatory elements responsive to the hedgehog activity, with the level of expression of the reporter gene providing the hedgehog-dependent detection signal. The amount of transcription from the reporter gene may be measured using any method known to those of skill in the art to be suitable. For example, mRNA expression from the reporter gene may be detected using RNAse protection or RNA-based PCR, or the protein product of the reporter gene may be identified by a characteristic stain or an intrinsic activity. The amount of expression from the reporter gene is then compared to the amount of expression in either the same cell in the absence of the test compound or it may be compared with the amount of transcription in a substantially identical cell that lacks the target receptor protein. Any statistically or otherwise significant difference in the amount of transcription indicates that the test compound has in some manner altered the inductive activity of the hedgehog protein.

As described in further detail below, in preferred embodiments the gene product of the reporter is detected by an intrinsic activity associated with that product. For instance, the reporter gene may encode a gene product that, by enzymatic activity, gives rise to a detection signal based on color, fluorescence, or luminescence. In other preferred embodiments, the reporter or marker gene provides a selective growth advantage, e.g., the reporter gene may enhance cell viability, relieve a cell nutritional requirement, and/or provide resistance to a drug. Many reporter genes are known to those of skill in the art and others may be identified or synthesized by methods known to those of skill in the art. A reporter gene includes any gene that expresses a detectable gene product, which may be RNA or protein.

Preferred reporter genes are those that are readily detectable. The reporter gene may also be included in the construct in the form of a fusion gene with a gene that includes desired transcriptional regulatory sequences or exhibits other desirable properties. Examples of reporter genes include, but are not limited to CAT (chloramphenicol acetyl transferase) (Alton and Vapnek (1979), Nature 282: 864-869) luciferase, and other enzyme detection systems, such as beta-galactosidase; firefly luciferase (deWet et al. (1987), Mol. Cell. Biol. 7:725-737); bacterial luciferase (Engebrecht and Silverman (1984), PNAS 1: 4154-4158; Baldwin et al. (1984), Biochemistry 23: 3663-3667); alkaline phosphatase (Toh et al. (1989) Eur. J. Biochem. 182: 231-238, Hall et al. (1983) J. Mol. Appl. Gen. 2: 101), human placental secreted alkaline phosphatase (Cullen and Malim (1992) Methods in Enzymol. 216:362-368).

Accordingly, yet another embodiment of the subject drug screening assays of the present invention provides a recombinant cell, e.g., for carrying out certain of the drug screening methods above, comprising: (i) an expressible recombinant gene encoding a heterologous HIP polypeptide whose signal transduction activity is modulated by binding to a hedgehog protein; and (ii) a reporter gene construct containing a reporter gene in operative linkage with one or more transcriptional regulatory elements responsive to the signal transduction activity of the HIP polypeptide. Still another aspect of the present invention provides a kit for screening test compounds to identify agents which modulate the binding of hedgehog proteins with a hedgehog receptor, including the above-referenced cell and a preparation of purified hedgehog polypeptide.

In still another embodiment of a drug screening, a two hybrid assay (described supra) can be generated with a HIP polypeptide and target molecule. Drug dependent inhibition or potentiation of the interaction can be scored.

After identifying certain test compounds as potential modulators of one or more bioactivities of a HIP protein (such as hedgehog binding), the practioner of the subject assay will continue to test the efficacy and specificity of the selected compounds both in vitro and in vivo. Whether for subsequent in vivo testing, or for administration to an animal as an approved drug, agents identified in the subject assay can be formulated in pharmaceutical preparations for in vivo administration to an animal, preferably a human.

Another aspect of the present invention relates to a method of inducing and/or maintaining a differentiated state, enhancing survival, and/or inhibiting (or alternatively potentiating) proliferation of a cell, by contacting the cells with an agent which modulates HIP-dependent signal transduction pathways. The subject method could be used to generate and/or maintain an array of different tissue both in vitro and in vivo. A “HIP therapeutic,” whether inhibitory or potentiating with respect to modulating the activity of a HIP protein, can be, as appropriate, any of the preparations described above, including isolated HIP polypeptides (including both agonist and antagonist forms), gene therapy constructs, antisense molecules, peptidomimetics, or agents identified in the drug assays provided herein. In certain embodiments, soluble forms of the HIP protein including the extracellular ligand-binding domain of the receptor can be provided as a means for antagonizing the binding of a HIP ligand to a cell-surface HIP receptor. For instance, such forms of the receptor can be used to antagonize the bioactivity of a ligand of the receptor.

The HIP therapeutic compounds of the present invention are likely to play an important role in the modulation of cellular proliferation and maintenance of, for example, neuronal, testicular, osteogenic or chondrogenic tissues during disease states. It will also be apparent that, by transient use of modulators of HIP activities, in vivo reformation of tissue can be accomplished, e.g. in the development and maintenance of organs such as ectodermal patterning, as well as certain mesodermal and endodermal differentiation processes. By controlling the proliferative and differentiative potential for different cells, the subject HIP therapeutics can be used to reform injured tissue, or to improve grafting and morphology of transplanted tissue. For instance, HIP antagonists and agonists can be employed in a differential manner to regulate different stages of organ repair after physical, chemical or pathological insult. The present method is also applicable to cell culture techniques.

To further illustrate this aspect of the invention, in vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNF). Once a neuronal cell has become terminally-differentiated it typically will not change to another terminally differentiated cell-type. However, neuronal cells can nevertheless readily lose their differentiated state. This is commonly observed when they are grown in culture from adult tissue, and when they form a blastema during regeneration. The present method provides a means for ensuring an adequately restrictive environment in order to maintain neuronal cells at various stages of differentiation, and can be employed, for instance, in cell cultures designed to test the specific activities of other trophic factors. In such embodiments of the subject method, the cultured cells can be contacted with a HIP therapeutic, e.g., such as an agent identified in the assays described above which potentiate HIP-dependent hedgehog bioactivities, in order to induce neuronal differentiation (e.g. of a stem cell), or to maintain the integrity of a culture of terminally-differentiated neuronal cells by preventing loss of differentiation. Alternatively, a antagonist of hedgehog induction, as certain of the HIP homologs of the present invention are expected to be, can be used to prevent differentiation of progenitor cells in culture.

To further illustrate uses of HIP therapeutics which may be either hedgehog agonists or antagonists, it is noted that intracerebral grafting has emerged as an additional approach to central nervous system therapies. For example, one approach to repairing damaged brain tissues involves the transplantation of cells from fetal or neonatal animals into the adult brain (Dunnett et al. (1987) *J Exp Biol* 123:265-289; and Freund et al. (1985) *J Neurosci* 5:603-616). Fetal neurons from a variety of brain regions can be successfully incorporated into the adult brain, and such grafts can alleviate behavioral defects. For example, movement disorder induced by lesions of dopaminergic projections to the basal ganglia can be prevented by grafts of embryonic dopaminergic neurons. Complex cognitive functions that are impaired after lesions of the neocortex can also be partially restored by grafts of embryonic cortical cells. The differential use of hedgehog agonists and antagonists in the culture can control the timing and type of differentiation accessible by the culture.

In addition to the implantation of cells cultured in the presence of hedgehog agonists and antagonists and other in vitro uses, yet another aspect of the present invention concerns the therapeutic application of a HIP therapeutics to enhance survival of neurons and other neuronal cells in both the central nervous system and the peripheral nervous system. The ability of hedgehog protein to regulate neuronal differentiation during development of the nervous system and also presumably in the adult state indicates that certain of the hedgehog proteins, and accordingly HIP therapeutic which modulate hedgehog bioactivities, can be reasonably expected to facilitate control of adult neurons with regard to maintenance, functional performance, and aging of normal cells; repair and regeneration processes in chemically or mechanically lesioned cells; and prevention of degeneration and premature death which result from loss of differentiation in certain pathological conditions. In light of this understanding, the present invention specifically contemplates applications of the subject HIP therapeutics to the treatment of (prevention and/or reduction of the severity of) neurological conditions deriving from: (i) acute, subacute, or chronic injury to the nervous system, including traumatic injury, chemical injury, vasal injury and deficits (such as the ischemia resulting from stroke), together with infectious/inflammatory and tumor-induced injury; (ii) aging of the nervous system including Alzheimer's disease; (iii) chronic neurodegenerative diseases of the nervous system, including Parkinson's disease, Huntington's chorea, amylotrophic lateral sclerosis and the like, as well as spinocerebellar degenerations; and (iv) chronic immunological diseases of the nervous system or affecting the nervous system, including multiple sclerosis.

Many neurological disorders are associated with degeneration of discrete populations of neuronal elements and may be treatable with a therapeutic regimen which includes a HIP therapeutic that acts as a hedgehog agonist. For example, Alzheimer's disease is associated with deficits in several neurotransmitter systems, both those that project to the neocortex and those that reside with the cortex. For instance, the nucleus basalis in patients with Alzheimer's disease have been observed to have a profound (75%) loss of neurons compared to age-matched controls. Although Alzheimer's disease is by far the most common form of dementia, several other disorders can produce dementia. Several of these are degenerative diseases characterized by the death of neurons in various parts of the central nervous system, especially the cerebral cortex. However, some forms of dementia are associated with degeneration of the thalamus or the white matter underlying the cerebral cortex. Here, the cognitive dysfunction results from the isolation of cortical areas by the degeneration of efferents and afferents. Huntington's disease involves the degeneration of intrastraital and cortical cholinergic neurons and GABAergic neurons. Pick's disease is a severe neuronal degeneration in the neocortex of the frontal and anterior temporal lobes, sometimes accompanied by death of neurons in the striatum. Treatment of patients suffering from such degenerative conditions can include the application of HIP therapeutics in order to control, for example, differentiation and apoptotic events which give rise to loss of neurons (e.g. to enhance survival of existing neurons) as well as promote differentiation and repopulation by progenitor cells in the area affected.

In addition to degenerative-induced dementias, a pharmaceutical preparation of one or more of the subject HIP therapeutics can be applied opportunely in the treatment of neurodegenerative disorders which have manifestations of tremors and involuntary movements. Parkinson's disease, for example, primarily affects subcortical structures and is characterized by degeneration of the nigrostriatal pathway, raphe nuclei, locus cereleus, and the motor nucleus of vagus. Ballism is typically associated with damage to the subthalamic nucleus, often due to acute vascular accident. Also included are neurogenic and myopathic diseases which ultimately affect the somatic division of the peripheral nervous system and are manifest as neuromuscular disorders. Examples include chronic atrophies such as amyotrophic lateral sclerosis, Guillain-Barre syndrome and chronic peripheral neuropathy, as well as other diseases which can be manifest as progressive bulbar palsies or spinal muscular atrophies. The present method is amenable to the treatment of disorders of the cerebellum which result in hypotonia or ataxia, such as those lesions in the cerebellum which produce disorders in the limbs ipsilateral to the lesion. For instance, a preparation of a HIP therapeutic can used to treat a restricted form of cerebellar cortical degeneration involving the anterior lobes (vermis and leg areas) such as is common in alcoholic patients.

In an illustrative embodiment, the subject method is used to treat amyotrophic lateral sclerosis. ALS is a name given to a complex of disorders that comprise upper and lower motor neurons. Patients may present with progressive spinal muscular atrophy, progressive bulbar palsy, primary lateral sclerosis, or a combination of these conditions. The major pathological abnormality is characterized by a selective and progressive degeneration of the lower motor neurons in the spinal cord and the upper motor neurons in the cerebral cortex. The therapeutic application of a hedgehog agonist can be used alone, or in conjunction with other neurotrophic factors such as CNTF, BDNF or NGF to prevent and/or reverse motor neuron degeneration in ALS patients.

HIP therapeutics of the present invention can also be used in the treatment of autonomic disorders of the peripheral nervous system, which include disorders affecting the innervation of smooth muscle and endocrine tissue (such as glandular tissue). For instance, the subject method can be used to treat tachycardia or atrial cardiac arrhythmias which may arise from a degenerative condition of the nerves innervating the striated muscle of the heart.

Furthermore, a potential role for certain of the HIP therapeutics derives from the role of hedgehog proteins in development and maintenance of dendritic processes of axonal neurons. Potential roles for hedgehog agonists consequently include guidance for axonal projections and the ability to promote differentiation and/or maintenance of the innervating cells to their axonal processes. Accordingly, compositions comprising HIP therapeutics which agonize hedgehog activity, may be employed to support the survival and reprojection of several types of ganglionic neurons sympathetic and sensory neurons as well as motor neurons. In particular, such therapeutic compositions may be useful in treatments designed to rescue, for example, various neurons from lesion-induced death as well as guiding reprojection of these neurons after such damage. Such diseases include, but are not limited to, CNS trauma infarction, infection (such as viral infection with varicella-zoster), metabolic disease, nutritional deficiency, toxic agents (such as cisplatin treatment).

Moreover, certain of the HIP therapeutics (e.g., which antagonize hedgehog induction) may be useful in the selective ablation of sensory neurons, for example, in the treatment of chronic pain syndromes.

As appropriate, HIP therapeutics can be used in nerve prostheses for the repair of central and peripheral nerve damage. In particular, where a crushed or severed axon is intubulated by use of a prosthetic device, certain of HIP therapeutics can be added to the prosthetic device to increase the rate of growth and regeneration of the dendridic processes. Exemplary nerve guidance channels are described in U.S. Pat. Nos. 5,092,871 and 4,955,892. Accordingly, a severed axonal process can be directed toward the nerve ending from which it was severed by a prosthesis nerve guide.

In another embodiment, the subject method can be used in the treatment of neoplastic or hyperplastic transformations such as may occur in the central nervous system. For instance, certain of the HIP therapeutics which induce differentiation of neuronal cells can be utilized to cause such transformed cells to become either post-mitotic or apoptotic. Treatment with a HIP therapeutic may facilitate disruption of autocrine loops, such as TGF-β or PDGF autostimulatory loops, which are believed to be involved in the neoplastic transformation of several neuronal tumors. HIP therapeutics may, therefore, thus be of use in the treatment of, for example, malignant gliomas, medulloblastomas, neuroectodermal tumors, and ependymonas.

Yet another aspect of the present invention concerns the application of the discovery that hedgehog proteins are morphogenic signals involved in other vertebrate organogenic pathways in addition to neuronal differentiation as described above, having apparent roles in other endodermal patterning, as well as both mesodermal and endodermal differentiation processes. As described in the literature, Shh plays a role in proper limb growth and patterning by initiating expression of signaling molecules, including Bmp-2 in the mesoderm and Fgf-4 in the ectoderm. Thus, it is contemplated by the invention that compositions comprising certain of the HIP therapeutics can also be utilized for both cell culture and therapeutic methods involving generation and maintenance of non-neuronal tissue.

In one embodiment, the present invention makes use of the discovery that hedgehog proteins, such as Shh, are apparently involved in controlling the development of stem cells responsible for formation of the digestive tract, liver, lungs, and other organs which derive from the primitive gut. Shh serves as an inductive signal from the endoderm to the mesoderm, which is critical to gut morphogenesis. Therefore, for example, hedgehog agonists can be employed in the development and maintenance of an artificial liver which can have multiple metabolic functions of a normal liver. In an exemplary embodiment, a HIP therapeutic which acts as a hedgehog agonist can be used to induce differentiation of digestive tube stem cells to form hepatocyte cultures which can be used to populate extracellular matrices, or which can be encapsulated in biocompatible polymers, to form both implantable and extracorporeal artificial livers.

In another embodiment, therapeutic compositions of hedgehog agonists can be utilized in conjunction with transplantation of such artificial livers, as well as embryonic liver structures, to promote intraperitoneal implantation, vascularization, and in vivo differentiation and maintenance of the engrafted liver tissue.

In yet another embodiment, HIP therapeutics can be employed therapeutically to regulate such organs after physical, chemical or pathological insult. For instance, therapeutic compositions comprising hedgehog agonists can be utilized in liver repair subsequent to a partial hepatectomy. Similarly, therapeutic compositions containing hedgehog agonists can be used to promote regeneration of lung tissue in the treatment of emphysema.

In still another embodiment of the present invention, compositions comprising HIP therapeutics can be used in the in vitro generation of skeletal tissue, such as from skeletogenic stem cells, as well as the in vivo treatment of skeletal tissue deficiencies. The present invention particularly contemplates the use of HIP therapeutics which agonize a hedgehog a skeletogenic activity, such as an ability to induce chondrogenesis and/or osteogenesis. By "skeletal tissue deficiency", it is meant a deficiency in bone or other skeletal connective tissue at any site where it is desired to restore the bone or connective tissue, no matter how the deficiency originated, e.g. whether as a result of surgical intervention, removal of tumor, ulceration, implant, fracture, or other traumatic or degenerative conditions.

For instance, the present invention makes available effective therapeutic methods and compositions for restoring cartilage function to a connective tissue. Such methods are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a Taxation of a joint by a torn ligament, malignment of joints, bone fracture, or by hereditary disease. The present reparative method is also useful for remodeling cartilage matrix, such as in plastic or reconstructive surgery, as well as periodontal surgery. The present method may also be applied to improving a previous reparative procedure, for example, following surgical repair of a meniscus, ligament, or cartilage. Furthermore, it may prevent the onset or exacerbation of degenerative disease if applied early enough after trauma.

In one embodiment of the present invention, the subject method comprises treating the afflicted connective tissue with a therapeutically sufficient amount of a hedgehog agonist, particularly HIP therapeutic which agonizes Ihh activity, to generate a cartilage repair response in the connective tissue by stimulating the differentiation and/or proliferation of chondrocytes embedded in the tissue. Induction of chondrocytes by treatment with a hedgehog agonist can subsequently result in the synthesis of new cartilage matrix by the treated cells. Such connective tissues as articular cartilage, intrarticular cartilage (menisci), costal cartilage (connecting the true ribs and the sternum), ligaments, and tendons are particularly amenable to treatment in reconstructive and/or regenerative therapies using the subject method. As used herein, regenerative therapies include treatment of degenerative states which have progressed to the point of which impairment of the tissue is obviously manifest, as well as preventive treatments of tissue where degeneration is in its earliest stages or imminent. The subject method can further be used to prevent the spread of mineralisation into fibrotic tissue by maintaining a constant production of new cartilage.

In an illustrative embodiment, the subject method can be used to treat cartilage of a diarthroidal joint, such as a knee, an ankle, an elbow, a HIP, a wrist, a knuckle of either a finger or toe, or a temperomandibular joint. The treatment can be directed to the meniscus of the joint, to the articular cartilage of the joint, or both. To further illustrate, the subject method can be used to treat a degenerative disorder of a knee, such as which might be the result of traumatic injury (e.g., a sports injury or excessive wear) or osteoarthritis. An injection of a HIP therapeutic into the joint with, for instance, an arthroscopic needle, can be used to treat the afflicted cartilage. In some instances, the injected agent can be in the form of a hydrogel or other slow release vehicle described above in order to permit a more extended and regular contact of the agent with the treated tissue.

The present invention further contemplates the use of the subject method in the field of cartilage transplantation and prosthetic device therapies. To date, the growth of new cartilage from either transplantation of autologous or allogenic cartilage has been largely unsuccessful. Problems arise, for instance, because the characteristics of cartilage and fibrocartilage varies between different tissue: such as between articular, meniscal cartilage, ligaments, and tendons, between the two ends of the same ligament or tendon, and between the superficial and deep parts of the tissue. The zonal arrangement of these tissues may reflect a gradual change in mechanical properties, and failure occurs when implanted tissue, which has not differentiated under those conditions, lacks the ability to appropriately respond. For instance, when meniscal cartilage is used to repair anterior cruciate ligaments, the tissue undergoes a metaplasia to pure fibrous tissue. By promoting chondrogenesis, the subject method can be used to particularly addresses this problem, by causing the implanted cells to become more adaptive to the new environment and effectively resemble hypertrophic chondrocytes of an earlier developmental stage of the tissue. Thus, the action of chondrogensis in the implanted tissue, as provided by the subject method, and the mechanical forces on the actively remodeling tissue can synergize to produce an improved implant more suitable for the new function to which it is to be put.

In similar fashion, the subject method can be applied to enhancing both the generation of prosthetic cartilage devices and to their implantation. The need for improved treatment has motivated research aimed at creating new cartilage that is based on collagen-glycosaminoglycan templates (Stone et al. (1990) *Clin Orthop Relat Red* 252:129), isolated chondrocytes (Grande et al. (1989) *J Orthop Res* 7:208; and Takigawa et al. (1987) *Bone Miner* 2:449), and chondrocytes attached to natural or synthetic polymers (Walitani et al. (1989) *J Bone Jt Surg* 71B:74; Vacanti et al. (1991) *Plast Reconstr Surg* 88:753; von Schroeder et al. (1991) *J Biomed Mater Res* 25:329; Freed et al. (1993) *J Biomed Mater Res* 27:11; and the Vacanti et al. U.S. Pat. No. 5,041,138). For example, chondrocytes can be grown in culture on biodegradable, biocompatible highly porous scaffolds formed from polymers such as polyglycolic acid, polylactic acid, agarose gel, or other polymers which degrade over time as function of hydrolysis of the polymer backbone into innocuous monomers. The matrices are designed to allow adequate nutrient and gas exchange to the cells until engraftment occurs. The cells can be cultured in vitro until adequate cell volume and density has developed for the cells to be implanted. One advantage of the matrices is that they can be cast or molded into a desired shape on an individual basis, so that the final product closely resembles the patient's own ear or nose (by way of example), or flexible matrices can be used which allow for manipulation at the time of implantation, as in a joint.

In one embodiment of the subject method, the implants are contacted with a HIP therapeutic during the culturing process, such as an Ihh agonist, in order to induce and/or maintain differentiated chondrocytes in the culture in order as to further stimulate cartilage matrix production within the implant. In such a manner, the cultured cells can be caused to maintain a phenotype typical of a chondrogenic cell (i.e. hypertrophic), and hence continue the population of the matrix and production of cartilage tissue.

In another embodiment, the implanted device is treated with a HIP therapeutic in order to actively remodel the implanted matrix and to make it more suitable for its intended function. As set out above with respect to tissue transplants, the artificial transplants suffer from the same deficiency of not being derived in a setting which is comparable to the actual mechanical environment in which the matrix is implanted. The activation of the chondrocytes in the matrix by the subject method can allow the implant to acquire characteristics similar to the tissue for which it is intended to replace.

In yet another embodiment, the subject method is used to enhance attachment of prosthetic devices. To illustrate, the subject method can be used in the implantation of a periodontal prosthesis, wherein the treatment of the surrounding connective tissue stimulates formation of periodontal ligament about the prosthesis, as well as inhibits formation of fibrotic tissue proximate the prosthetic device.

In still further embodiments, the subject method can be employed for the generation of bone (osteogenesis) at a site in the animal where such skeletal tissue is deficient. Indian hedgehog is particularly associated with the hypertrophic chondrocytes that are ultimately replaced by osteoblasts. For instance, administration of a HIP therapeutic of the present invention can be employed as part of a method for treating bone loss in a subject, e.g. to prevent and/or reverse osteoporosis and other osteopenic disorders, as well as to regulate bone growth and maturation. For example, preparations comprising hedgehog agonists can be employed, for example, to induce endochondral ossification, at least so far as to facilitate the formation of cartilaginous tissue precursors to form the "model" for ossification. Therapeutic compositions of HIP therapeutics can be supplemented, if required, with other osteoinductive factors, such as bone growth factors (e.g. TGF-β factors, such as the bone morphogenetic factors BMP-2 and BMP-4, as well as activin), and may also include, or be administered in combination with, an inhibitor of bone resorption such as estrogen, bisphosphonate, sodium fluoride, calcitonin, or tamoxifen, or related compounds. However, it will be appreciated that hedgehog proteins, such as Ihh and Shh are likely to be upstream of BMPs, e.g. treatment with a hedgehog agonist will have the advantage of initiating endogenous expression of BMPs along with other factors.

In yet another embodiment, the HIP therapeutic of the present invention can be used in the treatment of testicular cells, so as to modulate spermatogenesis. In light of the finding that hedgehog proteins are involved in the differentiation and/or proliferation and maintenance of testicular germ cells, hedgehog antagonist can be utilized to block the action of a naturally-occurring hedgehog protein. In a preferred embodiment, the HIP therapeutic inhibits the biological activity of Dhh with respect to spermatogenesis, by competitively binding hedgehog in the testis. That is, the HIP therapeutic can be administered as a contraceptive formulation. Alternatively, HIP therapeutics which agonize the spermatogenic activity of Dhh can be used as fertility enhancers. In similar fashion, hedgehog agonists and antagonists are potentially useful for modulating normal ovarian function.

Another aspect of the invention features transgenic non-human animals which express a heterologous HIP gene of the present invention, and/or which have had one or more genomic HIP genes disrupted in at least a tissue or cell-types of the animal. Accordingly, the invention features an animal model for developmental diseases, which animal has one or more HIP allele which is mis-expressed. For example, an animal can be generated which has one or more HIP alleles deleted or otherwise rendered inactive. Such a model can then be used to study disorders arising from mis-expressed HIP genes, as well as for evaluating potential therapies for similar disorders.

The transgenic animals of the present invention all include within a plurality of their cells a transgene of the present invention, which transgene alters the phenotype of the "host cell" with respect to regulation by the HIP protein, e.g., of cell growth, death and/or differentiation. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described herein and those generally known in the art.

In one embodiment, the transgene construct is a knockout construct. Such transgene constructs usually are insertion-type or replacement-type constructs (Hasty et al. (1991) *Mol Cell Biol* 11:4509). The transgene constructs for disruption of a HIP gene are designed to facilitate homologous recombination with a portion of the genomic HIP gene so as to prevent the functional expression of the endogenous HIP gene. In preferred embodiments, the nucleotide sequence used as the knockout construct can be comprised of (1)-DNA from some portion of the endogenous HIP gene (exon sequence, intron sequence, promoter sequences, etc.) which direct recombination and (2) a marker sequence which is used to detect the presence of the knockout construct in the cell. The knockout construct is inserted into a cell, and integrates with the genomic DNA of the cell in such a position so as to prevent or interrupt transcription of the native HIP gene. Such insertion can occur by homologous recombination, i.e., regions of the knockout construct that are homologous to the endogenous HIP gene sequence hybridize to the genomic DNA and recombine with the genomic sequences so that the construct is incorporated into the corresponding position of the genomic DNA. The knockout construct can comprise (1) a full or partial sequence of one or more exons and/or introns of the HIP gene to be disrupted, (2) sequences which flank the 5' and 3' ends of the coding sequence of the HIP gene, or (3) a combination thereof.

A preferred knockout construct will delete, by targeted homologous recombination, essential structural elements of an endogenous HIP gene. For example, the targeting construct can recombine with the genomic HIP gene can delete a portion of the coding sequence, and/or essential transcriptional regulatory sequences of the gene.

Alternatively, the knockout construct can be used to interrupt essential structural and/or regulatory elements of an endogenous HIP gene by targeted insertion of a polynucleotide sequence. For instance, a knockout construct can recombine with a HIP gene and insert a nonhomologous sequence, such as a neo expression cassette, into a structural element (e.g., an exon) and/or regulatory element (e.g., enhancer, promoter, intron splice site, polyadenylation site, etc.) to yield a targeted HIP allele having an insertional disruption. The inserted nucleic acid can range in size from 1 nucleotide (e.g., to produce a frameshift) to several kilobases or more, and is limited only by the efficiency of the targeting technique.

Depending of the location and characteristics of the disruption, the transgene construct can be used to generate a transgenic animal in which substantially all expression of the targeted HIP gene is inhibited in at least a portion of the animal's cells. If only regulatory elements are targeted, some low-level expression of the targeted gene may occur (i.e., the targeted allele is "leaky").

The nucleotide sequence(s) comprising the knockout construct(s) can be obtained using methods well known in the art. Such methods include, for example, screening genomic libraries with HIP cDNA probes in order to identify the corresponding genomic HIP gene and regulatory sequences. Alternatively, where the cDNA sequence is to be used as part of the knockout construct, the cDNA may be obtained by screening a cDNA library as set out above.

In another embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with $H-2^b$, $H-2^d$ or $H-2^q$ haplotypes such as C57BL/6 or DBA/1. The line(s) used to practice this invention may themselves be transgenics, and/or may be knockouts (i.e., obtained from animals which have one or more genes partially or completely suppressed).

In one embodiment, the transgene construct is introduced into a single stage embryo. The zygote is the best target for micro-injection. The use of zygotes as a target for gene transfer has a major advantage in that in most cases the injected DNA will be incorporated into the host gene before the first cleavage (Brinster et al. (1985) *PNAS* 82:4438-4442). As a consequence, all cells of the transgenic animal will carry the incorporated transgene. This will in general also be reflected in the efficient transmission of the transgene to offspring of the founder since 50% of the germ cells will harbor the transgene.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1-7 days, depending on the species, and then reimplant them into the surrogate host.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from excised tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *PNAS* 73:1260-1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927-6931; Van der Putten et al. (1985) *PNAS* 82:6148-6152). Transfection is easily and efficiently obtained by culturing the blastomeres on a monolayer of virus-producing cells (Van der Putten, supra; Stewart et al. (1987) *EMBO J.* 6:383-388). Alternatively, infection can be performed at a later stage. Virus or virus-producing cells can be injected into the blastocoele (Jahner et al. (1982) *Nature* 298:623-628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154-156; Bradley et al. (1984) *Nature* 309:255-258; Gossler et al. (1986) *PNAS* 83: 9065-9069; and Robertson et al. (1986) *Nature* 322:445-448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468-1474.

In one embodiment, gene targeting, which is a method of using homologous recombination to modify an animal's genome, can be used to introduce changes into cultured embryonic stem cells. By targeting the HIP gene in ES cells, these changes can be introduced into the germlines of animals to generate chimeras. The gene targeting procedure is accomplished by introducing into tissue culture cells a DNA targeting construct that includes a segment homologous to a HIP locus, and which also includes an intended sequence modification to the HIP genomic sequence (e.g., insertion, deletion, point mutation). The treated cells are then screened for accurate targeting to identify and isolate those which have been properly targeted.

Gene targeting in embryonic stem cells is in fact a scheme contemplated by the present invention as a means for disrupting a HIP gene function through the use of a targeting transgene construct designed to undergo homologous recombination with HIP genomic sequences. Targeting construct can be arranged so that, upon recombination with an element of a HIP gene, a positive selection marker is inserted into (or replaces) coding sequences of the targeted HIP gene. The inserted sequence functionally disrupts the HIP gene, while also providing a positive selection trait.

Generally, the embryonic stem cells (ES cells) used to produce the knockout animals will be of the same species as the knockout animal to be generated. Thus for example, mouse embryonic stem cells will usually be used for generation of a HIP-knockout mice.

Embryonic stem cells are generated and maintained using methods well known to the skilled artisan such as those described by Doetschman et al. (1985) *J. Embryol. Exp. Morphol.* 87:27-45). Any line of ES cells can be used, however, the line chosen is typically selected for the ability of the cells to integrate into and become part of the germ line of a developing embryo so as to create germ line transmission of the knockout construct. Thus, any ES cell line that is believed to have this capability is suitable for use herein. The cells are cultured and prepared for knockout construct insertion using methods well known to the skilled artisan, such as those set forth by Robertson in: Teratocarcinomas and Embryonic Stem Cells: A Practical Approach, E. J. Robertson, ed. IRL Press, Washington, D.C. [1987]); by Bradley et al. (1986) *Current Topics in Devel. Biol.* 20:357-371); and by Hogan et al. (Manipulating the Mouse Embryo: A Laboratory Manual, Cold Spring Harbor Laboratory Press, Cold Spring Harbor, N.Y. [1986]).

Insertion of the knockout construct into the ES cells can be accomplished using a variety of methods well known in the art including for example, electroporation, microinjection, and calcium phosphate treatment. A preferred method of insertion is electroporation.

Each knockout construct to be inserted into the cell must first be in the linear form. Therefore, if the knockout construct has been inserted into a vector, linearization is accomplished by digesting the DNA with a suitable restriction endonuclease selected to cut only within the vector sequence and not within the knockout construct sequence.

For insertion, the knockout construct is added to the ES cells under appropriate conditions for the insertion method chosen, as is known to the skilled artisan. Where more than one construct is to be introduced into the ES cell, each knockout construct can be introduced simultaneously or one at a time.

If the ES cells are to be electroporated, the ES cells and knockout construct DNA are exposed to an electric pulse using an electroporation machine and following the manufacturer's guidelines for use. After electroporation, the ES cells are typically allowed to recover under suitable incubation conditions. The cells are then screened for the presence of the knockout construct.

Screening can be accomplished using a variety of methods. Where the marker gene is an antibiotic resistance gene, the ES cells may be cultured in the presence of an otherwise lethal concentration of antibiotic. Those ES cells that survive have presumably integrated the knockout construct. If the marker gene is other than an antibiotic resistance gene, a Southern blot of the ES cell genomic DNA can be probed with a sequence of DNA designed to hybridize only to the marker sequence Alternatively, PCR can be used. Finally, if the marker gene is a gene that encodes an enzyme whose activity can be detected (e.g., β-galactosidase), the enzyme substrate can be added to the cells under suitable conditions, and the enzymatic activity can be analyzed. One skilled in the art will be familiar with other useful markers and the means for detecting their presence in a given cell. All such markers are contemplated as being included within the scope of the teaching of this invention.

The knockout construct may integrate into several locations in the ES cell genome, and may integrate into a different location in each ES cell's genome due to the occurrence of random insertion events. The desired location of insertion is in a complementary position to the DNA sequence to be knocked out, e.g., the HIP coding sequence, transcriptional regulatory sequence, etc. Typically, less than about 1-5 percent of the ES cells that take up the knockout construct will actually integrate the knockout construct in the desired location. To identify those ES cells with proper integration of the knockout construct, total DNA can be extracted from the ES cells using standard methods. The DNA can then be probed on a Southern blot with a probe or probes designed to hybridize in a specific pattern to genomic DNA digested with particular restriction enzyme(s). Alternatively, or additionally, the genomic DNA can be amplified by PCR with probes specifically designed to amplify DNA fragments of a particular size and sequence (i.e., only those cells containing the knockout construct in the proper position will generate DNA fragments of the proper size).

After suitable ES cells containing the knockout construct in the proper location have been identified, the cells can be inserted into an embryo. Insertion may be accomplished in a variety of ways known to the skilled artisan, however a preferred method is by microinjection. For microinjection, about 10-30 cells are collected into a micropipet and injected into embryos that are at the proper stage of development to permit integration of the foreign ES cell containing the knockout construct into the developing embryo. For instance, the transformed ES cells can be microinjected into blastocytes.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent.

Offspring that are born to the foster mother may be screened initially for HIP disruptants, DNA from tissue of the offspring may be screened for the presence of the knockout construct using Southern blots and/or PCR as described above. Offspring that appear to be mosaics may then be crossed to each other, if they are believed to carry the knockout construct in their germ line, in order to generate homozygous knockout animals. Homozygotes may be identified by Southern blotting of equivalent amounts of genomic DNA from animals that are the product of this cross, as well as animals that are known heterozygotes and wild type animals.

Other means of identifying and characterizing the knockout offspring are available. For example, Northern blots can be used to probe the mRNA for the presence or absence of transcripts of either the HIP gene, the marker gene, or both. In addition, Western blots can be used to assess the (loss of) level of expression of the HIP gene knocked out in various tissues of the offspring by probing the Western blot with an antibody against the HIP protein, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies or HIP ligands, e.g., hedgehog proteins, to look for the presence or absence of the knockout construct gene product.

Animals containing more than one knockout construct and/or more than one transgene expression construct are prepared in any of several ways. The preferred manner of preparation is to generate a series of animals, each containing a desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s). Thus, a transgenic avian species can be generated by breeding a first transgenic bird in which the wild-type HIP gene is disrupted with a second transgenic bird which has been engineered to express a mutant HIP which retains most other biological functions of the receptor.

The transformed animals, their progeny, and cell lines of the present invention provide several important uses that will be readily apparent to one of ordinary skill in the art.

To illustrate, the transgenic animals and cell lines are particularly useful in screening compounds that have potential as prophylactic or therapeutic treatments of diseases such as may involve aberrant expression, or loss, of a HIP gene, or aberrant or unwanted activation of receptor signaling. Screening for a useful drug would involve administering the candidate drug over a range of doses to the transgenic animal, and assaying at various time points for the effect(s) of the drug on the disease or disorder being evaluated. Alternatively, or additionally, the drug could be administered prior to or simultaneously with exposure to induction of the disease, if applicable.

In one embodiment, candidate compounds are screened by being administered to the transgenic animal, over a range of doses, and evaluating the animal's physiological response to the compound(s) over time. Administration may be oral, or by suitable injection, depending on the chemical nature of the compound being evaluated. In some cases, it may be appropriate to administer the compound in conjunction with co-factors that would enhance the efficacy of the compound.

In screening cell lines derived from the subject transgenic animals for compounds useful in treating various disorders, the test compound is added to the cell culture medium at the appropriate time, and the cellular response to the compound is evaluated over time using the appropriate biochemical and/or histological assays. In some cases, it may be appropriate to apply the compound of interest to the culture medium in conjunction with co-factors that would enhance the efficacy of the compound.

All of the above-cited references and publications are hereby incorporated by reference.

EQUIVALENTS

Those skilled in the art will recognize, or be able to ascertain using no more than routine experimentation, numerous equivalents to the specific polypeptides, nucleic acids, methods, assays and reagents described herein. Such equivalents are considered to be within the scope of this invention.

We claim:

1. An isolated or recombinantly produced antibody or antibody fragment, wherein said antibody or antibody fragment can specifically bind to a Hedgehog Interacting Protein (HIP) polypeptide comprising an amino acid sequence identical to SEQ ID NO: 6.

2. The antibody or antibody fragment of claim 1, wherein said antibody or antibody fragment does not substantially bind to a HIP polypeptide comprising a HIP amino acid sequence identical to SEQ ID NO: 5.

3. The antibody or antibody fragment of claim 1, wherein said antibody or antibody fragment does not substantially bind to a HIP polypeptide comprising an amino acid sequence identical to a sequence selected from at least one of SEQ ID NOs: 5, 7, or 8.

4. The antibody or antibody fragment of claim 1, wherein said antibody or antibody fragment is a monoclonal antibody.

5. A hybridoma producing the antibody of claim 4.

6. The antibody or antibody fragment of claim 3, wherein said antibody or antibody fragment is a monoclonal antibody.

7. A hybridoma producing the antibody of claim 6.

* * * * *

UNITED STATES PATENT AND TRADEMARK OFFICE

CERTIFICATE OF CORRECTION

PATENT NO. : 7,585,671 B2

APPLICATION NO. : 11/438749

DATED : September 8, 2009

INVENTOR(S) : McMahon et al.

It is certified that error appears in the above-identified patent and that said Letters Patent is hereby corrected as shown below:

On the Title page, please replace "HEDGEHOG INTERACTING PROTEINS AND USES RELATED THERETO" with --ANTIBODIES TO HEDGEHOG INTERACTING PROTEINS--.

Signed and Sealed this

Twelfth Day of January, 2010

David J. Kappos

David J. Kappos

*Director of the United States Patent and Trademark Office*

UNITED STATES PATENT AND TRADEMARK OFFICE

CERTIFICATE OF CORRECTION

PATENT NO. : 7,585,671 B2
APPLICATION NO. : 11/438749
DATED : September 8, 2009
INVENTOR(S) : McMahon et al.

It is certified that error appears in the above-identified patent and that said Letters Patent is hereby corrected as shown below:

On the Title page, Item (54) and at Column 1, lines 1 and 2, title, please replace "HEDGEHOG INTERACTING PROTEINS AND USES RELATED THERETO" with --ANTIBODIES TO HEDGEHOG INTERACTING PROTEINS--.

This certificate supersedes the Certificate of Correction issued January 12, 2010.

Signed and Sealed this

Second Day of February, 2010

David J. Kappos
*Director of the United States Patent and Trademark Office*

UNITED STATES PATENT AND TRADEMARK OFFICE

CERTIFICATE OF CORRECTION

PATENT NO. : 7,585,671 B2
APPLICATION NO. : 11/438749
DATED : September 8, 2009
INVENTOR(S) : McMahon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 289 days.

Signed and Sealed this

Fourteenth Day of September, 2010

David J. Kappos

*Director of the United States Patent and Trademark Office*